US009213032B2

(12) United States Patent
Lee et al.

(10) Patent No.: US 9,213,032 B2
(45) Date of Patent: *Dec. 15, 2015

(54) USE OF LRIG1 AS A BIOMARKER FOR IDENTIFYING A SUBJECT FOR APPLICATION OF ANTI-C-MET ANTIBODIES

(71) Applicant: SAMSUNG ELECTRONICS CO., LTD., Suwon-si, Gyeonggi-do (KR)

(72) Inventors: Ji Min Lee, Seoul (KR); Kyung Ah Kim, Seongnam-si (KR); Bo Gyou Kim, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,041

(22) Filed: Jul. 23, 2013

(65) Prior Publication Data

US 2014/0105902 A1    Apr. 17, 2014

(30) Foreign Application Priority Data

Jul. 23, 2012  (KR) .................. 10-2012-0080144
Sep. 14, 2012  (KR) .................. 10-2012-0102398

(51) Int. Cl.
| G01N 33/53 | (2006.01) |
| G01N 33/574 | (2006.01) |
| C12Q 1/68 | (2006.01) |
| C07K 16/30 | (2006.01) |
| C07K 16/28 | (2006.01) |
| A61K 39/00 | (2006.01) |

(52) U.S. Cl.
CPC ...... *G01N 33/57492* (2013.01); *C07K 16/2863* (2013.01); *C07K 16/30* (2013.01); *C12Q 1/6886* (2013.01); *G01N 33/57496* (2013.01); *A61K 2039/505* (2013.01); *C07K 2317/24* (2013.01); *C07K 2317/622* (2013.01); *C07K 2317/73* (2013.01); *C07K 2317/76* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| 7,858,300 | B2 | 12/2010 | Watier et al. |
| 8,076,066 | B2 | 12/2011 | Mass |
| 2003/0175760 | A1 | 9/2003 | Walker et al. |
| 2010/0062441 | A1 | 3/2010 | Salgia |
| 2010/0115639 | A1 | 5/2010 | Goetsch |
| 2011/0123996 | A1 | 5/2011 | Watier et al. |
| 2011/0281263 | A1 | 11/2011 | Matthiesen et al. |
| 2011/0281748 | A1 | 11/2011 | Singh et al. |
| 2012/0089541 | A1 | 4/2012 | Patel et al. |
| 2012/0142784 | A1 | 6/2012 | Schüle et al. |
| 2013/0089556 | A1 | 4/2013 | Cheong et al. |

FOREIGN PATENT DOCUMENTS

| KR | 1020130036992 A | 4/2013 |
| WO | WO 03/035904 A2 | 5/2003 |
| WO | WO 03/048729 A2 | 6/2003 |

OTHER PUBLICATIONS

Shattuck et al (Molecular and Cellular Biology, 2007, 27(5): 1934-1946).*
Hedman et al (Acta Oncologia, 2010, 49: 812-815).*
Ito et al (Virchows Arch, 2004, 444(4): 324-331).*
Eder et al (Clin Cancer Res, 2009, 15(7): 2207-2214).*
Lee et al., "Cbl-independent degradation of Met: ways to avoid agonism of bivalent Met-targeting antibody," *Oncogene*: 1-10 (2012).
Asaoka et al., Gastric cancer cell line Hs746T harbors a splice site mutation of c-Met causing juxtamembrane domain deletion, *Biochem Biophys Research Communications*, 394: 1042-1046 (2010).
Greenall et al., Non-Agonistic Bivalent Antibodies That Promote c-MET Degradation and Inhibit Tumor Growth and Others Specific for Tumor Related c-Met, *PLoS One*, 7(4):1-10 (e34658) (2012).
Hedman et al., LRIG inhibitors of growth factor signalling—double-edged swords in human cancer?, *European Journal of Cancer*, 43: 676-682 (2007).
Kong-Beltran et al., Somatic Mutations Lead to an Oncogenic Deletion of Met in Lung Cancer, *Cancer Research*, 66: 283-289 (2006).
Lai et al., Met Kinase-Dependent Loss of the E3 Ligase Cbl in Gastric Cancer, *J Biol Chem*, pp. 1-23 (2012).
Ma et al., c-MET Mutational Analysis in Small Cell Lung Cancer: Novel Juxtamembrane Domain Mutations Regulating Cytoskeletal Functions, *Cancer Research*, 63: 6272-6281 (2003).
Onozato et al., Activation of MET by Gene Amplification or by Splice Mutations Deleting the Juxtamembrane Domain in Primary Resected Lung Cancers, *J Thoracic Oncology*, 4: 5-11 (2009).
Petrelli et al., The endophilin—CIN85—Cbl complex mediates ligand-dependent downregulation of c-Met, *Nature*, 416:187-190 (2002).
Sanada et al., Gain-of-function of mutated C-CBL tumour suppressor in myeloid neoplasms, *Nature*, 460: 904-908 (2009).
Stutz et al., LRIG1 negatively regulates the oncogenic EGF receptor mutant EGFRvIII, *Oncogene*, 27: 5741-5752 (2008).
Shattuck et al., LRIG1 Is a Novel Negative Regulator of the Met Receptor and Opposes Met and Her2 Synergy, *Molecular and Cellular Biology*, vol. 27, No. 5, p. 1934-1946 (2007).

* cited by examiner

*Primary Examiner* — Sean Aeder
(74) *Attorney, Agent, or Firm* — Leydig, Voit & Mayer, Ltd.

(57) ABSTRACT

A method of identifying a cell sample or subject suitable for treatment with an anti-c-Met antibody or antigen-binding fragment thereof that specifically binds to an epitope within a SEMA domain of a c-Met protein by determining the presence of LRIG1 in a cell sample from the subject, as well as related methods and compositions.

**13 Claims, 24 Drawing Sheets
(6 of 24 Drawing Sheet(s) Filed in Color)**

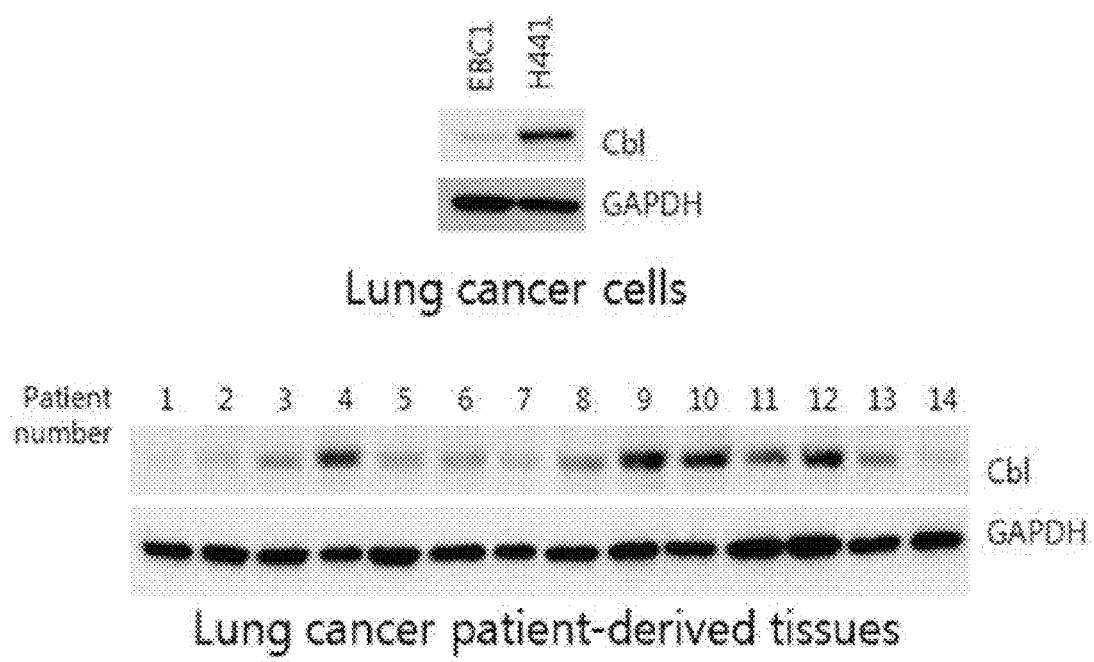

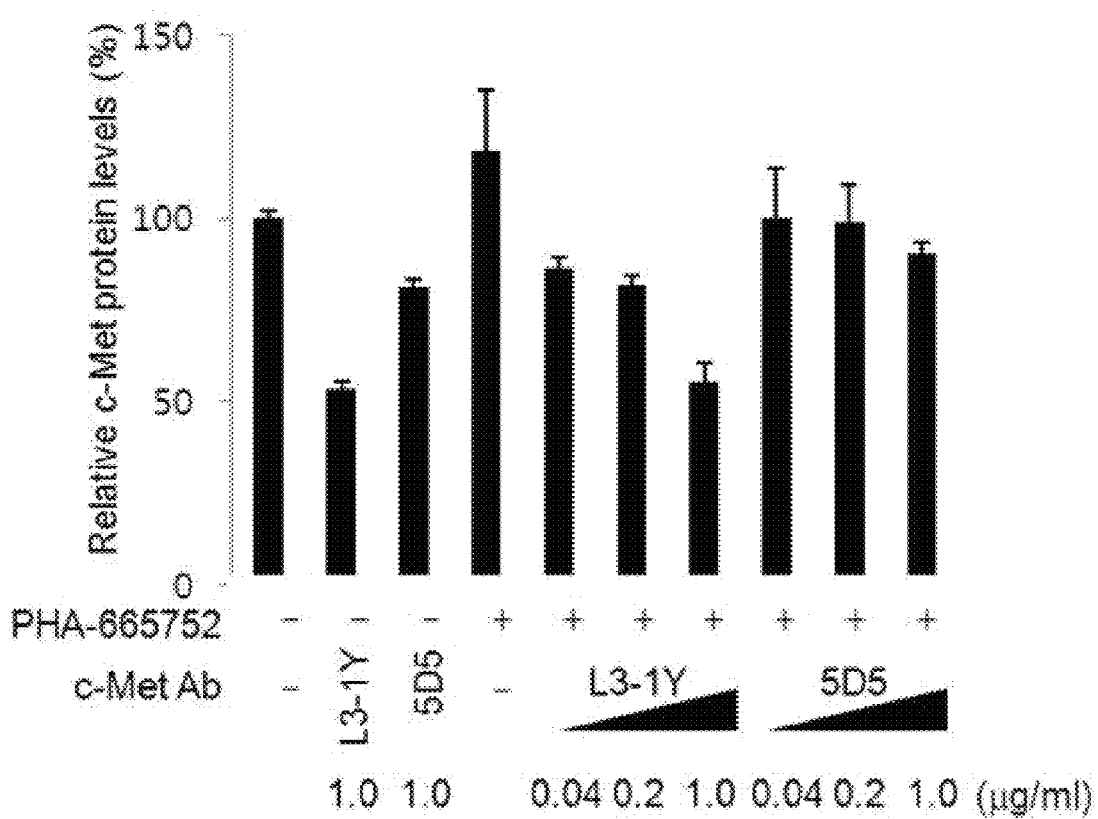

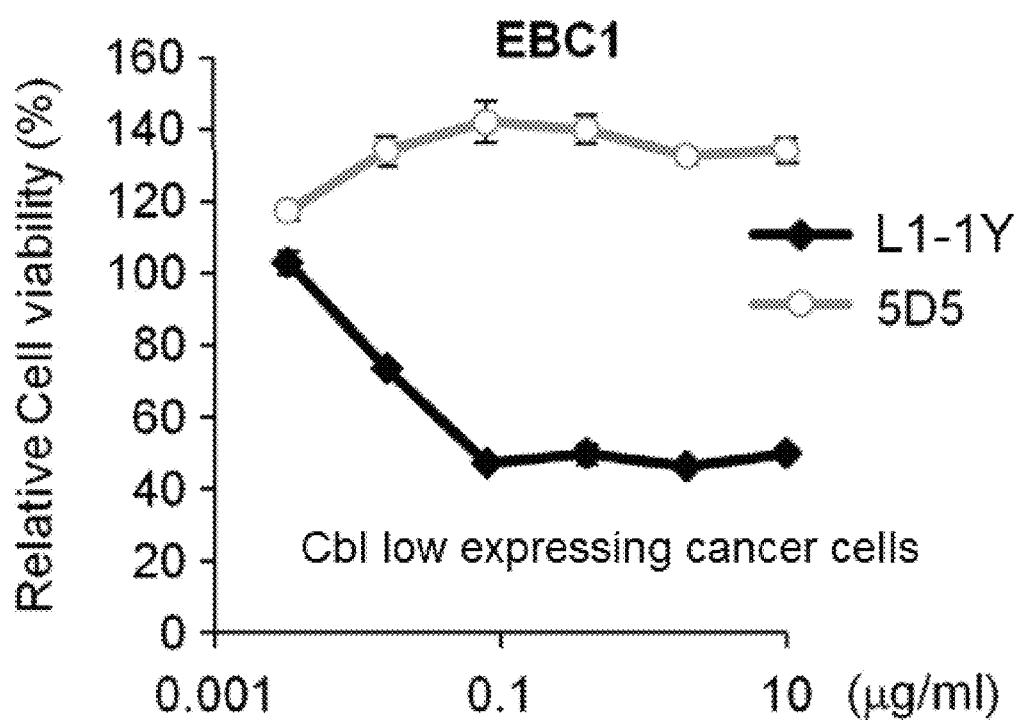

EBC1

293T

LRIG1-complex purification using 293 systems
In vitro binding (domain mapping) between c-Met and LRIG1

Efficacy : % of (-) ctr : Colony # at
Max dose (100ug/ml)

| Tumor | Efficacy (L3-1Y) |
|---|---|
| LXFE1422 | no |
| LXFA 526 | ++ (56) |
| LXFA 1647 | + (67) |

SEQUENCE LISTING

```
<160> NUMBER OF SEQ ID NOS: 114

<210> SEQ ID NO 1
<211> LENGTH: 5
<212> TYPE: PRT
<213> ORGANISM: Artificial Sequence
<220> FEATURE:
```

```
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MISC_FEATURE
<222> LOCATION: (1)..(1)
<223> OTHER INFORMATION: Xaa is Pro or Ser
<220> FEATURE:
<221> NAME/KEY: MISC_FEATURE
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MISC_FEATURE
<222> LOCATION: (3)..(3)
<223> OTHER INFORMATION: Xaa is Asn or Lys
<220> FEATURE:
<221> NAME/KEY: MISC_FEATURE
<222> LOCATION: (4)..(4)
<223> OTHER INFORMATION: Xaa is Ala or Val
<220> FEATURE:
<221> NAME/KEY: MISC_FEATURE
<222> LOCATION: (7)..(7)
<223> OTHER INFORMATION: Xaa is Asn or Thr

<400> SEQUENCE: 5

Arg Asn Xaa Xaa Asn Gly Xaa Thr
```

```
<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MISC_FEATURE
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MISC_FEATURE
<222> LOCATION: (4)..(4)
<223> OTHER INFORMATION: Xaa is His, Arg, Gln or Lys
<220> FEATURE:
<221> NAME/KEY: MISC_FEATURE
<222> LOCATION: (12)..(12)
<223> OTHER INFORMATION: Xaa is His or Gln
<220> FEATURE:
<221> NAME/KEY: MISC_FEATURE
<222> LOCATION: (13)..(13)
<223> OTHER INFORMATION: Xaa is Lys or Asn

<400> SEQUENCE: 7

Lys Ser Ser Xaa Ser Leu Leu Ala Ser Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MISC_FEATURE
<222> LOCATION: (2)..(2)
<223> OTHER INFORMATION: Xaa is Ala or Gly
<220> FEATURE:
<221> NAME/KEY: MISC_FEATURE
<222> LOCATION: (4)..(4)
<223> OTHER INFORMATION: Xaa is Thr or Lys
<220> FEATURE:
<221> NAME/KEY: MISC_FEATURE
<222> LOCATION: (4)..(4)
<223> OTHER INFORMATION: Xaa is Ser or Pro
<220> FEATURE:
<221> NAME/KEY: misc_feature
<222> LOCATION: (7)..(7)
<223> OTHER INFORMATION: Xaa can be any naturally occurring amino acid

<400> SEQUENCE: 8

Trp Xaa Ser Xaa Arg Val Xaa
1               5

<210> SEQ ID NO 9
<211> LENGTH: 9
<212> TYPE: PRT
```

```
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MISC_FEATURE
<222> LOCATION: (1)..(1)
<223> OTHER INFORMATION: Xaa is Gly, Ala or Gln
<220> FEATURE:
<221> NAME/KEY: MISC_FEATURE
<222> LOCATION: (6)..(6)
<223> OTHER INFORMATION: Xaa is Arg, His, Ser, Ala, Gly or Lys
<220> FEATURE:
<221> NAME/KEY: MISC_FEATURE
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
```

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

```
<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45
```

Ala Pro Lys Met Leu Ile Ile Trp Ala Ser Thr Arg Val Ser Gly Val
            50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
            50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence

```
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
```

```
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15
Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15
Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35
```

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360

```
gcaagagata actggtttgc ttactggggc caagggactc tggtcactgt ctctgcagct      420
agcaccaagg gcccatcggt cttcccctg gcaccctcct ccaagagcac ctctgggggc       480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                              1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(90)
<223> OTHER INFORMATION: signal sequence
<220> FEATURE:
<221> NAME/KEY: misc_feature
<222> LOCATION: (91)..(432)
<223> OTHER INFORMATION: VL - light chain variable region
<220> FEATURE:
<221> NAME/KEY: misc_feature
<222> LOCATION: (430)..(435)
<223> OTHER INFORMATION: BsiWI restriction site
<220> FEATURE:
<221> NAME/KEY: misc_feature
<222> LOCATION: (433)..(750)
<223> OTHER INFORMATION: CL - light chain constant region
<220> FEATURE:
<221> NAME/KEY: misc_feature
<222> LOCATION: (751)..(753)
<223> OTHER INFORMATION: stop codon
<220> FEATURE:
<221> NAME/KEY: misc_feature
<222> LOCATION: (754)..(759)
<223> OTHER INFORMATION: XhoI restriction site

<400> SEQUENCE: 39

```
gaattcacta gtgattaatt cgccgccacc atgattcac aggcccaggt cctcatgttg       60
ctgctgctat cggtatctgg tacctgtgga gacattttga tgacccagtc tccatcctcc     120
```

```
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
            245                 250                 255
Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
              165                 170                 175
Ser Gly Leu Tyr Ser Leu Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
```

```
                  85                  90                  95
Tyr Cys Ala Arg Asp Asn Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
```

```
              1               5                  10                 15
            Glu Arg Ala Thr Ile Asn Cys Lys Ser Ser Gln Ser Leu Leu Ala Ser
                            20                  25                 30

Gly Asn Gln Asn Asn Tyr Leu Ala Trp His Gln Gln Lys Pro Gly Gln
                    35                  40                  45

Pro Pro Lys Met Leu Ile Ile Trp Ala Ser Thr Arg Val Ser Gly Val
                50                  55                  60

Pro Asp Arg Phe Ser Gly Ser Gly Ser Gly Thr Asp Phe Thr Leu Thr
             65                  70                  75                  80

Ile Ser Ser Leu Gln Ala Glu Asp Val Ala Val Tyr Tyr Cys Gln Gln
                            85                  90                  95

Ser Tyr Ser Ala Pro Leu Thr Phe Gly Gly Gly Thr Lys Val Glu Ile
                        100                 105                 110

Lys Arg Thr Val Ala Ala Pro Ser Val Phe Ile Phe Pro Pro Ser Asp
                        115                 120                 125

Glu Gln Leu Lys Ser Gly Thr Ala Ser Val Val Cys Leu Leu Asn Asn
                    130                 135                 140

Phe Tyr Pro Arg Glu Ala Lys Val Gln Trp Lys Val Asp Asn Ala Leu
            145                 150                 155                 160

Gln Ser Gly Asn Ser Gln Glu Ser Val Thr Glu Gln Asp Ser Lys Asp
                            165                 170                 175

Ser Thr Tyr Ser Leu Ser Ser Thr Leu Thr Leu Ser Lys Ala Asp Tyr
                        180                 185                 190

Glu Lys His Lys Val Tyr Ala Cys Glu Val Thr His Gln Gly Leu Ser
                        195                 200                 205

Ser Pro Val Thr Lys Ser Phe Asn Arg Gly Glu Cys
                        210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light

<400> SEQUENCE: 44

Asp Ile Val Met Thr Gln Thr Pro Leu Ser Leu Pro Val Thr Pro Gly
             1               5                  10                 15

Glu Pro Ala Ser Ile Ser Cys Lys Ser Ser Gln Ser Leu Leu Ala Ser
                            20                  25                 30

Gly Asn Gln Asn Asn Tyr Leu Ala Trp His Leu Gln Lys Pro Gly Gln
                    35                  40                  45

Ser Pro Gln Met Leu Ile Ile Trp Ala Ser Thr Arg Val Ser Gly Val
                50                  55                  60

Pro Asp Arg Phe Ser Gly Ser Gly Ser Gly Thr Asp Phe Thr Leu Lys
             65                  70                  75                  80

Ile Ser Arg Val Glu Ala Glu Asp Val Gly Val Tyr Tyr Cys Gln Gln
                            85                  90                  95

Ser Tyr Ser Ala Pro Leu Thr Phe Gly Gln Gly Thr Lys Leu Glu Leu
                        100                 105                 110

Lys Arg Thr Val Ala Ala Pro Ser Val Phe Ile Phe Pro Pro Ser Asp
                        115                 120                 125

Glu Gln Leu Lys Ser Gly Thr Ala Ser Val Val Cys Leu Leu Asn Asn
                    130                 135                 140

Phe Tyr Pro Arg Glu Ala Lys Val Gln Trp Lys Val Asp Asn Ala Leu
```

```
                145                 150                 155                 160
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15
```

Asp Arg Val Thr Ile Thr Cys Lys Ser Ser Gln Ser Leu Ala Ser
          20                  25                  30

Gly Asn Gln Asn Asn Tyr Leu Ala Trp His Gln Lys Pro Gly Lys
         35                   40                  45

Ala Pro Lys Met Leu Ile Ile Trp Ala Ser Thr Arg Val Ser Gly Val
50                       55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt tgcttactg ggtcaagga accctggtca ccgtctcctc ggctagcacc       360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900

```
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa     1020 gggcagcccc gagaaccaca ggtgtacacc ctgcccccat cccgggagga gatgaccaag     1080
aaccaggtca gcctgacctg cctggtcaaa ggcttctatc cagcgacat cgccgtggag     1140 tgggagagca atgggcagcc ggagaacaac tacaagacca cgcctcccgt gctggactcc    1200
gacggctcct tcttcctcta cagcaagctc accgtggaca gagcaggtg gcagcagggg     1260 aacgtcttct catgctccgt gatgcatgag gctctgcaca accactacac gcagaagagc    1320
ctctccctgt ctccgggtaa atgactcgag                                     1350

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaccatctc caaagccaaa    1020 gggcagcccc gagaaccaca ggtgtacacc ctgcccccat cccgggagga gatgaccaag    1080
aaccaggtca gcctgacctg cctggtcaaa ggcttctatc cagcgacat cgccgtggag    1140 tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320
ctctccctgt ctccgggtaa atgactcgag                                    1350

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)
```

<400> SEQUENCE: 49

```
gaggttcagc tggtggagtc tggcggtggc ctggtgcagc caggggggctc actccgtttg    60
tcctgtgcag cttctggctt caccttcact gattactaca tgagctgggt gcgtcaggcc   120
ccgggtaagg gcctggaatg gttgggtttt attagaaaca aagctaatgg ttacacaaca   180
gagtacagtg catctgtgaa gggtcgtttc actataagca gagataattc caaaaacaca   240
ctgtacctgc agatgaacag cctgcgtgct gaggacactg ccgtctatta ttgtgctaga   300
gataactggt ttgcttactg gggccaaggg actctggtca ccgtctcctc ggctagcacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagcc caaatcttgt   660
gacaaaactc acacatgccc accgtgccca gcacctgaac tcctgggggg accgtcagtc   720
ttcctcttcc ccccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcgggagg agcagtacaa cagcacgtac   900
cgtgtggtca gcgtcctcac cgtcctgcac caggactggc tgaatggcaa ggagtacaag   960
tgcaaggtct ccaacaaagc cctcccagcc cccatcgaga aaaccatctc caaagccaaa  1020
gggcagcccc gagaaccaca ggtgtacacc ctgcccccat cccgggagga gatgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca gagcaggtg gcagcagggg  1260
aacgtcttct catgctccgt gatgcatgag gctctgcaca accactacac gcagaagagc  1320
ctctccctgt ctccgggtaa atgactcgag                                    1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

```
gacatcgtga tgacccagtc tccagactcc ctggctgtgt ctctgggcga gagggccacc    60
atcaactgca gtccagcca gagtctttta gctagcggac caaaataa ctacttagct    120
tggcaccagc agaaaccagg acagcctcct aagatgctca ttatttgggc atctacccgg   180
gtatccgggg tccctgaccg attcagtggc agcgggtctg gacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
```

```
gaagtcaccc atcagggcct gagctcgccc gtcacaaaga gcttcaacag gggagagtgt    660
tgactcgag                                                            669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc     60
atctcctgca agtccagtca gagtctttta gctagtggca accaaaataa ctacttggcc    120
tggcacctgc agaagccagg gcagtctcca cagatgctga tcatttgggc atccactagg    180
gtatctggag tcccagacag gttcagtggc agtgggtcag gcactgattt cacactgaaa    240
atcagcaggg tggaggctga ggatgttgga gtttattact gccagcagtc ctacagcgct    300
ccgctcacgt tcggacaggg taccaagctg gagctcaaac gtacggtggc tgcaccatct    360
gtcttcatct cccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

```
gacatcgtga tgacccagtc tccagactcc ctggctgtgt ctctgggcga gagggccacc     60
atcaactgca agtccagcca gagtctttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct cccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

```
gatatccaga tgacccagtc cccgagctcc ctgtccgcct ctgtgggcga tagggtcacc      60
atcacctgca agtccagtca gagtctttta gctagtggca accaaaataa ctacttggcc     120
tggcaccaac agaaaccagg aaaagctccg aaaatgctga ttatttgggc atccactagg     180
gtatctggag tcccttctcg cttctctgga tccgggtctg ggacggattt cactctgacc     240
atcagcagtc tgcagccgga agacttcgca acttattact gtcagcagtc ctacagcgct     300
ccgctcacgt tcggacaggg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaaagt ctacgcctgc     600
gaagtcaccc atcagggcct gagctcgccc gtcacaaaga gcttcaacag gggagagtgt     660
tgactcgag                                                              669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

```
Gly Leu Gly Gly Leu Gly Gly Gly Ser Gly Gly Gly Gly Ser Gly
1               5                   10                  15
Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of huAbF46 antibody)

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga acaccttgta cttgcaaatg aactccttga gagctgaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt cgctactta ctactgtcaa     720
caatcttact ctgctccatt gacttttggt caaggtacaa aggtcgaaat caagagagaa     780
```

| | |
|---|---|
| ttcggtaagc ctatccctaa ccctctcctc ggtctcgatt ctacgggtgg tggtggatct | 840 |
| ggtggtggtg gttctggtgg tggtggttct caggaactga caactatatg cgagcaaatc | 900 |
| ccctcaccaa ctttagaatc gacgccgtac tctttgtcaa cgactactat tttggccaac | 960 |
| gggaaggcaa tgcaaggagt ttttgaatat tacaaatcag taacgtttgt cagtaattgc | 1020 |
| ggttctcacc cctcaacaac tagcaaaggc agccccataa acacacagta tgttttttga | 1080 |
| gtttaaac | 1088 |

```
<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including
      polynucleotide encoding scFv of huAbF46 antibody)
<220> FEATURE:
<221> NAME/KEY: misc_feature
<222> LOCATION: (573)..(578)
<223> OTHER INFORMATION: NheI restriction site
<220> FEATURE:
<221> NAME/KEY: misc_feature
<222> LOCATION: (588)..(938)
<223> OTHER INFORMATION: huAbF46 VH
<220> FEATURE:
<221> NAME/KEY: misc_feature
<222> LOCATION: (939)..(1007)
<223> OTHER INFORMATION: linker
<220> FEATURE:
<221> NAME/KEY: misc_feature
<222> LOCATION: (1008)..(1349)
<223> OTHER INFORMATION: huAbF46 VL
<220> FEATURE:
<221> NAME/KEY: misc_feature
<222> LOCATION: (1350)..(1355)
<223> OTHER INFORMATION: EcoRI restriction site
<220> FEATURE:
<221> NAME/KEY: misc_feature
<222> LOCATION: (1356)..(1397)
<223> OTHER INFORMATION: V5 epitope
<220> FEATURE:
<221> NAME/KEY: misc_feature
<222> LOCATION: (1398)..(1442)
<223> OTHER INFORMATION: (G4S)3 linker
<220> FEATURE:
<221> NAME/KEY: misc_feature
<222> LOCATION: (1443)..(1649)
<223> OTHER INFORMATION: Aga2
<220> FEATURE:
<221> NAME/KEY: misc_feature
<222> LOCATION: (1650)..(1652)
<223> OTHER INFORMATION: TGA(stop codon)
<220> FEATURE:
<221> NAME/KEY: misc_feature
<222> LOCATION: (1653)..(1660)
<223> OTHER INFORMATION: PmeI restriction site
```

<400> SEQUENCE: 56

| | |
|---|---|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caatgtaat aaaagtatca acaaaaaatt gttaatatac | 420 |
| ctctatactt taacgtcaag gagaaaaaac cccggatcgg actactagca gctgtaatac | 480 |

```
gactcactat agggaatatt aagctaattc tacttcatac attttcaatt aagatgcagt    540
tacttcgctg ttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcggggc ctcggaggag    960 gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccgta ctgatttac tttgaccatt tcatccttgc   1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gttttttgaat   1560 attacaaatc agtaacgttt gtcagtaatt gcggttctca ccctcaaca actagcaaag   1620 gcagccccat aaacacacag tatgttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg ttttcccatg taatatcctt ttctatttt   1800 cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcattttga   2040 cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaagttca cctgtcccac ctgcttctga atcaaacaag gaataaacg   2280 aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa aacatcctcc ttaggttgat   2460
tacgaaacac gccaaccaag tatttcggag tgcctgaact attttatat gcttttacaa   2520 gacttgaaat tttccttgca ataaccgggt caattgttct cttctattg ggcacacata   2580 taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt cttttttcga ccgaatttct tgaagacgaa agggcctcgt   2820
```

```
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tattttatg ttttgtattt ggattttaga aagtaaataa agaaggtaga    3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaggt agtatttgtt    3240 ggcgatcccc ctagagtctt ttacatcttc ggaaaacaaa aactatttt tctttaattt    3300 cttttttac tttctatttt taatttatat atttatatta aaaaatttaa attataatta    3360
tttttatagc acgtgatgaa aaggacccag gtggcacttt tcggggaaat gtgcgcggaa   3420
cccctatttg tttattttc taaatacatt caaatatgta tccgctcatg agacaataac    3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720 gcactttaa agttctgcta tgtggcgcgg tattatcccg tgttgacgcc gggcaagagc    3780
aactcggtcg ccgcatacac tattctcaga atgacttggt tgagtactca ccagtcacag   3840
aaaagcatct tacggatggc atgacagtaa gagaattatg cagtgctgcc ataaccatga   3900
gtgataacac tgcggccaac ttacttctga acaacgatcgg aggaccgaag gagctaaccg   3960
cttttttgca acatgggg gatcatgtaa ctcgccttga tcgttgggaa ccggagctga    4020
atgaagccat accaaacgac gagcgtgaca ccacgatgcc tgtagcaatg caacaacgt     4080 tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
tgtcagacca agtttactca tatatacttt agattgattt aaaacttcat ttttaattta   4440
aaaggatcta ggtgaagatc cttttttgata atctcatgac caaaatccct taacgtgagt   4500
tttcgttcca ctgagcgtca gaccccgtag aaaagatcaa aggatcttct tgagatcctt   4560 ttttttctgcg cgtaatctgc tgcttgcaaa caaaaaaacc accgctacca gcggtggttt   4620
gtttgccgga tcaagagcta ccaactcttt ttccgaaggt aactggcttc agcagagcgc   4680
agataccaaa tactgtcctt ctagtgtagc cgtagttagg ccaccacttc aagaactctg   4740
tagcaccgcc tacatacctc gctctgctaa tcctgttacc agtggctgct gccagtggcg   4800
ataagtcgtg tcttaccggg ttggactcaa gacgatagtt accggataag gcgcagcggt   4860
cgggctgaac ggggggttcg tgcacacagc ccagcttgga gcgaacgacc tacaccgaac   4920
tgagatacct acagcgtgag cattgagaaa gcgccacgct tcccgaaggg agaaaggcgg   4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat   5100
ttttgtgatg ctcgtcaggg gggcgagcc tatggaaaaa cgccagcaac gcggcctttt    5160
tacggttcct ggccttttgc tggccttttg ctcacatgtt ctttcctgcg ttatcccctg   5220
```

```
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtacacgt tcggacaggg taccaaggtg    420
gagatcaaac gtacg                                                     435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgggcagtc ctacagccgt ccgctcacgt tcggacaggg taccaaggtg    420
```

```
gagatcaaac gtacg                                                     435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-3 clone)

<400> SEQUENCE: 60

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca gtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy chain of huAbF46-H4-A1, U6-HC7 hinge and constant region of human IgG1)

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
```

```
                50                  55                  60
Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
                115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460

<210> SEQ ID NO 63
```

<211> LENGTH: 1410
<212> TYPE: DNA
<213> ORGANISM: Artificial Sequence
<220> FEATURE:
<223> OTHER INFORMATION: Synthetic (polynucleotide encoding polypeptide
consisting of heavy chain of huAbF46-H4-A1, U6-HC7 hinge and
constant region of human IgG1)

<400> SEQUENCE: 63

| | | | | |
|---|---|---|---|---|
| gaattcgccg | ccaccatgga | atggagctgg | gttttctcg | taacactttt aaatggtatc | 60 |
| cagtgtgagg | ttcagctggt | ggagtctggc | ggtggcctgg | tgcagccagg gggctcactc | 120 |
| cgtttgtcct | gtgcagcttc | tggcttcacc | ttcactgatt | actacatgag ctgggtgcgt | 180 |
| caggccccgg | gtaagggcct | ggaatggttg | gttttatta | gaaacaaagc taatggttac | 240 |
| acaacagagt | acagtgcatc | tgtgaagggt | cgtttcacta | agcagaga taattccaaa | 300 |
| aacacactgt | acctgcagat | gaacagcctg | cgtgctgagg | acactgccgt ctattattgt | 360 |
| gctagagata | ctggtttgc | ttactggggc | aagggactc | tggtcaccgt ctcctcggct | 420 |
| agcaccaagg | gcccatcggt | cttccccctg | gcaccctcct | ccaagagcac ctctgggggc | 480 |
| acagcggccc | tgggctgcct | ggtcaaggac | tacttcccg | aaccggtgac ggtgtcgtgg | 540 |
| aactcaggcg | ccctgaccag | cggcgtgcac | accttcccgg | ctgtcctaca gtcctcagga | 600 |
| ctctactccc | tcagcagcgt | ggtgaccgtg | ccctccagca | gcttgggcac ccagacctac | 660 |
| atctgcaacg | tgaatcacaa | gcccagcaac | accaaggtgg | acaagaaagt tgagcccaaa | 720 |
| agctgcgatt | gccactgtcc | tccatgtcca | gcacctgaac | tcctgggggg accgtcagtc | 780 |
| ttcctcttcc | ccccaaaacc | caaggacacc | ctcatgatct | cccggacccc tgaggtcaca | 840 |
| tgcgtggtgg | tggacgtgag | ccacgaagac | cctgaggtca | agttcaactg gtacgtggac | 900 |
| ggcgtggagg | tgcataatgc | caagacaaag | ccgcgggagg | agcagtacaa cagcacgtac | 960 |
| cgtgtggtca | gcgtcctcac | cgtcctgcac | caggactggc | tgaatggcaa ggagtacaag | 1020 |
| tgcaaggtct | ccaacaaagc | cctcccagcc | ccatcgaga | aaaccatctc caaagccaaa | 1080 |
| gggcagcccc | gagaaccaca | ggtgtacacc | ctgcccccat | cccgggagga gatgaccaag | 1140 |
| aaccaggtca | gcctgacctg | cctggtcaaa | ggcttctatc | ccagcgacat cgccgtggag | 1200 |
| tgggagagca | atgggcagcc | ggagaacaac | tacaagacca | cgcctcccgt gctggactcc | 1260 |
| gacggctcct | tcttcctcta | cagcaagctc | accgtggaca | agagcaggtg gcagcagggg | 1320 |
| aacgtcttct | catgctccgt | gatgcatgag | gctctgcaca | accactacac gcagaagagc | 1380 |
| ctctcccctgt | ctccgggtaa | atgactcgag | | | 1410 |

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
chain of huAbF46-H4-A1, human IgG2 hinge and constant region
of human IgG1)

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

-continued

```
Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, human IgG2 hinge and constant region of human IgG1)

<400> SEQUENCE: 65

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg gtttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactgggc caagggactc tggtcaccgt ctcctcggct   420
agcaccaagg gcccatcggt cttccccctg gcaccctcct ccaagagcac ctctggggc    480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagaggaag   720
tgctgtgtgg agtgcccccc ctgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggaggagat gaccaagaac  1140
caggtcagcc tgacctgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy chain of huAbF46-H4-A1, human IgG2 hinge and constant region of human IgG2)

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45
```

```
Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, human IgG2 hinge and constant region of human IgG2)

<400> SEQUENCE: 67

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggtttttatta gaaacaaagc taatggttac   240
acaacagagt acagtgcatc tgtgaagggt cgtttcacta agcagaga taattccaaa    300
aacacactgt acctgcagat gaacagcctg cgtgctgagg acactgccgt ctattattgt   360
gctagagata actggtttgc ttactgggc aagggactc tggtcaccgt ctcctcggct    420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca cttcggcac ccagacctac    660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa acccaagga caccctcatg atctcccgga cccctgaggt cacgtgcgtg    840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caagggcag   1080
ccccgagaac acaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacgcctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaatgact cgag                                         1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light chain of huAbF46-H4-A1(H36Y) and human kappa constant region)

<400> SEQUENCE: 68

Met Asp Ser Gln Ala Gln Val Leu Met Leu Leu Leu Leu Ser Val Ser
1               5                   10                  15
Gly Thr Cys Gly Asp Ile Gln Met Thr Gln Ser Pro Ser Ser Leu Ser
                20                  25                  30
Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
        50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and human kappa
      constant region)

<400> SEQUENCE: 69
aattcactag tgattaattc gccgccacca tggattcaca ggcccaggtc tcatgttgc      60 tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                            758

<210> SEQ ID NO 70
<211> LENGTH: 240
<212> TYPE: PRT

<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

Met Asp Ser Gln Ala Gln Val Leu Met Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Gln Ser
        35                  40                  45

Leu Leu Ala Ser Gly Asn Gln Asn Asn His Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain of nti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag aaaggcact tgagtggttg gttttatta gaaacaaagc taatggttac      240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata ctggtttgc ttactgggc caagggactc tggtcactgt ctctgcagct     420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
```

```
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(90)
<223> OTHER INFORMATION: signal sequence
<220> FEATURE:
<221> NAME/KEY: misc_feature
<222> LOCATION: (91)..(432)
<223> OTHER INFORMATION: VL - light chain variable region
<220> FEATURE:
<221> NAME/KEY: misc_feature
<222> LOCATION: (430)..(435)
<223> OTHER INFORMATION: BsiWI restriction site
<220> FEATURE:
<221> NAME/KEY: misc_feature
<222> LOCATION: (433)..(750)
<223> OTHER INFORMATION: CL - light chain constant region
<220> FEATURE:
<221> NAME/KEY: misc_feature
<222> LOCATION: (751)..(753)
<223> OTHER INFORMATION: stop codon
<220> FEATURE:
<221> NAME/KEY: misc_feature
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg    60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 78

<211> LENGTH: 4170
<212> TYPE: DNA
<213> ORGANISM: Artificial Sequence
<220> FEATURE:
<223> OTHER INFORMATION: Synthetic (polynucleotide encoding c-Met protein)

<400> SEQUENCE: 78

| | | | | | |
|---|---|---|---|---|---|
| atgaaggccc | ccgctgtgct | tgcacctggc | atcctcgtgc | tcctgtttac | cttggtgcag | 60 |
| aggagcaatg | gggagtgtaa | agaggcacta | gcaaagtccg | agatgaatgt | gaatatgaag | 120 |
| tatcagcttc | ccaacttcac | cgcggaaaca | cccatccaga | atgtcattct | acatgagcat | 180 |
| cacattttcc | ttggtgccac | taactacatt | tatgttttaa | atgaggaaga | ccttcagaag | 240 |
| gttgctgagt | acaagactgg | gcctgtgctg | aacacccag | attgttccc | atgtcaggac | 300 |
| tgcagcagca | aagccaattt | atcaggaggt | gtttggaaag | ataacatcaa | catggctcta | 360 |
| gttgtcgaca | cctactatga | tgatcaactc | attagctgtg | gcagcgtcaa | cagagggacc | 420 |
| tgccagcgac | atgtctttcc | ccacaatcat | actgctgaca | tacagtcgga | ggttcactgc | 480 |
| atattctccc | cacagataga | agagcccagc | cagtgtcctg | actgtgtggt | gagcgccctg | 540 |
| ggagccaaag | tccttttcatc | tgtaaaggac | cggttcatca | acttctttgt | aggcaatacc | 600 |
| ataaattctt | cttatttccc | agatcatcca | ttgcattcga | tatcagtgag | aaggctaaag | 660 |
| gaaacgaaag | atggttttat | gttttttgacg | gaccagtcct | acattgatgt | tttacctgag | 720 |
| ttcagagatt | cttaccccat | taagtatgtc | catgcctttg | aaagcaacaa | ttttatttac | 780 |
| ttcttgacgg | tccaaaggga | aactctagat | gctcagactt | tcacacaag | aataatcagg | 840 |
| ttctgttcca | taaactctgg | attgcattcc | tacatggaaa | tgcctctgga | gtgtattctc | 900 |
| acagaaaaga | gaaaaagag | atccacaaag | aaggaagtgt | ttaatatact | tcaggctgcg | 960 |
| tatgtcagca | agcctggggc | ccagcttgct | agacaaatag | gagccagcct | gaatgatgac | 1020 |
| attcttttcg | gggtgttcgc | acaaagcaag | ccagattctg | ccgaaccaat | ggatcgatct | 1080 |
| gccatgtgtg | cattccctat | caaatatgtc | aacgacttct | tcaacaagat | cgtcaacaaa | 1140 |
| aacaatgtga | gatgtctcca | gcattttac | ggacccaatc | atgagcactg | ctttaatagg | 1200 |
| acacttctga | gaaattcatc | aggctgtgaa | gcgcgccgtg | atgaatatcg | aacagagttt | 1260 |
| accacagctt | tgcagcgcgt | tgacttattc | atgggtcaat | tcagcgaagt | cctcttaaca | 1320 |
| tctatatcca | ccttcattaa | aggagacctc | accatagcta | atcttgggac | atcagagggt | 1380 |
| cgcttcatgc | aggttgtggt | ttctcgatca | ggaccatcaa | cccctcatgt | gaattttctc | 1440 |
| ctggactccc | atccagtgtc | tccagaagtg | attgtggagc | atacattaaa | ccaaaatggc | 1500 |
| tacacactgg | ttatcactgg | gaagaagatc | acgaagatcc | cattgaatgg | cttgggctgc | 1560 |
| agacatttcc | agtcctgcag | tcaatgcctc | tctgccccac | cctttgttca | gtgtggctgg | 1620 |
| tgccacgaca | aatgtgtgcg | atcggaggaa | tgcctgagcg | ggacatggac | tcaacagatc | 1680 |
| tgtctgcctg | caatctacaa | ggttttccca | aatagtgcac | ccttgaagg | agggacaagg | 1740 |
| ctgaccatat | gtggctggga | ctttggattt | cggaggaata | taaatttga | tttaaagaaa | 1800 |
| actagagttc | tccttggaaa | tgagagctgc | accttgactt | taagtgagag | cacgatgaat | 1860 |
| acattgaaat | gcagttggg | tcctgccatg | aataagcatt | caatatgtc | cataattatt | 1920 |
| tcaaatggcc | acgggacaac | acaatacagt | acattctcct | atgtggatcc | tgtaataaca | 1980 |
| agtatttcgc | cgaaatacgg | tcctatggct | ggtggcactt | tacttacttt | aactggaaat | 2040 |
| tacctaaaca | gtgggaattc | tagacacatt | tcaattggtg | gaaaaacatg | tactttaaaa | 2100 |

| | |
|---|---|
| agtgtgtcaa acagtattct tgaatgttat accccagccc aaaccatttc aactgagttt | 2160 |
| gctgttaaat tgaaaattga cttagccaac cgagagacaa gcatcttcag ttaccgtgaa | 2220 |
| gatcccattg tctatgaaat tcatccaacc aaatctttta ttagtggtgg gagcacaata | 2280 |
| acaggtgttg ggaaaaacct gaattcagtt agtgtcccga gaatggtcat aaatgtgcat | 2340 |
| gaagcaggaa ggaactttac agtggcatgt caacatcgct ctaattcaga gataatctgt | 2400 |
| tgtaccactc cttccctgca acagctgaat ctgcaactcc ccctgaaaac caaagccttt | 2460 |
| ttcatgttag atgggatcct ttccaaatac tttgatctca tttatgtaca taatcctgtg | 2520 |
| tttaagcctt ttgaaaagcc agtgatgatc tcaatgggca tgaaaatgt actggaaatt | 2580 |
| aagggaaatg atattgaccc tgaagcagtt aaaggtgaag tgttaaaagt tggaaataag | 2640 |
| agctgtgaga atatacactt acattctgaa gccgttttat gcacggtccc caatgacctg | 2700 |
| ctgaaattga acagcgagct aaatatagag tggaagcaag caatttcttc aaccgtcctt | 2760 |
| ggaaaagtaa tagttcaacc agatcagaat ttcacaggat tgattgctgg tgttgtctca | 2820 |
| atatcaacag cactgttatt actacttggg ttttcctgt ggctgaaaaa gagaaagcaa | 2880 |
| attaaagatc tgggcagtga attagttcgc tacgatgcaa gagtacacac tcctcatttg | 2940 |
| gataggcttg taagtgcccg aagtgtaagc ccaactacag aaatggtttc aaatgaatct | 3000 |
| gtagactacc gagctacttt tccagaagat cagtttccta attcatctca gaacggttca | 3060 |
| tgccgacaag tgcagtatcc tctgacagac atgtccccca tcctaactag tggggactct | 3120 |
| gatatatcca gtccattact gcaaaatact gtccacattg acctcagtgc tctaaatcca | 3180 |
| gagctggtcc aggcagtgca gcatgtagtg attgggccca gtagcctgat tgtgcatttc | 3240 |
| aatgaagtca taggaagagg gcatttggt tgtgtatatc atgggacttt gttggacaat | 3300 |
| gatggcaaga aaattcactg tgctgtgaaa tccttgaaca gaatcactga cataggagaa | 3360 |
| gtttcccaat ttctgaccga gggaatcatc atgaaagatt ttagtcatcc caatgtcctc | 3420 |
| tcgctcctgg gaatctgcct gcgaagtgaa gggtctccgc tggtggtcct accatacatg | 3480 |
| aaacatggag atcttcgaaa tttcattcga aatgagactc ataatccaac tgtaaaagat | 3540 |
| cttattggct tggtcttca gtagccaaa ggcatgaaat atcttgcaag caaaaagttt | 3600 |
| gtccacagag acttggctgc aagaaactgt atgctggatg aaaaattcac agtcaaggtt | 3660 |
| gctgattttg gtcttgccag agacatgtat gataaagaat actatagtgt acacaacaaa | 3720 |
| acaggtgcaa agctgccagt gaagtggatg gctttggaaa gtctgcaaac tcaaaagttt | 3780 |
| accaccaagt cagatgtgtg gtcctttggc gtgctcctct gggagctgat gacaagagga | 3840 |
| gccccacctt atcctgacgt aaacaccttt gatataactg tttacttgtt gcaagggaga | 3900 |
| agactcctac aacccgaata ctgcccagac cccttatatg aagtaatgct aaaatgctgg | 3960 |
| caccctaaag ccgaaatgcg cccatccttt tctgaactgg tgtcccggat atcagcgatc | 4020 |
| ttctctactt tcattgggga gcactatgtc catgtgaacg ctacttatgt gaacgtaaaa | 4080 |
| tgtgtcgctc cgtatccttc tctgttgtca tcagaagata cgctgatga tgaggtggac | 4140 |
| acacgaccag cctccttctg ggagacatca | 4170 |

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

-continued

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415
```

```
Ser Thr Pro His Val Asn Phe Leu Leu Asp Ser His Pro Val Ser Pro
                420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
 1               5                  10                  15

Gly Leu Gly Cys Arg His Phe Gln Ser Cys Ser Gln Cys Leu Ser Ala
             20                  25                  30

Pro Pro Phe Val Gln Cys Gly Trp Cys His Asp Lys Cys Val Arg Ser
             35                  40                  45

Glu Glu Cys Leu Ser Gly Thr Trp Thr Gln Gln Ile Cys Leu Pro Ala
         50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335
```

```
Ala Phe Phe Met Leu Asp Gly Ile Leu Ser Lys Tyr Phe Asp Leu Ile
                340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
        370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Gly Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240
```

```
Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa gtcctttca tctgtaaagg accggttcat caacttctca     420
gtaggcaata ccataaattc ttcttatttc ccagatcatc cattgcattc gatatcagtg     480
agaaggctaa aggaaacgaa agatggtttt atgttttga cggaccagtc ctacattgat     540
gttttacctg agttcagaga ttcttacccc attaagtatg ccatgccttt gaaagcaac      600 aatttttatt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccctcat     1260 gtgaattttc tcctggactc ccatccagtg tctccagaag tgattgtgga gcatacatta    1320
aaccaaaatg gc                                                        1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
``` domain of c-Met)

<400> SEQUENCE: 83

| tacacactgg | ttatcactgg | gaagaagatc | acgaagatcc | cattgaatgg | cttgggctgc | 60 |
| agacatttcc | agtcctgcag | tcaatgcctc | tctgccccac | cctttgttca | gtgtggctgg | 120 |
| tgccacgaca | aatgtgtgcg | atcggaggaa | tgcctgagcg | ggacatggac | tcaacagatc | 180 |
| tgtctgcctg | caatctacaa | ggttttccca | aatagtgcac | cccttgaagg | agggacaagg | 240 |
| ctgaccatat | gtggctggga | ctttggattt | cggaggaata | taaatttga | tttaaagaaa | 300 |
| actagagttc | tccttggaaa | tgagagctgc | accttgactt | taagtgagag | cacgatgaat | 360 |
| acattgaaat | gcacagttgg | tcctgccatg | aataagcatt | tcaatatgtc | cataattatt | 420 |
| tcaaatggcc | acgggacaac | acaatacagt | acattctcct | atgtggatcc | tgtaataaca | 480 |
| agtatttcgc | cgaaatacgg | tcctatggct | ggtggcactt | tacttacttt | aactggaaat | 540 |
| tacctaaaca | gtgggaattc | tagacacatt | tcaattggtg | gaaaaacatg | tactttaaaa | 600 |
| agtgtgtcaa | acagtattct | tgaatgttat | accccagccc | aaaccatttc | aactgagttt | 660 |
| gctgttaaat | tgaaaattga | cttagccaac | cgagagacaa | gcatcttcag | ttaccgtgaa | 720 |
| gatcccattg | tctatgaaat | tcatccaacc | aaatctttta | ttagtggtgg | gagcacaata | 780 |
| acaggtgttg | ggaaaaacct | gaattcagtt | agtgtcccga | gatggtcat | aaatgtgcat | 840 |
| gaagcaggaa | ggaactttac | agtggcatgt | caacatcgct | ctaattcaga | gataatctgt | 900 |
| tgtaccactc | cttccctgca | acagctgaat | ctgcaactcc | ccctgaaaac | caaagccttt | 960 |
| ttcatgttag | atgggatcct | ttccaaatac | tttgatctca | tttatgtaca | taatcctgtg | 1020 |
| tttaagcctt | ttgaaaagcc | agtgatgatc | tcaatgggca | atgaaaatgt | actggaaatt | 1080 |
| aagggaaatg | atattgaccc | tgaagcagtt | aaaggtgaag | tgttaaaagt | tggaaataag | 1140 |
| agctgtgaga | atatacactt | acattctgaa | gccgttttat | gcacggtccc | caatgacctg | 1200 |
| ctgaaattga | acagcgagct | aaatatagag | tggaagcaag | caatttcttc | aaccgtcctt | 1260 |
| ggaaaagtaa | tagttcaacc | agatcagaat | ttcacagga | | | 1299 |

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84

| gtgcatttca | atgaagtcat | aggaagaggg | cattttggtt | gtgtatatca | tgggactttg | 60 |
| ttggacaatg | atggcaagaa | aattcactgt | gctgtgaaat | ccttgaacag | aatcactgac | 120 |
| ataggagaag | tttcccaatt | tctgaccgag | ggaatcatca | tgaaagattt | tagtcatccc | 180 |
| aatgtcctct | cgctcctggg | aatctgcctg | cgaagtgaag | ggtctccgct | ggtggtccta | 240 |
| ccatacatga | acatggagag | tcttcgaaat | ttcattcgaa | atgagactca | taatccaact | 300 |
| gtaaagatc | ttattggctt | tggtcttcaa | gtagccaaag | gcatgaaata | tcttgcaagc | 360 |
| aaaaagtttg | tccacagaga | cttggctgca | agaaactgta | tgctggatga | aaaattcaca | 420 |
| gtcaaggttg | ctgattttgg | tcttgccaga | gacatgtatg | ataaagaata | ctatagtgta | 480 |
| cacaacaaaa | caggtgcaaa | gctgccagtg | aagtggatgg | cttttgaaag | tctgcaaact | 540 |
| caaaagttta | ccaccaagtc | agatgtgtgg | tcctttggcg | tgctcctctg | ggagctgatg | 600 |

```
acaagaggag cccccacctta tcctgacgta aacacctttg atataactgt ttacttgttg    660
caagggagaa gactcctaca acccgaatac tgcccagacc ccttatatga agtaatgcta    720
aaatgctggc accctaaagc cgaaatgcgc ccatcctttt ctgaactggt gtcccggata    780
tcagcgatct ctctactttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                           939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT

<213> ORGANISM: Artificial Sequence
<220> FEATURE:
<223> OTHER INFORMATION: Synthetic (light chain ariable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser

-continued

```
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of
```

AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

```
Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of
      AT-Vk2)

<400> SEQUENCE: 97

Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
```

```
                    85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of
      AT-Vk3)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65              70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of
      AT-Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
```

-continued

```
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro Ser
1               5                   10                  15

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 23
<212> TYPE: DNA
<213> ORGANISM: Artificial Sequence
```

```
<220> FEATURE:
<223> OTHER INFORMATION: Synthetic (forward primer for exon 14)

<400> SEQUENCE: 106
tgaaattgaa cagcgagcta aat                                              23

<210> SEQ ID NO 107
<211> LENGTH: 22
<212> TYPE: DNA
<213> ORGANISM: Artificial Sequence
<220> FEATURE:
<223> OTHER INFORMATION: Synthetic (reverse primer for exon 14)

<400> SEQUENCE: 107
ttgaaatgca caatcaggct ac                                               22

<210> SEQ ID NO 108
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 108

Lys Ser Ser Gln Ser Leu Leu Ala Trp Gly Asn Gln Asn Asn Tyr Leu
1               5                   10                  15
Ala

<210> SEQ ID NO 109
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 110
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 110
```

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 111
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 112
<211> LENGTH: 11241
<212> TYPE: DNA
<213> ORGANISM: Artificial Sequence
```

```
<220> FEATURE:
<223> OTHER INFORMATION: Human Cbl gene
<220> FEATURE:
<221> NAME/KEY: CDS
<222> LOCATION: (143)..(2860)

<400> SEQUENCE: 112
tccgcccgga tagccggcgg cggcggcggc ggcggcggcg gcggcggccg ggagaggccc      60
ctccttcacg ccctgcttct ctccctcgct cgcagtcgag ccgagccggc ggacccgcct     120
gggctccgac cctgcccagg cc       atg gcc ggc aac gtg aag aag agc        166
                                Met Ala Gly Asn Val Lys Lys Ser
                                1               5 tct ggg gcc ggg ggc ggc agc ggc tcc ggg ggc tcg ggt tcg ggt ggc        214
Ser Gly Ala Gly Gly Gly Ser Gly Ser Gly Gly Ser Gly Ser Gly Gly
        10                  15                  20 ctg att ggg ctc atg aag gac gcc ttc cag ccg cac cac cac cac cac        262
Leu Ile Gly Leu Met Lys Asp Ala Phe Gln Pro His His His His His
25                  30                  35                  40 cac cac ctc agc ccc cac ccg ccg ggg acg gtg gac aag aag atg gtg        310
His His Leu Ser Pro His Pro Pro Gly Thr Val Asp Lys Lys Met Val
                45                  50                  55 gag aag tgc tgg aag ctc atg gac aag gtg gtg cgg ttg tgt cag aac        358
Glu Lys Cys Trp Lys Leu Met Asp Lys Val Val Arg Leu Cys Gln Asn
            60                  65                  70 cca aag ctg gcg cta aag aat agc cca cct tat atc tta gac ctg cta        406
Pro Lys Leu Ala Leu Lys Asn Ser Pro Pro Tyr Ile Leu Asp Leu Leu
        75                  80                  85 cca gat acc tac cag cat ctc cgt act atc ttg tca aga tat gag ggg        454
Pro Asp Thr Tyr Gln His Leu Arg Thr Ile Leu Ser Arg Tyr Glu Gly
    90                  95                  100 aag atg gag aca ctt gga gaa aat gag tat ttt agg gtg ttt atg gag        502
Lys Met Glu Thr Leu Gly Glu Asn Glu Tyr Phe Arg Val Phe Met Glu
105                 110                 115                 120 aat ttg atg aag aaa act aag caa acc ata agc ctc ttc aag gag gga        550
Asn Leu Met Lys Lys Thr Lys Gln Thr Ile Ser Leu Phe Lys Glu Gly
                125                 130                 135 aaa gaa aga atg tat gag gag aat tct cag cct agg cga aac cta acc        598
Lys Glu Arg Met Tyr Glu Glu Asn Ser Gln Pro Arg Arg Asn Leu Thr
            140                 145                 150 aaa ctg tcc ctc atc ttc agc cac atg ctg gca gaa cta aaa gga atc        646
Lys Leu Ser Leu Ile Phe Ser His Met Leu Ala Glu Leu Lys Gly Ile
        155                 160                 165 ttt cca agt gga ctc ttt cag gga gac aca ttt cgg att act aaa gca        694
Phe Pro Ser Gly Leu Phe Gln Gly Asp Thr Phe Arg Ile Thr Lys Ala
    170                 175                 180 gat gct gcg gaa ttt tgg aga aaa gct ttt ggg gaa aag aca ata gtc        742
Asp Ala Ala Glu Phe Trp Arg Lys Ala Phe Gly Glu Lys Thr Ile Val
185                 190                 195                 200 cct tgg aag agc ttt cga cag gct cta cat gaa gtg cat ccc atc agt        790
Pro Trp Lys Ser Phe Arg Gln Ala Leu His Glu Val His Pro Ile Ser
                205                 210                 215 tct ggg ctg gag gcc atg gct ctg aaa tcc act att gat ctg acc tgc        838
Ser Gly Leu Glu Ala Met Ala Leu Lys Ser Thr Ile Asp Leu Thr Cys
            220                 225                 230 aat gat tat att tcg gtt ttt gaa ttt gac atc ttt acc cga ctc ttt        886
Asn Asp Tyr Ile Ser Val Phe Glu Phe Asp Ile Phe Thr Arg Leu Phe
        235                 240                 245 cag ccc tgg tcc tct ttg ctc agg aat tgg aac agc ctt gct gta act        934
Gln Pro Trp Ser Ser Leu Leu Arg Asn Trp Asn Ser Leu Ala Val Thr
    250                 255                 260
```

```
cat cct ggc tac atg gct ttt ttg acg tat gac gaa gtg aaa gct cgg     982
His Pro Gly Tyr Met Ala Phe Leu Thr Tyr Asp Glu Val Lys Ala Arg
265                 270                 275                 280 ctc cag aaa ttc att cac aaa cct ggc agt tat atc ttc cgg ctg agc    1030
Leu Gln Lys Phe Ile His Lys Pro Gly Ser Tyr Ile Phe Arg Leu Ser
            285                 290                 295 tgt act cgt ctg ggt cag tgg gct att ggg tat gtt act gct gat ggg    1078
Cys Thr Arg Leu Gly Gln Trp Ala Ile Gly Tyr Val Thr Ala Asp Gly
                300                 305                 310 aac att ctc cag aca atc cct cac aat aaa cct ctc ttc caa gca ctg    1126
Asn Ile Leu Gln Thr Ile Pro His Asn Lys Pro Leu Phe Gln Ala Leu
            315                 320                 325 att gat ggc ttc agg gaa ggc ttc tat ttg ttt cct gat gga cga aat    1174
Ile Asp Gly Phe Arg Glu Gly Phe Tyr Leu Phe Pro Asp Gly Arg Asn
330                 335                 340 cag aat cct gat ctg act ggc tta tgt gaa cca act ccc caa gac cat    1222
Gln Asn Pro Asp Leu Thr Gly Leu Cys Glu Pro Thr Pro Gln Asp His
345                 350                 355                 360 atc aaa gtg acc cag gaa caa tat gaa tta tac tgt gag atg ggc tcc    1270
Ile Lys Val Thr Gln Glu Gln Tyr Glu Leu Tyr Cys Glu Met Gly Ser
            365                 370                 375 aca ttc caa cta tgt aaa ata tgt gct gaa aat gat aag gat gta aag    1318
Thr Phe Gln Leu Cys Lys Ile Cys Ala Glu Asn Asp Lys Asp Val Lys
                380                 385                 390 att gag ccc tgt gga cac ctc atg tgc aca tcc tgt ctt aca tcc tgg    1366
Ile Glu Pro Cys Gly His Leu Met Cys Thr Ser Cys Leu Thr Ser Trp
            395                 400                 405 cag gaa tca gaa ggt cag ggc tgt cct ttc tgc cga tgt gaa att aaa    1414
Gln Glu Ser Glu Gly Gln Gly Cys Pro Phe Cys Arg Cys Glu Ile Lys
410                 415                 420 ggt act gaa ccc atc gtg gta gat ccg ttt gat cct aga ggg agt ggc    1462
Gly Thr Glu Pro Ile Val Val Asp Pro Phe Asp Pro Arg Gly Ser Gly
425                 430                 435                 440 agc ctg ttg agg caa gga gca gag gga gct ccc tcc cca aat tat gat    1510
Ser Leu Leu Arg Gln Gly Ala Glu Gly Ala Pro Ser Pro Asn Tyr Asp
            445                 450                 455 gat gat gat gat gaa cga gct gat gat act ctc ttc atg atg aag gaa    1558
Asp Asp Asp Asp Glu Arg Ala Asp Asp Thr Leu Phe Met Met Lys Glu
                460                 465                 470 ttg gct ggt gcc aag gtg gaa cgg ccg cct tct cca ttc tcc atg gcc    1606
Leu Ala Gly Ala Lys Val Glu Arg Pro Pro Ser Pro Phe Ser Met Ala
            475                 480                 485 cca caa gct tcc ctt ccc ccg gtg cca cca cga ctt gac ctt ctg ccg    1654
Pro Gln Ala Ser Leu Pro Pro Val Pro Pro Arg Leu Asp Leu Leu Pro
490                 495                 500 cag cga gta tgt gtt ccc tca agt gct tct gct ctt gga act gct tct    1702
Gln Arg Val Cys Val Pro Ser Ser Ala Ser Ala Leu Gly Thr Ala Ser
505                 510                 515                 520 aag gct gct tct ggc tcc ctt cat aaa gac aaa cca ttg cca gta cct    1750
Lys Ala Ala Ser Gly Ser Leu His Lys Asp Lys Pro Leu Pro Val Pro
            525                 530                 535 ccc aca ctt cga gat ctt cca cca ccg cct cca gac cgg cca tat        1798
Pro Thr Leu Arg Asp Leu Pro Pro Pro Pro Pro Asp Arg Pro Tyr
                540                 545                 550 tct gtt gga gca gaa tcc cga cct caa aga cgc ccc ttg cct tgt aca    1846
Ser Val Gly Ala Glu Ser Arg Pro Gln Arg Arg Pro Leu Pro Cys Thr
            555                 560                 565 cca ggc gac tgt ccc tcc aga gac aaa ctg ccc cct gtc ccc tct agc    1894
Pro Gly Asp Cys Pro Ser Arg Asp Lys Leu Pro Pro Val Pro Ser Ser
```

```
                570                  575                  580
cgc ctt gga gac tca tgg ctg ccc cgg cca atc ccc aaa gta cca gta    1942
Arg Leu Gly Asp Ser Trp Leu Pro Arg Pro Ile Pro Lys Val Pro Val
585                  590                  595                  600 tct gcc cca agt tcc agt gat ccc tgg aca gga aga gaa tta acc aac    1990
Ser Ala Pro Ser Ser Ser Asp Pro Trp Thr Gly Arg Glu Leu Thr Asn
                605                  610                  615 cgg cac tca ctt cca ttt tca ttg ccc tca caa atg gag ccc aga cca    2038
Arg His Ser Leu Pro Phe Ser Leu Pro Ser Gln Met Glu Pro Arg Pro
            620                  625                  630 gat gtg cct agg ctc gga agc acg ttc agt ctg gat acc tcc atg agt    2086
Asp Val Pro Arg Leu Gly Ser Thr Phe Ser Leu Asp Thr Ser Met Ser
        635                  640                  645 atg aat agc agc cca tta gta ggt cca gag tgt gac cac ccc aaa atc    2134
Met Asn Ser Ser Pro Leu Val Gly Pro Glu Cys Asp His Pro Lys Ile
650                  655                  660 aaa cct tcc tca tct gcc aat gcc att tat tct ctg gct gcc aga cct    2182
Lys Pro Ser Ser Ser Ala Asn Ala Ile Tyr Ser Leu Ala Ala Arg Pro
665                  670                  675                  680 ctt cct gtg cca aaa ctg cca cct ggg gag caa tgt gag ggt gaa gag    2230
Leu Pro Val Pro Lys Leu Pro Pro Gly Glu Gln Cys Glu Gly Glu Glu
                685                  690                  695 gac aca gag tac atg act ccc tct tcc agg cct cta cgg cct ttg gat    2278
Asp Thr Glu Tyr Met Thr Pro Ser Ser Arg Pro Leu Arg Pro Leu Asp
            700                  705                  710 aca tcc cag agt tca cga gca tgt gat tgc gac cag cag att gat agc    2326
Thr Ser Gln Ser Ser Arg Ala Cys Asp Cys Asp Gln Gln Ile Asp Ser
        715                  720                  725 tgt acg tat gaa gca atg tat aat att cag tcc cag gcg cca tct atc    2374
Cys Thr Tyr Glu Ala Met Tyr Asn Ile Gln Ser Gln Ala Pro Ser Ile
730                  735                  740 acc gag agc agc acc ttt ggt gaa ggg aat ttg gcc gca gcc cat gcc    2422
Thr Glu Ser Ser Thr Phe Gly Glu Gly Asn Leu Ala Ala Ala His Ala
745                  750                  755                  760 aac act ggt ccc gag gag tca gaa aat gag gat gat ggg tat gat gtc    2470
Asn Thr Gly Pro Glu Glu Ser Glu Asn Glu Asp Asp Gly Tyr Asp Val
                765                  770                  775 cca aag cca cct gtg ccg gcc gtg ctg gcc cgc cga act ctc tca gat    2518
Pro Lys Pro Pro Val Pro Ala Val Leu Ala Arg Arg Thr Leu Ser Asp
            780                  785                  790 atc tct aat gcc agc tcc tcc ttt ggc tgg ttg tct ctg gat ggt gat    2566
Ile Ser Asn Ala Ser Ser Ser Phe Gly Trp Leu Ser Leu Asp Gly Asp
        795                  800                  805 cct aca aca aat gtc act gaa ggt tcc caa gtt ccc gag agg cct cca    2614
Pro Thr Thr Asn Val Thr Glu Gly Ser Gln Val Pro Glu Arg Pro Pro
810                  815                  820 aaa cca ttc ccg cgg aga atc aac tct gaa cgg aaa gct ggc agc tgt    2662
Lys Pro Phe Pro Arg Arg Ile Asn Ser Glu Arg Lys Ala Gly Ser Cys
825                  830                  835                  840 cag caa ggt agt ggt cct gcc gcc tct gct gcc acc gcc tca cct cag    2710
Gln Gln Gly Ser Gly Pro Ala Ala Ser Ala Ala Thr Ala Ser Pro Gln
                845                  850                  855 ctc tcc agt gag atc gag aac ctc atg agt cag ggg tac tcc tac cag    2758
Leu Ser Ser Glu Ile Glu Asn Leu Met Ser Gln Gly Tyr Ser Tyr Gln
            860                  865                  870 gac atc cag aaa gct ttg gtc att gcc cag aac aac atc gag atg gcc    2806
Asp Ile Gln Lys Ala Leu Val Ile Ala Gln Asn Asn Ile Glu Met Ala
        875                  880                  885 aaa aac atc ctc cgg gaa ttt gtt tcc att tct tct cct gcc cat gta    2854
```

```
Lys Asn Ile Leu Arg Glu Phe Val Ser Ile Ser Ser Pro Ala His Val
    890                 895                 900 gct acc   tagcacacca tctccctgct gcaggtttag aggaccagtg agttgggagt   2910
Ala Thr
905 tattactcaa gtggcaccta aagggcagg agttcctttg gtgacttcac agtgaagtct   2970 tgccctctct gtgggatatc acatcagtgg ttccaagatt tcaaagtggt gaaatgaaaa   3030 tggagcagct agtatgtttt attatttat gggtcttgag tgcatttgaa ggtgtccttc   3090 agttcccacg tagagagagt gtggattata ttacatgata acctacctgg ggaacagtcc   3150 agaaagctat agaacaagta ttttgctgga aatcctaatt gaggacttaa gacttcctgg   3210 gttaaggatg tggccgtgtg tgtgtgtgtc tgcctgtggt tgtatgtgtc cttgtgatta   3270 taagattaac ctgctgtgtg tgttaattcc aggcagggaa ttagcacaaa aggtttagga   3330 aggaatcttt ttttaaagac ttccatctac tgtggtatta tacccaagcc tagtgtgtat   3390 tacaacttca acactcccct ttggcttata ttaccatgtg catagctaaa gtcttctatt   3450 tttagaacac cttctgtctg ttctttcccc atcaactcct tcctcatcct tcttggtgtt   3510 ctgtcatggg ccatgggctt gctatggcca gccttactga ggccaagcag cttatgggat   3570 gttctttatt gtgtgtgatg gtattggttt gtttggtaga taagtgggag gaaaagtact   3630 gttgctacac tattataggc atgtttgata ctagcagcta acactggtca ctccaaagca   3690 ctgtttctat aggaacattg aagctattaa gatgttttga ttatcctaat tacataatga   3750 ccgatttgag atagaggcct ttaaatacat tccatgccct ccccagaaaa tagtctgtgg   3810 gagtcagttg ccttggtgcc aggtatgtgt tctgatgtag gtcatgagtc tttctactta   3870 atgggaaggg aagaacattt gtttccagga tgactttctg gccagaatac cggaaagctt   3930 ttaggaagct tcgttcacat gctatttaaa tgcacaaaat agacagtaag gatttatctg   3990 ttcagttttt cttcccagtg aattaatttc agcttatatg ggtgtcttca tttgaacatg   4050 aggaatatta ggttatattt tcagcagtgg ttttttcctt tgcccttta ggagtgggga   4110 taatgtccac ggtggcccag cctcttgctg atggcacctt ccctgcattg ctgcctcccg   4170 atgatgtggt tcttttcttg tgcctgtggc tttgggaatg taacatctct ttcctccttt   4230 ccttcccttt tcctcttcac ctgaggtcct aaatactctc tgtaattact gtgttcttca   4290 cggtaattag acatcattca gtgaataaat tactgtagtc aaagacagta tgggctggca   4350 gtttgtgtaa ttgcaagttc ataaagagaa ttgagggtcc agttgggaga actattagtc   4410 agttctttta tatgctgata aatgatccct cgagttcagt tagtattctg tccagagtgt   4470 ttagctcact ttcttagcag tgtgtaagct ttctccatgt cagaagcaag cctgctcttt   4530 gataaatctg tcttcctgaa aatctaaatc atgcttttgt ctttagatct acacagaaat   4590 gaccctcctt ggatcagttt tctttccagt ctaatcatct ttggaactaa aacttgttct   4650 aactcgtctc ttggcattca gctactccta gatcttttgg ttttatcccc tggcctcaga   4710 gccatttata ttcccagagt aggcagtaca ggatctcgtg ttgatttgct gtggttaccc   4770 agtgtcttct ctacatggca taaagcggca aagcccacca ttaggtgagg cggtcccgag   4830 ttgaggtaga gtggggcaga ggaagatggc agtgaatatc aaacagtaga ccgccatcaa   4890 cttctaacag ccagtacaca cactgtttca ttttgaggta acgttcagtt ttgcattttg   4950 tttaaatatt gaaggcctag acaaagaact agaaaaaaaa aagcagtttc caggcccatc   5010 catattgtaa tttttcttta tctgcagata ttgcctgtag tctaaagatc tctttggaag   5070
```

```
acaaagcatt ggctatatat cttttgcctt ttccatgcat ctaaatcttc tctggagatt    5130
atctccctac tgtgtaggtt aagggcagtc tcgactttc cttttttgag tcctgtgtgg    5190
ctctttgaat cagcgtgaaa ctgaggctcc agctccctgt gttgtgtgtg tgtgccatcc    5250
atgggcttgg gtgtcagttt gtcacaggta tctgccagca ttcaaggttt tggatcattt    5310
catgaggatc tttcctttga ctgggtgctg tgaggacaca cctgggtctg tgcctgagat    5370
tgccaggcaa gattaaggaa agttttcatg tggcttttgt tttgaggtta ttctcaaaac    5430
cttaatttct tatattttct gttgactaag gcaccagtaa cccattcttc accctccatt    5490
tgtatggcaa tttaaaagtc tttggctttg ctctgaattt aattaaaact gccttttatg    5550
aacagacttc gagttttgcc attttgggca agcccttccg cttgtccctt cctagtggct    5610
aataaagtaa aaaacccac actactttgt tctcttttc tcatattcat tgggctgttg      5670
tattcagcca gtctcatgct ttccctgggt cttcacggat tgctttccaa gctgccttgt    5730
tgcggggttg ctgcagagca gcaactggac cttttccagct gtcgccatgt tccttccact    5790
aaagtagagg gttcttaaaa tggaaaaacc tgtgggctct tcatatacct ccctttagtt    5850
aagtaataga ccaggcagct tctcatctca gcatttaccct gttaatattt ttgtgaatag   5910
tgctctctac ctgtgggtgg ccgttctctt ccacttgctc gtctccccc agccccattc     5970 tgcataatct accattcttc tcctctcttt ctcttcttat acagaccctc attactgggg    6030
cccaagatgt gggatactac tgttagtatt atttaactat tttgtagatt taaaagattt    6090
ctggttaagg gaggtggggg tcactgttca tcactcttaa aatatgtgtt ttctctatag    6150
aaaagtaaaa tgtgttatg gtcccaaaca gtcaactcac aaatttttat aacaaaattt     6210
ccttgtaaaa actagggacc atctatatat tcccttaag atctagttct ttttgtaggt     6270
gttcagcaat ggtgataaag cagaatattc tcctacctca cgtcattaaa gtcagaagat    6330
tatagacctt ctcaaactat aagtccctct tcttgccgtt ggcctttctg actctggaat    6390
gaccactgtt cattgaaaaa tagttttctg actattggtc tggctctaac agtttgtttg    6450
ttcatccagc aaatgtttat gagtgatgac catgtgccag aaatgtcagg tatgtgtcct    6510
tcccttggcg ccacatagta gtttactaat gtttggggga ttgtacttgg actgtcatag    6570
cctctgcgtt tgaccttaaa atagctcttc ccagtaagat tgtgcaattt ttattcacag    6630
ctcttccatg tagacttacc tttcctcata gagctatcct ggttaataac aggccaagat    6690
tctcccatta tcccctgttg tctcctgtag ctttgataat gcctgggaga ttccttggtg    6750
taagtgtcat ggataccgac tgttttatg ttggaatttg ttccaacata attagaatct     6810
gtttggtgag ttgaaaggta agttggctca gagttgcaca gtagggcatt aaatgtttaa    6870
gcaaagcatc tgcccacact ccccttcca atctagtgcc ttccttgaac tttttcctga     6930
gctgctacgt ccctaatccc ccttgtggg aggattttcg tatcacccctt atgggacctg    6990 tcaccatgtc ctgtactatt tggaattggt tttccagtct ttcaacaacc gttgtggcta    7050
actatgtttt agaagggctg gaggtgtggg ccctgtcttc gggtctcagg acccaaagat    7110
cctttagtca gttgttgggt cttccaagag ccagacatta atacagattg aactccatca    7170
gtcccctaat tgtcagcctt tacctccctc ccagagcaag gagtttaggg attctaaagc    7230
ttagtgtcca cacatcattc taccagacct tagagctta gaagctcaat ctaaaatact    7290
gtaactcagc ataaactatt actatcactc ctttgaactc agtctccatg agcagtgttt    7350
tgttggaaat acatagaacg gcttaatgcc tagagggtgg tggatagtga aggacggtca    7410
aggttatatt tttgactgct tagggattct ttggatccaa gaaacagaaa tgttcaagcg    7470
```

```
gaataaagga gggagtggag ttgtggtaag gatgcagggt atttcgcaga acccaggacg    7530
ggaagtgcct ttggttcttg ggtggagctg gaactgcaga gctttgcacc tagtcctttc    7590
tcccgcttca cagtctgctt atggtatatg tggcccccaa ataggcactc tagtcctcaa    7650
gtctacacca ccttccaact ctggggatca ccatgaacaa attctcaatt tcccatactt    7710 aattttttt ttttttgaga tggagtctcg ctgtgtcgcc caggctggag tgcagtggtg    7770
cagtctcaac tcaccacaac ctctgcctcc caggttcaag cagttctctg cctcaacctc    7830
ccgagtagct gggattacag gcgcctgcca ccatgcccag ctaatgttca tattttagt    7890 agagacaggg tttcaccgtc ttggctaggc tggtcttgaa ctcctgaccc tcatgatcca    7950
cccacctcgg cctcccaaag tgctaagatt acaggcgtga gccaccgcgc ccggcccata    8010
cttcgtattc ttaaaaaaaa ctacactcag cccagcacat tgatcaagta tctatctctg    8070
agcagttggc cttgccaggg agagcagaga tgtggcaggc tccttcagct ggagacaggg    8130
agcttctcag agaagtgagc agagactcca cagacaccct aaaaaggctt ctactcaaga    8190
agtaaagcca ctactcctgc cttttgctt agtggacagg aaggcacagg agtttgtctg    8250
ggacatcata gaaattctta ggtttaactt aattctggtc attgtcttct ttatttcctg    8310
tttttcttcc ctttgtcagt cttcgcatcc aagatttctt ccctccctct tgtgggccag    8370
cctgtcctgt tccagagcta gcctgttcct gggtagcctt ccttagcctc cattcagcct    8430
caggtctttt gccttcttcc gtgtttattt agagagcaga atctaataac gggttccact    8490
gtagccacta tccatggact tctgggtcct cttcaggttt gagtgcttga aaatgttcat    8550
tctctgggct tgtggcctgt ctcctccact ctcctcctca ccctctcgct ccttcctgtg    8610
tgagggccgc tctgcagtaa tgttctcagg caagccttcc taggcacctc agaaactact    8670
ttgccagagc cagtaagaat atataatatt ggagcagttg ccaggataga aattaaatat    8730
agattccagt ttaggataga gttttaccg agagctcttt agacagtata cctgtgtctt    8790
ctctggcaat tgctttcatt ttagtcctat ataaaagctt tccttttctg tttttttta    8850 aaactatgct tttgcttgcc taaatctttt gatcttatat ttctctcatc tcagagcctg    8910
tcctgagttg taaggtattt catactgcct tacttaaaag ttttttaaac tactagagtc    8970
atttgataca cacagaagtt acctaataat ccaaagatgt ccatcaaggg aggaagggtg    9030
ggtcatcaga ctttgccttt gatgttgtag actaggctcc tgagttaagc agcagaggga    9090
cagcagtgcc atgtgccttc actgtgtccc aggaaatctg ggttggttcc agtgggaaat    9150
accagtattt cttggttctg gaaagtagca aagagtagg agatggggaa ataggggatgg    9210 ggagagcaag ccccgcatgt ccatggcgag tcaggtgggg agcacgggtg aagggccgg    9270 ctgttgacag acagactaag ctgtgtggtg ctcttgccgc ccttcctgg gtacagagct    9330 tgagaaaaat gcagccgacc actccctgtg tttgtacaga gcaaagccca aaagccaacc    9390
tcagatctcc tgatttggca gctgaagaaa tcagcagagt cctgattgcc tgattcagtc    9450
ccaaaaatga atgtcaggcc ccgccccctc cccaccaaca ttgcctctcc tacattctcc    9510
ttctgcccct aaatcagaca ggaggccaga gaggagtatt gctcaatgcg tgctatgtgc    9570
aactcctcag gccttgtgcc acctccatgc tgagccctga agcagggtgt cctgggtgcc    9630
tgtgtgtcag ctccctcctc tctacctacc tctgaccttc ttgtgggtga gggtggccat    9690
gcttatggcc atcttaaaac tggagaggca gagaactact tatgagtctg tagaccacgt    9750
gttgtcttcc atggcctgtt tctcctgctg tctgggtgag tgagcctgca acgcaatgcc    9810
```

```
catgagagta aatgcctcct gacctaccct gctcagcact gttctagtgt cttggccttg    9870
aaagaaaagc ctgacttcct gctgacacat gtggtagggg catggcagct atgaggcacc    9930
tcctacgtct gttttctggc tgtggtgact tgggattttt aaccttatat atcttttcc     9990
tttactcaaa acaaaacaat ttttagcaca ctgaaaaaaa aaaaaagcca aatgttttgt   10050
gcctttctaa ggcagcactg tatcccaggc tgcattttag gacttaatat ggaaatacca   10110
gagtctgagc tcctctacct tgagtttcat tagtccttag tgtctaggag acaggaaaga   10170
atgctctctg tgactggaga ggtgacatgc aggtgcagtg tgtctggagt ccctttcccc   10230
tgctgtgaga cttcagtgga ggagagaagc attgtaccct gggatcattt ggttggttcc   10290
aatcacaagc ttagttatca ggttgcatgc cttgtctcct gcaaaagaca gaatgtttca   10350
caattcccag gtaaactctg gaccattcca agtgtcctag ccttctgatg acattaatta   10410
cctagttgtg tcgaggagta taggatggac tctcctgaga aggggaggtt ggtggctttg   10470
tcttttcttt ttgctggatc ctgaactggt ctagacctcc tgcccccacc ccccagcccc   10530
catcagatgt ggctggcctt tcatttgaag gcttcagact taaagcatta agcagctagt   10590
gccctctgca gggcctggtt tccccaggga agggcagcaa ggaacatggg accagaagcc   10650
tgtcctcagt aatgtgacta tagtgagctt tagcaaaagt ttttctatat aatgacatct   10710
tacttatctt ttacccttc ctcagttttc ccctgccttt aactaataaa gaattgggag    10770
acagaaattt taaagtcctc cttattcaag attttgaaat tcttagcctg ggagtgctgg   10830
agagaacctg atgctttctc cagaatgaag agtcccaatt tgtatatcag tgttaagaag   10890
aaaacaaaac aaacacatag gtgagatttt cgtggactat tttaaaaatg tgtcattaat   10950
ataaaaaatt tatattagca gtatttaatc attctcacct gtaaagaata agaaaaacag   11010
aaggtaaata ttcttacaga gaatagcaga gctttaagat tcattttcat tttaagtcca   11070
ttttattttg ccagtgtatt aatgtttaga agtctgtttt actaatgtta tttattaatt   11130
ttttttcatt tccatacaca gttagttaac taaagagctt tttcaagcac ccatgtctgt   11190
aaaaaaatat ttttaaataa agtttctttt gttgtagcag aaaaaaaaaa a            11241
```

<210> SEQ ID NO 113
<211> LENGTH: 906
<212> TYPE: PRT
<213> ORGANISM: Artificial Sequence
<220> FEATURE:
<223> OTHER INFORMATION: Synthetic

<400> SEQUENCE: 113

Met Ala Gly Asn Val Lys Lys Ser Ser Gly Ala Gly Gly Gly Ser Gly
1               5                   10                  15

Ser Gly Gly Ser Gly Ser Gly Gly Leu Ile Gly Leu Met Lys Asp Ala
            20                  25                  30

Phe Gln Pro His His His His His His Leu Ser Pro His Pro Pro
        35                  40                  45

Gly Thr Val Asp Lys Lys Met Val Glu Lys Cys Trp Lys Leu Met Asp
    50                  55                  60

Lys Val Val Arg Leu Cys Gln Asn Pro Lys Leu Ala Leu Lys Asn Ser
65                  70                  75                  80

Pro Pro Tyr Ile Leu Asp Leu Leu Pro Asp Thr Tyr Gln His Leu Arg
                85                  90                  95

Thr Ile Leu Ser Arg Tyr Glu Gly Lys Met Glu Thr Leu Gly Glu Asn
            100                 105                 110

Glu Tyr Phe Arg Val Phe Met Glu Asn Leu Met Lys Lys Thr Lys Gln

-continued

```
            115                 120                 125
Thr Ile Ser Leu Phe Lys Glu Gly Lys Glu Arg Met Tyr Glu Asn
130                 135                 140

Ser Gln Pro Arg Arg Asn Leu Thr Lys Leu Ser Leu Ile Phe Ser His
145                 150                 155                 160

Met Leu Ala Glu Leu Lys Gly Ile Phe Pro Ser Gly Leu Phe Gln Gly
                165                 170                 175

Asp Thr Phe Arg Ile Thr Lys Ala Asp Ala Ala Glu Phe Trp Arg Lys
                180                 185                 190

Ala Phe Gly Glu Lys Thr Ile Val Pro Trp Lys Ser Phe Arg Gln Ala
                195                 200                 205

Leu His Glu Val His Pro Ile Ser Ser Gly Leu Glu Ala Met Ala Leu
                210                 215                 220

Lys Ser Thr Ile Asp Leu Thr Cys Asn Asp Tyr Ile Ser Val Phe Glu
225                 230                 235                 240

Phe Asp Ile Phe Thr Arg Leu Phe Gln Pro Trp Ser Ser Leu Leu Arg
                245                 250                 255

Asn Trp Asn Ser Leu Ala Val Thr His Pro Gly Tyr Met Ala Phe Leu
                260                 265                 270

Thr Tyr Asp Glu Val Lys Ala Arg Leu Gln Lys Phe Ile His Lys Pro
                275                 280                 285

Gly Ser Tyr Ile Phe Arg Leu Ser Cys Thr Arg Leu Gly Gln Trp Ala
                290                 295                 300

Ile Gly Tyr Val Thr Ala Asp Gly Asn Ile Leu Gln Thr Ile Pro His
305                 310                 315                 320

Asn Lys Pro Leu Phe Gln Ala Leu Ile Asp Gly Phe Arg Glu Gly Phe
                325                 330                 335

Tyr Leu Phe Pro Asp Gly Arg Asn Gln Asn Pro Asp Leu Thr Gly Leu
                340                 345                 350

Cys Glu Pro Thr Pro Gln Asp His Ile Lys Val Thr Gln Glu Gln Tyr
                355                 360                 365

Glu Leu Tyr Cys Glu Met Gly Ser Thr Phe Gln Leu Cys Lys Ile Cys
                370                 375                 380

Ala Glu Asn Asp Lys Asp Val Lys Ile Glu Pro Cys Gly His Leu Met
385                 390                 395                 400

Cys Thr Ser Cys Leu Thr Ser Trp Gln Glu Ser Glu Gly Gln Gly Cys
                405                 410                 415

Pro Phe Cys Arg Cys Glu Ile Lys Gly Thr Glu Pro Ile Val Val Asp
                420                 425                 430

Pro Phe Asp Pro Arg Gly Ser Gly Ser Leu Leu Arg Gln Gly Ala Glu
                435                 440                 445

Gly Ala Pro Ser Pro Asn Tyr Asp Asp Asp Asp Glu Arg Ala Asp
                450                 455                 460

Asp Thr Leu Phe Met Met Lys Glu Leu Ala Gly Ala Lys Val Glu Arg
465                 470                 475                 480

Pro Pro Ser Pro Phe Ser Met Ala Pro Gln Ala Ser Leu Pro Pro Val
                485                 490                 495

Pro Pro Arg Leu Asp Leu Leu Pro Gln Arg Val Cys Val Pro Ser Ser
                500                 505                 510

Ala Ser Ala Leu Gly Thr Ala Ser Lys Ala Ala Ser Gly Ser Leu His
                515                 520                 525

Lys Asp Lys Pro Leu Pro Val Pro Pro Thr Leu Arg Asp Leu Pro Pro
530                 535                 540
```

```
Pro Pro Pro Pro Asp Arg Pro Tyr Ser Val Gly Ala Glu Ser Arg Pro
545                 550                 555                 560

Gln Arg Arg Pro Leu Pro Cys Thr Pro Gly Asp Cys Pro Ser Arg Asp
                565                 570                 575

Lys Leu Pro Pro Val Pro Ser Ser Arg Leu Gly Asp Ser Trp Leu Pro
            580                 585                 590

Arg Pro Ile Pro Lys Val Pro Val Ser Ala Pro Ser Ser Ser Asp Pro
        595                 600                 605

Trp Thr Gly Arg Glu Leu Thr Asn Arg His Ser Leu Pro Phe Ser Leu
610                 615                 620

Pro Ser Gln Met Glu Pro Arg Pro Asp Val Pro Arg Leu Gly Ser Thr
625                 630                 635                 640

Phe Ser Leu Asp Thr Ser Met Ser Met Asn Ser Ser Pro Leu Val Gly
                645                 650                 655

Pro Glu Cys Asp His Pro Lys Ile Lys Pro Ser Ser Ser Ala Asn Ala
            660                 665                 670

Ile Tyr Ser Leu Ala Ala Arg Pro Leu Pro Val Pro Lys Leu Pro Pro
        675                 680                 685

Gly Glu Gln Cys Glu Gly Glu Glu Asp Thr Gly Tyr Met Thr Pro Ser
690                 695                 700

Ser Arg Pro Leu Arg Pro Leu Asp Thr Ser Gln Ser Ser Arg Ala Cys
705                 710                 715                 720

Asp Cys Asp Gln Gln Ile Asp Ser Cys Thr Tyr Glu Ala Met Tyr Asn
                725                 730                 735

Ile Gln Ser Gln Ala Pro Ser Ile Thr Glu Ser Ser Thr Phe Gly Glu
            740                 745                 750

Gly Asn Leu Ala Ala Ala His Ala Asn Thr Gly Pro Glu Glu Ser Glu
        755                 760                 765

Asn Glu Asp Asp Gly Tyr Asp Val Pro Lys Pro Pro Val Pro Ala Val
770                 775                 780

Leu Ala Arg Arg Thr Leu Ser Asp Ile Ser Asn Ala Ser Ser Ser Phe
785                 790                 795                 800

Gly Trp Leu Ser Leu Asp Gly Asp Pro Thr Thr Asn Val Thr Glu Gly
                805                 810                 815

Ser Gln Val Pro Glu Arg Pro Pro Lys Pro Phe Pro Arg Arg Ile Asn
            820                 825                 830

Ser Glu Arg Lys Ala Gly Ser Cys Gln Gln Gly Ser Gly Pro Ala Ala
        835                 840                 845

Ser Ala Ala Thr Ala Ser Pro Gln Leu Ser Ser Glu Ile Glu Asn Leu
850                 855                 860

Met Ser Gln Gly Tyr Ser Tyr Gln Asp Ile Gln Lys Ala Leu Val Ile
865                 870                 875                 880

Ala Gln Asn Asn Ile Glu Met Ala Lys Asn Ile Leu Arg Glu Phe Val
                885                 890                 895

Ser Ile Ser Ser Pro Ala His Val Ala Thr
            900                 905
```

<210> SEQ ID NO 114
<211> LENGTH: 1390
<212> TYPE: PRT
<213> ORGANISM: Artificial Sequence
<220> FEATURE:
<223> OTHER INFORMATION: Synthetic human c-Met protein

<400> SEQUENCE: 114

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
    275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
    355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
```

```
              420                 425                 430
Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845
```

```
Met Ile Ser Met Gly Asn Glu Asn Val Leu Glu Ile Lys Gly Asn Asp
    850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
        915                 920                 925
Gln Asn Phe Thr Gly Leu Ile Ala Gly Val Val Ser Ile Ser Thr Ala
    930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
                965                 970                 975
Thr Pro His Leu Asp Arg Leu Val Ser Ala Arg Ser Val Ser Pro Thr
            980                 985                 990
Thr Glu Met Val Ser Asn Glu Ser Val Asp Tyr Arg Ala Thr Phe Pro
        995                 1000                1005
Glu Asp Gln Phe Pro Asn Ser Ser Gln Asn Gly Ser Cys Arg Gln Val
    1010                1015                1020
Gln Tyr Pro Leu Thr Asp Met Ser Pro Ile Leu Thr Ser Gly Asp Ser
1025                1030                1035                1040
Asp Ile Ser Ser Pro Leu Leu Gln Asn Thr Val His Ile Asp Leu Ser
                1045                1050                1055
Ala Leu Asn Pro Glu Leu Val Gln Ala Val Gln His Val Val Ile Gly
            1060                1065                1070
Pro Ser Ser Leu Ile Val His Phe Asn Glu Val Ile Gly Arg Gly His
        1075                1080                1085
Phe Gly Cys Val Tyr His Gly Thr Leu Leu Asp Asn Asp Gly Lys Lys
    1090                1095                1100
Ile His Cys Ala Val Lys Ser Leu Asn Arg Ile Thr Asp Ile Gly Glu
1105                1110                1115                1120
Val Ser Gln Phe Leu Thr Glu Gly Ile Ile Met Lys Asp Phe Ser His
                1125                1130                1135
Pro Asn Val Leu Ser Leu Leu Gly Ile Cys Leu Arg Ser Glu Gly Ser
            1140                1145                1150
Pro Leu Val Val Leu Pro Tyr Met Lys His Gly Asp Leu Arg Asn Phe
        1155                1160                1165
Ile Arg Asn Glu Thr His Asn Pro Thr Val Lys Asp Leu Ile Gly Phe
    1170                1175                1180
Gly Leu Gln Val Ala Lys Gly Met Lys Tyr Leu Ala Ser Lys Lys Phe
1185                1190                1195                1200
Val His Arg Asp Leu Ala Ala Arg Asn Cys Met Leu Asp Glu Lys Phe
                1205                1210                1215
Thr Val Lys Val Ala Asp Phe Gly Leu Ala Arg Asp Met Tyr Asp Lys
            1220                1225                1230
Glu Tyr Tyr Ser Val His Asn Lys Thr Gly Ala Lys Leu Pro Val Lys
        1235                1240                1245
Trp Met Ala Leu Glu Ser Leu Gln Thr Gln Lys Phe Thr Thr Lys Ser
1250                1255                1260
```

-continued

```
Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
                1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
        1315                1320                1325

Ser Phe Ser Glu Leu Val Ser Arg Ile Ser Ala Ile Phe Ser Thr Phe
    1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
                1365                1370                1375

Asp Glu Val Asp Thr Arg Pro Ala Ser Phe Trp Glu Thr Ser
            1380                1385                1390
```

USE OF LRIG1 AS A BIOMARKER FOR IDENTIFYING A SUBJECT FOR APPLICATION OF ANTI-C-MET ANTIBODIES

CROSS-REFERENCE TO RELATED APPLICATIONS

This application claims the benefit of Korean Patent Application No. 10-2012-0080144, filed on Jul. 23, 2012 and Korean Patent Application No. 10-2012-0102398, filed on Sep. 14, 2012, in the Korean Intellectual Property Office, the disclosures of which are herein incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 178,916 Byte ASCII (Text) file named "712416 ST25-Revised2.TXT" created on Jul. 24, 2015.

BACKGROUND

1. Field

The present disclosure relates to a biomarker for identifying a subject suitable for treatment with anti-c-Met antibodies, a method of identifying a subject suitable for application of the specific anti-c-Met antibody including determining an LRIG1 level, and a method for the prophylaxis and/or therapy of c-Met-related diseases including administering an effective amount of an anti-c-Met antibody to the identified subject.

2. Description of the Related Art c-Met is a receptor for hepatocyte growth factor (HGF), a cytokine that binds the extracellular region of the c-Met receptor tyrosine kinase to induce cell division, movement, morphogenesis, and angiogenesis of various normal cells and tumor cells. c-Met is a representative receptor tyrosine kinase existing on the surface of cells, is itself a proto-oncogene, and is sometimes involved in various mechanisms related to cancer, such as cancer development, metastasis, migration, invasion, and angiogenesis, independent from a ligand, HGF. Thus, c-Met has been recently emerging as a new target for anti-cancer therapy.

In particular, c-Met is known to be involved in induction of resistance to commonly used anti-cancer drugs, and thus is regarded as important with respect to personalized treatments. Representative anti-cancer therapeutic drugs targeting epidermal growth factor receptor EGFR (ERBB1), i.e., Eribitux or Tarceva, work by blocking the signaling related to cancer development. In addition, Herceptin, which is well known as a breast cancer therapeutic drug, targets ERBB2 (HER2) and works by blocking the transduction of signals necessary for cell proliferation. Among patients resistant to the drugs described above, the signal transduction pathway that induces cell proliferation is not blocked due to the overexpression of c-Met. Thus, c-Met has emerged as a target of interest for many pharmaceutical companies. Still, there is a need for additional anti-c-Met antibodies and related methods and compositions.

Some of the antibodies developed were found to have adverse effects. When they retain their intrinsic structures, anti-c-Met antibodies interfere with the binding of the ligand HGF to c-Met receptor, but may also act as an agonist to trigger the signaling pathway of oncogenesis by antibody-mediated dimerization of the c-Met receptor. To avoid c-Met dimerization, anti-c-Met antibodies were structurally changed from a two-armed configuration to a one-armed configuration by genetic recombination. One-armed antagonistic antibodies to c-Met were effective when used in combination with another anticancer agent, but did not exhibit significant anticancer effects when used alone.

Cbl (E3 ligase) is known to play a leading role in the degradation of c-Met. Many c-Met inhibitors initiate Cbl-mediated c-Med degradation through ubiquitination. However, c-Met inhibitors do not show the desired therapeutic effect in patients in which Cbl cannot properly interact with c-Met due to a mutation or a quantitative reduction of Cbl or due to a mutation of c-Met.

In addition, when c-Met is activated by the ligand HGF, phosphorylation at Y1003 allows the recruitment of the Cbl enzyme to c-Met. In other words, the activation of the c-Met is a prerequisite for the recruitment of the Cbl enzyme to the c-Met. Accordingly, an anticancer therapy based on Cbl-mediated c-Met degradation is executed necessarily under the condition of c-Met activation which results in an adverse effect (agonism).

There is therefore a need for a novel technique by which c-Met activity may be effectively inhibited according to kind of cancer and/or a patient's genetic makeup, with a great reduction in adverse effects.

SUMMARY

Provided is a biomarker for identifying a cancer cell and/or a patient to which an anti-c-Met antibody is applicable.

Further provided is a composition and a kit for identifying a subject suitable for application of an anti-c-Met antibody, including a biomarker.

Further provided is a method of identifying a subject suitable for application of an anti-c-Met antibody, by measuring a biomarker.

Further provided is a method of inhibiting c-Met activity, including administering a therapeutically effective amount of an anti-c-Met antibody to a subject who is identified as being suitable for treatment with an anti-c-Met antibody.

Further provided is a method of preventing and/or treating a c-Met-related disease, including administering a therapeutically effective amount of an anti-c-Met antibody to a subject who is identified as being suitable for treatment with an anti-c-Met antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the embodiments, taken in conjunction with the accompanying drawings of which:

FIG. 1A-1D shows differences in the in vitro inhibitory activity of antibodies against c-Met, wherein FIG. 1A is a graph showing c-Met levels in NCI-H441 cells incubated for 24 hours with anti-c-Met antibodies, as percentages of the c-Met level in the control (IgG treated, 100%), as measured by ELISA, FIG. 1B shows Western blot photographs of the phosphorylation of kinases downstream of c-Met in NCI-H441 cells (left panel) and Caki-1 cells (right panel), FIG. 10 is a graph showing c-Met levels in MKN45 cells incubated for 24 hours with anti-c-Met antibodies as percentages of the c-Met level in the control (IgG treated, 100%), as measured by ELISA, and FIG. 1D is a graph showing the viability of MKN45 cells incubated for 72 hours with various concentrations of IgG (○) or the anti-c-Met antibody L3-1Y (♦) as percentages of the viability of the control (no antibody treated, 100%), as measured by a CCK-8 assay (mean±SD);

FIG. 2A-2E shows c-Met signaling and Cbl-mediated c-Met degradation, wherein

FIG. 2A shows photographs of co-immunoprecipitation with anti-c-Met antibodies,

FIG. 2B is a graph showing c-Met levels in EBC-1 and NCI-H441 cells incubated for 4 hours with anti-c-Met antibodies as percentages of the c-Met level in the control (medium), as measured by ELISA, FIG. 2C shows photographs of Cbl protein levels in EBC-1 and NCI-H441 cells as analyzed by Western blotting, FIG. 2D is a graph of c-Met levels in cells plotted against treatment factors including the c-Met inhibitor PHA-665752 (Selleck Chemicals) and the anti-c-Met antibody L3-1Y or 5D5, showing that L3-1Y may trigger c-Met degradation although c-Met activity is inhibited, unlike 5D5, and FIG. 2E is a graph showing the viability of EBC-1 cells incubated for 72 hours with various concentrations of antibodies 5D5 (○) and L3-1Y (♦) as percentages of the viability of the control (no antibody treated, 100%), as measured by a CCK-8 assay;

FIG. 3A-3G illustrates the ability of the antibody L3-1Y to induce c-Met degradation in a Cbl-independent mechanism, wherein FIGS. 3A and 3B are photographs showing immunoblots of protein extracts from EBC-1 cells (3A) and NCI-H441 cells (3B) incubated with L3-1Y or 5D5, detected with an anti-Ub antibody, FIG. 3C is a graph showing c-Met levels in Cbl siRNA-transformed EBC-1 cells incubated with anti-c-Met antibodies as percentages of the c-Met level in the control (IgG treated, 100%), as measured by ELISA, FIG. 3D is a graph showing c-Met levels in EBC-1 cells incubated with anti-c-Met antibodies, and DMSO or MG132 as percentages of the c-Met level in the control (IgG treated, 100%), as measured by ELISA, FIG. 3E is a graph showing relative viability of HS746T cells incubated with various concentrations of antibody 5D5 (○) or L3-1Y (♦), as measured by a CCK-8 assay, FIG. 3F is a graph showing the relative apoptosis of HS746T cells treated with various concentrations of IgG (○), L3-1Y (♦), and 5D5 (▲) as measured by Caspase 3/7 Glo assay, and FIG. 3G is a graph showing the relative apoptosis of EBC-1 cells treated with various concentrations of L3-1Y and 5D5 as measured by Caspase 3/7 Glo assay;

FIG. 4A-4G illustrates the mediation of anti-c-Met antibody L3-1Y-induced c-Met degradation by LRIG1, wherein FIG. 4A is a photograph after lysates from EBC-1 cells treated with L3-1Y were immunoprecipitated with anti-c-Met antibody-conjugated beads and subjected to immunoblotting with the anti-LRIG1 antibody, showing that the antibody L3-1Y induces the association of c-Met and LRIG1 both present at endogenous levels, FIG. 4B is a graph showing co-immunoprecipitation with LRIG1 and c-Met in HEK-293T cells incubated for 120 min with L3-1Y or 5D5, FIG. 4C shows 5D5- or L3-1Y-induced apoptosis in EBC-1 cells, as measured by FACS analysis, FIG. 4D is a graph showing the relative apoptosis of EBC-1 cells treated for 72 hours with various concentrations of L3-1Y (♦) or 5D5 (○) as measured by Caspase 3/7 Glo assay, FIG. 4E is a graph showing relative apoptosis of LRIG1-knockdown in EBC-1 cells treated with L3-1Y (♦), FIG. 4F is a graph showing c-Met levels in EBC-1 cells incubated with anti-c-Met antibodies, and DMSO or concanamycin as percentages of the c-Met level in the control (IgG treated, 100%), as measured by ELISA, and FIG. 4G shows immunofluorescence images of the co-localization of L3-1Y and lysosomes in EBC-1 cells (left panel) and MKN45 (right panel);

FIG. 5A-5D illustrates that LRIG1 mediates c-Met degradation and tumor growth inhibition in Cbl mutant tumors or Cbl-negative tumors in vivo, wherein FIGS. 5A and 5B are graphs showing migration ability of EBC-1 cells (5C) and HS746T cells (5D), and FIGS. 5C and 5D are graphs showing the growth of tumor volumes of EBC-1 (5C) and HS746T (5D) with time (n=15);

FIG. 6A-6F illustrates therapeutic effects of the antibody L3-1Y on tumors resistant to EGFR-targeted therapy, wherein FIG. 6A is a photograph of immunoblots obtained with respective antibodies to p-c-Met, c-Met, EGFR, Cbl, LRIG1, and GAPDH in HCC827, HCC827 ER10, and HCC827 ER15 cells, FIG. 6B is a graph showing the relative viability of HCC827 ER15 cells incubated for 72 hours with Erlotinib and/or L3-1Y, as measured by a CTG assay.

FIG. 6C is a graph showing c-Met levels in HCC827 ER15 cells incubated for 24 hours with anti-c-Met antibodies and 100 nM Erlotinib as percentages of the c-Met level in the control (IgG treated, 100%), as measured by ELISA, FIG. 6D is a graph showing the levels of EGFR, Cbl, and the control GAPDH in LXFE 1422, LXFA 526, and LXFA 1647 patient samples as measured by Western blot analysis, FIG. 6E is a graph showing RT-PCR products containing the exon 14 of the c-Met gene from LXFE 1422, LXFA 526, and LXFA 1647 samples, separated on agarose gel by electrophoresis, and FIG. 6F shows clonogenicity of LXFE 1422, LXFA 526, and LXFA 1647, all incubated with the antibody L3-1Y, in comparison with the non-treated control;

FIG. 7 is a graph showing the conversion of erlotinib-sensitive cells into erlotinib-resistant cells.

DETAILED DESCRIPTION

Figure 1A:
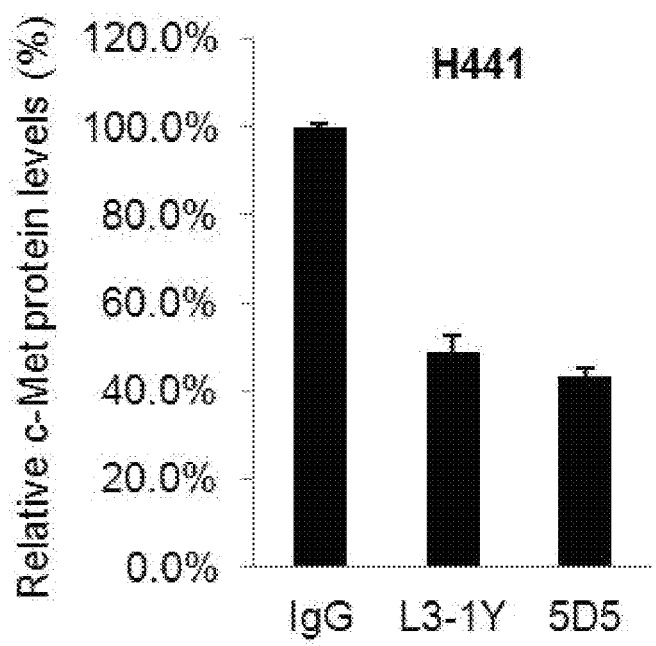

When Cbl does not interact with c-Met normally, due to a low level of the Cbl enzyme or a mutation in Cbl and/or c-Met, previously known anti-c-Met antibodies do not trigger c-Met degradation and thus are not effective for the therapy of c-Met-related diseases. The present invention provides an anti-c-Met antibody (hereinafter referred to as "specific anti-c-Met antibody" unless otherwise stated) initiates c-Met degradation even when the Cbl enzyme does not interact with the c-Met normally and is thus highly effective for the therapy of c-Met-related diseases. In addition, it is also found that the specific anti-c-Met antibody is involved in c-Met degradation via the LRIG1 (leucine-rich repeats and immunoglobulin-like domains protein 1) pathway, but not via the Cbl pathway, whereby a therapeutic technique of treating c-Met related diseases in a Cbl-independent manner is developed. The specific anti-c-Met antibody has the function of triggering LRIG1-mediated c-Met degradation, and thus has an effect of inducing c-Met degradation even on a cell in which Cbl is absent or present at a low level, or in which Cbl or c-Met is mutated so as not to interact with each other.

In an embodiment, there is provided a biomarker for identifying a subject to which the specific anti-c-Met antibody is applicable (hereinafter referred to as "a subject suitable for application of the specific anti-c-Met antibody"). The biomarker may be selected from the group consisting of LRIG1, an LRIG1 gene, an mRNA transcribed from a LRIG1 gene, and a combination thereof. The subject suitable for application of the specific anti-c-Met antibody may be a cell and/or a patient from which the cell is derived.

"LRIG1 (leucine-rich repeats and immunoglobulin-like domains protein 1)" refers to a transmembrane protein which interacts with receptor tyrosine kinases of the EGFR-family, MET, and RET. LRIG1 may be derived from mammals including primates such as humans and monkeys, and rodents such as rats and mice. LRIG1 may be human LRIG1 (polypeptide encoded by Accession No. NM_015541 or NP_056356).

The term "Cbl", "Cbl protein", or "Cbl enzyme," as used herein, refers to E3 ligase involved in cell signalling and protein ubiquitination. This protein has functions of intracellular internalization of c-Met protein positioned on tumor cell membrane and degradation thereof. The protein may be a polypeptide encoded by the nucleotide sequence of GenBank Accession Number (NM_005188, NM_007619, NM_170662, or NM_001033238) or a polypeptide having the amino acid sequence of GenBank Accession Number (NP_005199, NP_031645, NP_733762, or NP_001028410).

The term "c-Met" or "c-Met protein" refers to a receptor tyrosine kinase (RTK) which binds hepatocyte growth factor (HGF). c-Met may be a c-Met protein from any species, particularly a mammal or primate, for instance, human c-Met (e.g., NP_000236), or monkey c-Met (e.g., *Macaca mulatta*, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various mechanisms, such as cancer development, metastasis, migration of cancer cell, invasion of cancer cell, angiogenesis, and the like.

Most of the anti-c-Met antibodies developed thus far induce c-Met internalization and degradation through interaction between Cbl and c-Met. Hence, when Cbl is absent or present at a low level within cells or when Cbl or c-Met is mutated at its site responsible for degradation (such as a binding site), pre-existing anti-c-Met antibodies cannot induce c-Met degradation, thus rendering them therapeutically ineffective.

In contrast, the specific anti-c-Met antibody disclosed herein is found to trigger c-Met degradation independent of whether Cbl interacts with c-Met. This Cbl-independent activation mechanism of the specific anti-c-Met antibody was attributed to the fact that the c-Met degradation triggered by the specific anti-c-Met antibody is mediated by LRIG1. That is, the specific anti-c-Met antibody can induce binding of LRIG1 to c-Met, leading to internalization of LRIG1-c-Met complex and degradation of c-Met, despite a low level of Cbl or the lack of interaction between Cbl and c-Met. Accordingly, the specific anti-c-Met antibody triggers c-Met degradation and thus can be applied to the therapy of c-Met-related diseases when LRIG1 is present, irrespective of whether Cbl is present or loses its function.

An embodiment provides a method of identifying a subject suitable for application of the specific anti-c-Met antibody by measuring the level of LRIG1 in a cell sample, whereby excellent c-Met degradation can be achieved and thus c-Met-related diseases can be effectively treated even in subjects in which conventional antibody therapy has not been effective.

Another embodiment provides a method of identifying a subject suitable for application of the specific anti-c-Met antibody or providing information for diagnosing the subject, including determining an LRIG1 level in a cell sample.

The method of identifying a subject suitable for application of the specific anti-c-Met antibody includes:

(1) determining an LRIG1 level in a cell sample; and (2) optionally, determining the cell or the patient from with the cell sample is originated as a subject suitable for application of the specific anti-c-Met antibody when LRIG1 is present, wherein the presence of LRIG1 in the cell sample may be determined as a stain intensity of '+2' or '+3' as analyzed by immunohistochemical staining using an anti-LRIG1 antibody.

As used herein, the "determining" step includes qualitatively or quantitatively measuring the factor of interest, such as an LRIG1 level, and/or evaluating the measured results.

The cell sample may be an artificially constructed cell, a cell separated from a patient of interest, a culture of the cell, a lysate of the cell, or an extract from the cell; or a protein, DNA, or RNA, all derived from the cell, the cell culture, the cell lysate, or the cell extract. The cell may be a cancer cell (tumor cell). The cancer cell may be selected from the group consisting of squamous cell carcinoma, small cell lung cancer, non-small cell lung cancer, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, chronic or acute leukemia, lymphocyte lymphoma, hepatoma, stomach cancer, pancreatic cancer, glioblastoma, cervical cancer, ovarian cancer, liver cancer, bladder cancer, hepatic tumor, breast cancer, colon cancer, large intestine cancer, endometrial cancer, uterine cancer, salivary gland cancer, renal cancer, prostate cancer, vulvar cancer, thyroid cancer, and head and neck cancer.

In one embodiment, the method is carried out using a very small amount of protein, DNA, or RNA extracted from the cell. For example, the amount of protein ranging from about 0.1 to about 100 µg, from about 0.5 to about 50 µg, or from about 1 to about 10 µg, for example, from about 3 to about 7 µg, and/or the amount of DNA or RNA ranging from about 0.1 to about 50 µg, from about 0.3 to about 30 µg, from about 0.5 to about 5 µg, for example from about 0.8 to about 1.2 µg suffices for the execution of the method.

Examples of the patient may be mammals including primates such as humans, monkeys, etc., and rodents such as mice, rats, etc., with preference for humans. For example, the patient may suffer from a cancer selected from the group consisting of squamous cell carcinoma, small cell lung cancer, non-small cell lung cancer, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, chronic or acute leukemia, lymphocyte lymphoma, hepatoma, stomach cancer, pancreatic cancer, glioblastoma, cervical cancer, ovarian cancer, liver cancer, bladder cancer, hepatic tumor, breast cancer, colon cancer, large intestine cancer, endometrial cancer, uterine cancer, salivary gland cancer, renal cancer, prostate cancer, vulvar cancer, thyroid cancer, and head and neck cancer.

Another embodiment provides a composition for the identification (diagnosis) of a subject suitable for application of the specific anti-c-Met antibody, including an LRIG1 detection agent.

Another embodiment provides a kit for the identification (diagnosis) of a subject suitable for application of the specific anti-c-Met antibody, including an LRIG1 detection agent and a detection means.

The determination of the presence of LRIG1 and/or LRIG1 level may be conducted by any suitable method of determining expression, such as by mRNA detection/quantification or measuring a gene copy number or by measuring an LRIG1 level with a protein quantification means and/or evaluating the measured results. By way of example, the presence of LRIG1 and/or LRIG1 level may be determined through an enzyme reaction, a fluorescence reaction, a luminescence action, and/or a radiation reaction using a LRIG1-specific antibody or aptamer. The presence of LRIG1 and/or LRIG1 level can be analyzed using a method including, but not limited to, immunochromatography, immunohistochemistry, enzyme linked immunosorbent assay (ELISA), radioimmunoassay (RIA), enzyme immunoassay (EIA), florescence immunoassay (FIA), luminescence immunoassay (LIA), and Western blotting. The LRIG1 detection agent for determining an LRIG1 level may be selected from the group consisting of an anti-LRIG1 antibody, an aptamer specifically binding to LRIG1, and a combination thereof.

When Cbl is absent or present at a low level in cancer cells, preexisting anti-c-Met antibodies cannot induce c-Met degradation. However, the specific anti-c-Met antibody of the present invention can initiate c-Met degradation and, thus, is highly effective for the therapy of c-Met-related diseases if LRIG1 is present, preferably at a high level, in the cell sample.

Because it can be difficult to quantitatively analyze protein concentrations in a cell sample, qualitative or semi-quantitative analysis may be used as an alternative. Qualitative methods, including immunohistochemical staining, are well known in the art. For example, the level of a protein of interest may be determined by immunohistochemical staining using an antibody (e.g., antibody #2747 (Cell signaling) for Cbl, ab36707 (Abcam) for LRIG1, and the like) that binds to a protein in a sample. The staining may be scored on a scale ranging, e.g., from '−' or '0' to '+3,' wherein a score (stain intensity) of '−' or '0' represents no protein expression (no signal), score of '+1' represents no or a slight protein expression (corresponding to a background signal), and scores of '+2' to '+3' represent progressively higher levels of protein expression (a case with a signal higher than '+3' is incorporated in the score of '+3'). In the present invention, "the presence of LRIG1" may be defined as a stain intensity of '+2' or '+3' when analyzed by immunohistochemical staining using an anti-LRIG1 antibody or as equivalent results when analyzed by other protein analysis methods.

Thus, when the level of LRIG1 in a cell sample is determined to be '+2' or +3' in terms of stain intensity as measured by immunohistochemical staining using an anti-LRIG1 antibody, the patient from which the cell sample is taken (separated) can be determined as a subject suitable for application of the specific anti-c-Met antibody.

If LRIG1 is present (for example, at a predetermined level) in cells, as described above, the specific anti-c-Met antibody can trigger c-Met degradation even in the case where pre-existing anti-c-Met antibodies are ineffective because of the absence of normal interaction between Cbl and c-Met, which is attributable to the absence of intracellular Cbl, the presence of intracellular Cbl at a low level, or a mutation on a functional Cbl molecule or a site of c-Met for interaction with Cbl. Thus, the method of identifying a subject suitable for application of the specific anti-c-Met antibody is useful when Cbl is not expressed or is expressed at a low level, Cbl is functionally mutated, or a site of c-Met for interaction with Cbl is mutated.

In one embodiment, therefore, the method of identifying a subject suitable for application of the specific anti-c-Met antibody may further include (1-1) determining a Cbl concentration, a Cbl mutation, and/or a mutation of a site of c-Met for interaction with Cbl in a cell sample taken from a patient. In addition, the method may further include determining the cell or the patient from which the cell sample is originated (separated) as a subject suitable for application of the specific anti-c-Met antibody when Cbl is present at a low level or is absent in the cell sample (e.g., the Cbl level in the cell sample is determined as a stain intensity of '+1' or '−' as analyzed by immunohistochemical staining using an anti-Cbl antibody) or when a mutation is present on either or both Cbl and the site of c-Met for interaction with Cbl.

In one embodiment, the method of identifying a subject suitable for application of the specific anti-c-Met antibody includes:

(1) determining an LRIG1 level in a cell sample;

(1-1) determining a Cbl concentration, a Cbl mutation, and/or a mutation of a site of c-Met for interaction with Cbl in the cell sample; and (2) optionally, determining the cell or the patient from which the cell sample originated as a subject suitable for application of the specific anti-c-Met antibody when the Cbl concentration is absent or found at low levels, or when a mutation is present on Cbl and/or the c-Met site for interaction with c-Met, with a proviso that the LRIG1 is present (e.g., when that LRIG1 level is determined as a stain intensity of '+2' or '+3' as analyzed by immunohistochemical staining using an anti-LRIG1 antibody).

The determination of Cbl concentration may be conducted by any suitable method of determining expression, such as by mRNA detection/quantification or measuring a Cbl concentration using a protein quantification means, which is known in the relevant art, and/or evaluating the measured results. By way of example, a Cbl concentration may be determined through an enzyme reaction, a fluorescence reaction, a luminescence action, and/or a radiation reaction using a Cbl-specific antibody or aptamer. Detailed analyzing methods are as defined above. The Cbl detection agent for determining a Cbl concentration may be selected from the group consisting of an anti-Cbl antibody, an aptamer specifically binding to Cbl, and a combination thereof.

Cbl is present at a "low" level in a cancer cell or tissue sample if the level of Cbl is less than typically found in a cancer cell or tissue sample of the same type. For instance, the Cbl level of a cancer cell or tissue sample may be "low" if it is less than typically found in a cancer cell of the same type that is sensitive (not resistant) to an anti-c-Met antibody (e.g., 5D5 antibody, and the like) other than the specific anti-c-Met antibody or EGFR targeted therapy. For example, the Cbl level of a cancer cell or tissue sample may be "low" if it is less than (e.g., the minimum level) found in a cancer cell of the same type on which an anti-c-Met antibody (e.g., 5D5 antibody) other than the specific anti-c-Met antibody has therapeutic effect. As discussed above with respect to LRIG1, Cbl expression may be determined by immunohistochemical methods, and the resulting staining may be scored on a scale, e.g., from '−' or '0' to '+3,' wherein a score of '−' or '0' represents no protein expression (no signal), score of '+1' represents no or a slight protein expression (corresponding to a background signal), and scores of '+2' to '+3' represent progressively higher levels of protein expression.

When Cbl is not expressed or is expressed at a low intracellular level, e.g., when the intracellular level of Cbl is determined to be '+1' or '−', conventional anti-c-Met antibodies do not work effectively and thus are ineffective for the therapy of c-Met-related diseases. In contrast, the specific anti-c-Met antibody triggers c-Met degradation via the Cbl-independent LRIG1 pathway, and thus is advantageously applied where conventional antibodies do not work due to the absence of intracellular Cbl, the presence of intracellular Cbl at a low level, or a mutation on a functional Cbl molecule or a site of c-Met for interaction with Cbl.

In another embodiment, the method of identifying a subject suitable for application of the specific anti-c-Met antibody includes:

(1) determining an LRIG1 level in a cell sample;
(1-1') determining a Cbl concentration in the cell sample; and
(2') optionally, determining the cell or the patient from which the cell sample is originated as a subject suitable for application of the specific anti-c-Met antibody in case LRIG1 is present in the cell sample when Cbl is absent or present at a low level.

Wherein the case that LRIG1 is present may correspond to the case that the LRIG1 level is determined as a stain intensity of '+2' or '+3' as analyzed by immunohistochemical staining using an anti-LRIG1 antibody, and the absence of Cbl or the presence of Cbl at a low level in the cell sample may be defined as a stain intensity of '−' or '+1', when analyzed by immunohistochemical staining using an anti-Cbl antibody.

The term "Cbl mutation" refers to any mutation of the nucleotide sequence of the Cbl gene and/or of the amino acid sequence or structure of Cbl protein which causes the loss of a function responsible for interaction with c-Met (e.g., binding) and/or c-Met internalization and/or c-Met degradation (e.g., inhibits interaction between Cbl and c-Met).

In one embodiment, the Cbl mutation may be a deletion or substitution of 51 or more consecutive nucleotide residues, for example, 51 to 200 consecutive nucleotide residues, within a stretch from nt. (nucleotide) 1169 to nt. 1411 of the nucleotide sequence of GenBank Accession Number NM_005188, or a deletion or substitution of 17 or more amino acid consecutive residues, for example, 17 to 100 consecutive amino acid residues within a stretch from a.a. (amino acid) 343 to a.a. 424 of the amino acid sequence of GenBank Accession Number NP_005179. This mutation modifies the RING finger motif of Cbl, resulting in the loss of the E3 ligase function. That is, Cbl loses the ability to degrade other proteins due to the mutation of the nucleotides or amino acids.

The Cbl mutation leading to the incapacitation of Cbl may be determined using a method including, but not limited to, the direct analysis of nucleotide sequences or amino acid sequences, RT-PCR, and DNA sequencing.

The agent for detecting a Cbl mutation may be selected from the group consisting of a probe and primer capable of detecting the mutation, an anti-Cbl antibody specifically binding to a mutated Cbl, and an aptamer specifically binding to a mutated Cbl. The probe capable of detecting the Cbl mutation may be an about 10- to about 50-mer or about 20- to about 50-mer nucleotide sequence including a mutation region of the mutated Cbl gene and/or a complementary sequence thereto, or a sequence having a similarity of about 80% or higher, about 90% or higher, or about 95% or higher therewith. The primer capable of detecting the Cbl mutation may be an about 10- to about 50-mer or about 10- to about 30-mer oligonucleotide having a nucleotide sequence capable of hybridization with 5' and/or 3' terminus of a mutation region (about 50 to about 200 bp including the mutation site of Cbl) of the mutated Cbl gene, wherein the nucleotide sequence capable of hybridization may be a complementary sequence thereto, or a sequence having a similarity of about 80% or higher, about 90% or higher, or about 95% or higher therewith.

In cells wherein interaction between Cbl and c-Met and/or c-Met internalization and/or c-Met degradation is lost due to a mutation on Cbl, conventional anti-c-Met antibodies cannot induce c-Met degradation and thus are unable to treat c-Met-related diseases. However, the specific anti-c-Met antibody of the present invention can encourage c-Met degradation and thus is effective for the therapy of c-Met-related diseases even upon the loss of Cbl functions.

Therefore, if the Cbl protein or Cbl gene encoding it is found to have such a mutation in a cell sample taken from a patient, the cell or the patient can be determined to be a subject suitable for application of the specific anti-c-Met antibody.

In one embodiment, the method of identifying a subject suitable for application of the specific anti-c-Met antibody may include:

(1) determining an LRIG1 level in a cell sample;
(1-1") determining the presence of a mutation on a Cbl protein or a Cbl gene encoding the Cbl protein in the cell sample; and
(2") optionally, determining the cell or the patient from which the cell sample is originated as a subject suitable for application of the specific anti-c-Met antibody if LRIG1 is present in the cell sample when a mutation is present on the Cbl protein or the Cbl gene, wherein the LRIG1 level is determined as a stain intensity of '+2' or '+3' as analyzed by immunohistochemical staining using an anti-LRIG1 antibody.

As used herein, the term "c-Met mutation" is intended to refer to a mutation on a c-Met site responsible for recognizing and/or binding Cbl, and particularly to a mutation which incapacitates the interaction of Cbl with c-Met (e.g., binding) even though Cbl is present at a sufficient level or does not undergo such a mutation that leads to functional loss.

As used herein, the term "site of c-Met for interaction with Cbl" is intended to refer to a c-Met site which is recognized by Cbl so as to allow for c-Met internalization and degradation. Representative among the c-Met sites for interaction with Cbl are tyrosine at amino acid position 1003 (Y1003) and a region encoded by exon 14 of the c-Met gene. The exon 14 region of the c-Met gene stretches from nt. 3075 to nt. 3215 of the full-length nucleotide sequence of NM_000245, or corresponds to a region stretching from a.a. 964 to a.a. 1009 of the full-length amino acid sequence of NP_000236.

The c-Met mutation may be a deletion or a substitution of tyrosine at position 1003 (Y1003) with another amino acid residue (e.g., alanine, isoleucine, leucine, methionine, phenylalanine, proline, tryptophan, valine, asparagine, cysteine, glutamine, glycine, serine, threonine, aspartic acid, glutamine acid, arginine, histidine, and lysine, and preferably phenylalanine), or a deletion or substitution of 141 or more, for example, 141 to 300 consecutive nucleotide residues of exon 14 of the c-Met gene with other nucleotide residues, and/or a deletion or a substitution of 46 or more consecutive amino acid residues, for example, 46 to 100 consecutive amino acid residues of a polypeptide encoded by exon 14 with other amino acid residues. In a concrete embodiment, the c-Met mutation may be a deletion of tyrosine at position 1003 of c-Met (Y1003), a substitution of the tyrosine residue with phenylalanine, a deletion of exon 14 of the c-Met gene, or a deletion of the polypeptide encoded by exon 14.

The c-Met mutation may be determined using a method including, but not limited to, the direct analysis of nucleotide sequences or amino acid sequences, RT-PCR, and DNA sequencing. The agent for detecting a c-Met mutation may be selected from the group consisting of a probe or primer capable of detecting the mutation as described above, an anti-Cbl antibody specifically binding to a mutated Cbl, and an aptamer specifically binding to a mutated Cbl.

Whereas conventional anti-c-Met antibodies cannot induce Cbl-mediated c-Met degradation in the cells where a c-Met site which is recognized by Cbl or binds Cbl is mutated and thus are incapacitated from treating c-Met-related diseases, the specific anti-c-Met antibody can, thanks to its Cbl-independent, LRIG1-mediated activity. Thus, the specific anti-c-Met antibody is advantageously applied where the c-Met mutation takes place.

When the cell sample is found to have such a mutation on c-Met protein or c-Met gene encoding the protein, the cell or the patient from which the cell sample is taken can be determined to be a subject suitable for application of the specific anti-c-Met antibody.

In one embodiment, the method of identifying a subject suitable for application of the specific anti-c-Met antibody includes:

(1) determining an LRIG1 level in a cell sample;

(1-1''') determining the presence of a mutation on a site of c-Met for interaction with Cbl or on a region of c-Met gene corresponding to the site of c-Met for interaction with Cbl in the cell sample; and (2''') optionally, determining the cell or the patient from which the cell sample is originated as a subject suitable for application of the specific anti-c-Met antibody if LRIG1 is present in the cell sample when a mutation is present on the site of c-Met for interaction with Cbl or on the region of C-met gene corresponding to the c-Met site.

LRIG1 is considered to be present when the LRIG1 level is determined as a stain intensity of '+2' or '+3' as analyzed by immunohistochemical staining using an anti-LRIG1 antibody.

In the methods, the step (1) of determining an LRIG1 level in a cell sample may be carried out ahead of or behind the step (1-1), (1-1'), (1-1''), or (1-1''').

In another embodiment, the method may further include, in addition to steps (1) and (2), determining a Cbl concentration, a Cbl mutation, and/or a mutation of a site of c-Met for interaction with Cbl in the cell sample, and confirming the cell or the patient determined to be a subject suitable for application of the anti-c-Met antibody in steps (1) and (2) when Cbl is absent or present at a low level in the cell sample (e.g., the Cbl concentration in the cell sample is determined as a stain intensity of '+' or '−' as analyzed by immunohistochemical staining using an anti-Cbl antibody) or when a mutation is present on either or both Cbl and the site of c-Met for interaction with Cbl.

In another embodiment, the composition for the identification of a subject suitable for application of the specific anti-c-Met antibody further includes at least one selected from the group consisting of a Cbl detection agent for determining a Cbl concentration, an agent for detecting a Cbl mutation, and an agent for detecting a c-Met mutation, in addition to the LRIG1 detection agent for determining an LRIG1 level. That is, the composition includes an LRIG1 detection agent for determining an LRIG1 level and at least one selected from the group consisting of a Cbl detection agent for determining a Cbl concentration, an agent for detecting a Cbl mutation, and an agent for detecting a c-Met mutation.

In another embodiment, the kit for the identification of a subject suitable for application of the specific anti-c-Met antibody may further include at least one selected from the group consisting of a Cbl detection agent for determining a Cbl concentration, an agent for detecting a Cbl mutation, and an agent for detecting a c-Met mutation. That is, the kit includes:

an LRIG1 detection agent for determining an LRIG1 level;

at least one selected from the group consisting of a Cbl detection agent for determining a Cbl concentration, an agent for detecting a Cbl mutation, and an agent for detecting a c-Met mutation; and a detection means.

The Cbl detection agent for determining a Cbl concentration may be selected from the group consisting of an anti-Cbl antibody, an aptamer specifically binding to Cbl, and a combination thereof. The agent for detecting a Cbl mutation may be selected from the group consisting of a primer capable of detecting the Cbl mutation (a 20- to 50-mer nucleotide sequence including a mutation region of the mutated Cbl gene and/or a complementary sequence thereto), an anti-Cbl antibody specifically binding to a mutated Cbl, and an aptamer specifically binding to a mutated Cbl. The agent for detecting a c-Met mutation may be selected from the group consisting of a probe, a primer capable of detecting the mutation, an anti-c-Met antibody specifically binding to a mutated c-Met, and an aptamer specifically binding to a mutated c-Met. The probe and the primer capable of detecting the mutation are as described above.

The detection means useful in the kit may be that conventionally used in determining an LRIG1 level and/or a Cbl concentration, a Cbl mutation, or a c-Met mutation. A person having ordinary skill in the art to which the present invention pertains can readily take a suitable detection means.

In accordance with still another aspect thereof, the present invention addresses a method for inhibiting c-Met activity, including administering a pharmaceutically effective amount of the specific anti-c-Met antibody to the identified subject.

In accordance with yet a further aspect thereof, the present invention addresses a method for the prophylaxis and/or therapy of c-Met-related diseases, including administering a pharmaceutically effective amount of the specific anti-c-Met antibody to a subject in need thereof.

The methods for inhibiting c-Met activity or for preventing and/or treating c-Met-related diseases may further include identifying a subject suitable for application of the specific anti-c-Met antibody, ahead of the administering step.

This identifying step is the same as in the methods for identifying a subject suitable for treatment with anti-c-Met antibody described above. Thus, it can be carried out in the same manner as in the identifying method, for example, by conducting the step described in the method or by confirming the cell or the patient selected by the identifying method.

In one embodiment, the method for inhibiting c-Met activity or for the prophylaxis or therapy of c-Met-related diseases includes:

identifying a subject suitable for application of the specific anti-c-Met antibody; and administering a pharmaceutically effective amount of the specific anti-c-Met antibody to the subject.

In another embodiment, the method for inhibiting c-Met activity or for the prophylaxis or therapy of c-Met-related diseases includes:

(1) determining an LRIG1 level in a cell sample;

(2) determining the cell or the patient from which the cell sample is originated as a subject suitable for application of the specific anti-c-Met antibody when LRIG1 is present in the cell sample; and (3) administering an effective amount of the specific anti-c-Met antibody to the cell or the patient, wherein the LRIG1 level is determined as a stain intensity of '+2' or '+3' as analyzed by immunohistochemical staining using an anti-LRIG1 antibody.

In another embodiment, the method for inhibiting c-Met activity or for the prophylaxis or therapy of c-Met-related diseases includes:

(1) determining an LRIG1 level in a cell sample;

(1-1) determining a Cbl concentration, a Cbl mutation, and/or a mutation of a site of c-Met for interaction with Cbl in the cell sample;

(2) determining the cell or the patient from which the cell sample is originated as a subject suitable for application of the specific anti-c-Met antibody when Cbl is absent or present at a low level in the cell sample or when a mutation is present on Cbl and/or the site of c-Met for interaction with Cbl, with a proviso that LRIG1 is present in the cell sample; and (3) administering an effective amount of the specific anti-c-Met antibody to the cell or the patient, wherein the LRIG1 level is determined as a stain intensity of '+2' or '+3' as analyzed by immunohistochemical staining using an anti-LRIG1 antibody, and the Cbl concentration is determined as a stain intensity of '−' or '+1' as analyzed by immunohistochemical staining using an anti-Cbl antibody.

In another embodiment, the method for inhibiting c-Met activity or for the prophylaxis or therapy of c-Met-related diseases includes:

(1) determining an LRIG1 level in a cell sample;

(1-1') determining a Cbl concentration in the cell sample;

(2') determining the cell or the patient from which the cell sample is originated as a subject suitable for application of the specific anti-c-Met antibody when Cbl is absent or present at a low level in the cell sample, with a proviso that LRIG1 is present in the cell sample, and (3) administering an effective amount of the specific anti-c-Met antibody to the cell or the patient.

Wherein the presence of LRIG1 may be the case that the LRIG1 level is determined as a stain intensity of '+2' or '+3' as analyzed by immunohistochemical staining using an anti-LRIG1 antibody, and the absence or presence at a low level of Cbl may be the case that the Cbl concentration is determined as a stain intensity of '−' or '+1' as analyzed by immunohistochemical staining using an anti-Cbl antibody.

In another embodiment, the method for inhibiting c-Met activity or for the prophylaxis or therapy of c-Met-related diseases includes:

(1) determining an LRIG1 level in a cell sample;

(1-1") determining the presence of a mutation on a Cbl protein or a Cbl gene coding for the Cbl protein in the cell sample;

(2") determining the cell or the patient from which the cell sample is originated as a subject suitable for application of the specific anti-c-Met antibody if LRIG1 is present in the cell sample when a mutation is present on the Cbl protein or the Cbl gene; and (3) administering an effective amount of the specific anti-c-Met antibody to the cell or the patient.

Wherein the presence of LRIG1 may be the case that the LRIG1 level is determined as a stain intensity of '+2' or '+3' as analyzed by immunohistochemical staining using an anti-LRIG1 antibody.

In another embodiment, the method for inhibiting c-Met activity or for the prophylaxis or therapy of c-Met-related diseases includes:

(1) determining an LRIG1 level in a cell sample;

(1-1''') determining the presence of a mutation on a site of c-Met for interaction with Cbl or on a region of c-Met gene corresponding to the site of c-Met for interaction with Cbl in the cell sample;

(2''') determining the cell or the patient from which the cell sample is originated as a subject suitable for application of the specific anti-c-Met antibody if LRIG1 is present in the cell sample when a mutation is present on the site of c-Met for interaction with Cbl or on the region of C-met gene corresponding to the c-Met site; and (3) administering an effective amount of the specific anti-c-Met antibody to the cell or the patient.

LRIG1 is considered to be present when the LRIG1 level is determined as a stain intensity of '+2' or '+3' as analyzed by immunohistochemical staining using an anti-LRIG1 antibody.

In the method for the prophylaxis and/or therapy of c-Met-related diseases, as described above, the step (1), (1'), (1"), or (1''') may be carried out ahead of or behind the step (1-1), (1-1'), (1-1"), or (1-1'''). In addition, the step (1-1), (1-1'), (1-1"), or (1-1''') may be performed on a subject suitable for application of the anti-c-Met antibody, identified by the steps (1) and (2), and the method may further include the step (1-1), (1-1'), (1-1"), or (1-1''') of determining an LRIG1 level in the cell sample may be carried ahead of the step (2), (2'), (2"), or (2''').

The specific anti-c-Met antibody of the present invention is used by being applied to the subject. Thus, the use of the specific anti-c-Met antibody of the present invention in application to the subject forms an aspect of the present invention. In detail, the present invention provides the use of the specific anti-c-Met antibody in application or administration to a cell or a patient in which a level of LRIG1 is determined as a stain intensity of '+2' or '+3' as analyzed by immunohistochemical staining using an anti-LRIG1 antibody, thereby inhibiting c-Met activity or treating a c-Met-related disease. The c-Met-related disease is as described above.

In one embodiment, the present invention provides the use of the specific anti-c-Met antibody in application or administration to a cell or a patient in which Cbl is absent or present at a low level (e.g., the Cbl concentration is determined as a stain intensity of '−' or '+' as analyzed by immunohistochemical staining using an anti-Cbl antibody) and/or in which a functional mutation is present on a Cbl protein or a Cbl gene and/or in which a mutation is present on a site of c-Met for interaction with Cbl or on a region of c-Met gene corresponding to the site of c-Met for interaction with Cbl, with the proviso that LRIG1 is present in the cell sample (e.g., the level of LRIG1 in the cell sample is determined as a stain intensity of '+2' or '+3' as analyzed by immunohistochemical staining using an anti-LRIG1 antibody), thereby inhibiting c-Met activity or treating a c-Met-related disease.

In another embodiment, the present invention provides the use of the specific anti-c-Met antibody in preparing a drug applicable to a cell in which LRIG1 is present (e.g., the level of LRIG1 in the cell sample is determined as a stain intensity of '+2' or '+3' as analyzed by immunohistochemical staining using an anti-LRIG1 antibody). The drug may be a c-Met inhibitor or a therapeutic for a c-Met-related disease.

In another embodiment, the present invention provides the use of the specific anti-c-Met antibody in preparing a c-Met inhibitor and/or a therapeutic for a c-Met-related disease, applicable or administrable to a cell or a patient in which Cbl is absent or present at a low level (e.g., the Cbl concentration is determined as a stain intensity of '−' or '+1' as analyzed by immunohistochemical staining using an anti-Cbl antibody) and/or in which a functional mutation is present on a Cbl protein or a Cbl gene and/or in which a mutation is present on a site of c-Met for interaction with Cbl or on a region of a c-Met gene corresponding to the site of c-Met for interaction with Cbl, with the proviso that LRIG1 is present in the cell sample (e.g., the level of LRIG1 in the cell sample is determined as a stain intensity of '+2' or '+3' as analyzed by immunohistochemical staining using an anti-LRIG1 antibody).

The term "c-Met-related disease" refers to any disease caused by the expression or overexpression of c-Met. Cancer is representative of a c-Met-related disease. Examples of the cancer include squamous cell carcinoma, small cell lung cancer, non-small cell lung cancer, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, chronic or acute leukemia, lymphocyte lymphoma, hepatoma, stomach cancer, pancreatic cancer, glioblastoma, cervical cancer, ovarian cancer, liver cancer, bladder cancer, hepatic tumor, breast cancer, colon cancer, large intestine cancer, endometrial cancer, uterine cancer, salivary gland cancer, renal cancer, prostate cancer, vulvar cancer, thyroid cancer, and head and neck cancer, but are not limited thereto. Gestational diabetes also falls within the scope of c-Met-related diseases.

The term "pharmaceutically effective amount" or "therapeutically effective amount" means a dosage of a particular active agent, in this case the specific anti-c-Met antibody, to exhibit a desired effect, for instance inhibiting (degrading) c-Met, and preventing or treating c-Met-related diseases in a subject in need thereof, and may vary depending on various factors including a desired result, kinds of diseases or symptoms, the severity of illness, the route of administration, dosage forms, etc.

As described above, "c-Met" or "c-Met protein" is receptor tyrosine kinase (RTK) which binds hepatocyte growth factor (HGF). c-Met may be a c-Met protein from any species, particularly a mammal, for instance, primates such as human c-Met (e.g., NP_000236), or monkey c-Met (e.g., *Macaca mulatta*, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various mechanisms, such as cancer development, metastasis, migration of cancer cell, invasion of cancer cell, angiogenesis, and the like.

The anti-c-Met antibody may also include a variant of the antibody. The variant of the antibody may be any isotypes of antibodies derived from human and other animals and/or one including any Fc region of antibodies (e.g., IgA, IgD, IgE, IgG (IgG1, IgG2, IgG3, or IgG4), IgM, and the like) derived from human and other animals, having mutated hinge wherein at least one amino acid is changed, deleted or added. Unless stated otherwise, the anti-c-Met antibody may include the variants of the antibody as well as the antibody with no variation.

The antigen binding fragment of the anti-c-Met antibody may refer to a fragment including an antigen binding region of the anti-c-Met antibody, and be selected from the group consisting of a complementarity determining region (CDR), fragment including CDR and Fc region, scFv, (scFv)2, Fab, Fab', and F(ab')2 of the anti-c-Met antibody.

Unless stated otherwise, the term "specific anti-c-Met antibody," as used herein, may be intended to mean an antibody or an antigen-binding fragment. The specific anti-c-Met antibody may recognize a specific region of c-Met, e.g., a specific region of the SEMA domain, as an epitope. It may be any antibody or antigen-binding fragment that acts on c-Met to induce c-Met intracellular internalization and degradation.

c-Met, a receptor for hepatocyte growth factor, may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from a.a. 106 to a.a. 124, is a loop region between the second and the third propellers within the epitopes of the SEMA domain. It acts as an epitope for the specific anti-c-Met antibody of the present invention.

The term "epitope," as used herein, refers to an antigenic determinant, a part of an antigen recognized by an antibody. In one embodiment, the epitope may be a region including 5 or more consecutive amino acid residues within the SEMA domain (SEQ ID NO: 79) of c-Met protein, for instance, 5 to 19 consecutive amino acid residues corresponding to a range from 106th amino acid to 124th amino acid within the SEMA domain (SEQ ID NO: 79) of a c-Met protein. For example, the epitope may be a polypeptide having 5 to 19 consecutive amino acids selected from among partial combinations of the amino acid sequence of SEQ ID NO: 71, with the amino sequence of SEQ ID NO: 73 (EEPSQ) serving as an essential element for the epitope. For example, the epitope may be a polypeptide including the amino acid sequence of SEQ ID NO: 71, SEQ ID NO: 72, or SEQ ID NO: 73. As used herein, the term "consecutive amino acid residues" refers to amino acid residues positioned consecutively in the amino acid sequence or three-dimensional structure.

The epitope having the amino acid sequence of SEQ ID NO: 72 corresponds to the outermost part of the loop between the second and third propellers within the SEMA domain of a c-Met protein, the epitope having the amino acid sequence of SEQ ID NO: 73 is a site to which the antibody or antigen-binding fragment according to one embodiment of the present invention most specifically binds.

Thus, the specific anti-c-Met antibody may specifically bind to an epitope which has 5 to 19 consecutive amino acids, selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the specific anti-c-Met antibody may be an antibody or antigen-binding fragment which includes:

a heavy chain variable region including the amino acid sequence of at least one heavy chain complementarity determining region (CDR) selected from the group consisting of CDR-H1 including the amino acid sequence of SEQ ID NO: 4; CDR-H2 including the amino acid sequence of SEQ ID NO: 5 or SEQ ID NO: 2, or including an amino acid sequence of 8 to 19 consecutive amino acids including amino acid residues from 3rd to 10th positions within the amino acid sequence of SEQ ID NO: 2; and CDR-H3 including the amino acid sequence of SEQ ID NO: 6 or SEQ ID NO: 85, or including an amino acid sequence of 6 to 13 consecutive amino acids including amino acid residues from 1st to 6th positions within the amino acid sequence of SEQ ID NO: 85; and a light chain variable region including the amino acid sequence of at least one light chain complementarity determining region (CDR) selected from the group consisting of CDR-L1 including the amino acid sequence of SEQ ID NO: 7, CDR-L2 including the amino acid sequence of SEQ ID NO: 8, and CDR-L3 including the amino acid sequence of SEQ ID NO: 9 or SEQ ID NO: 86, or including an amino acid sequence of 9 to 17 consecutive amino acids including amino acid residues from 1st to 9th positions within the amino acid sequence of SEQ ID NO: 89.

Herein, the amino acid sequences of SEQ ID NOS: 4 to 9 are respectively represented by following Formulas I to VI, below:

```
Formula I
Xaa1-Xaa2-Tyr-Tyr-Met-Ser,      (SEQ ID NO: 4)
``` wherein Xaa1 is absent or Pro or Ser, and Xaa2 is Glu or Asp,

```
Formula II
                                (SEQ ID NO: 5)
Arg-Asn-Xaa3-Xaa4-Asn-Gly-Xaa5-Thr,
``` wherein Xaa3 is Asn or Lys, Xaa4 is Ala or Val, and Xaa5 is Asn or Thr,

```
Formula III
Asp-Asn-Trp-Leu-Xaa6-Tyr,      (SEQ ID NO: 6)
``` wherein Xaa6 is Ser or Thr,

```
Formula IV
                                (SEQ ID NO: 7)
Lys-Ser-Ser-Xaa7-Ser-Leu-Leu-Ala-Xaa8-Gly-Asn-
Xaa9-Xaa10-Asn-Tyr-Leu-Ala
``` wherein Xaa7 is His, Arg, Gln, or Lys, Xaa8 is Ser or Trp, Xaa9 is His or Gln, and Xaa10 is Lys or Asn,

```
Formula V
Trp-Xaa11-Ser-Xaa12-Arg-Val-Xaa13   (SEQ ID NO: 8)
``` wherein Xaa11 is Ala or Gly, Xaa12 is Thr or Lys, and Xaa13 is Ser or Pro, and

```
Formula VI
                                (SEQ ID NO: 9)
Xaa14-Gln-Ser-Tyr-Ser-Xaa15-Pro-Xaa16-Thr
``` wherein Xaa14 is Gly, Ala, or Gln, Xaa15 is Arg, His, Ser, Ala, Gly, or Lys, and Xaa16 is Leu, Tyr, Phe, or Met.

In one embodiment, the CDR-H1 may have an amino acid sequence selected from the group consisting of SEQ ID NOS: 1, 22, 23, and 24. The CDR-H2 may have an amino acid sequence selected from the group consisting of SEQ ID NOS: 2, 25, and 26. The CDR-H3 may have an amino acid sequence selected from the group consisting of SEQ ID NOS: 3, 27, 28, and 85.

The CDR-L1 may have an amino acid sequence selected from the group consisting of SEQ ID NOS: 10, 29, 30, 31, 32, 33, and 108. The CDR-L2 may have an amino acid sequence selected from the group consisting of SEQ ID NOS: 11, 34, 35, and 36. The CDR-L3 may have an amino acid sequence selected from the group consisting of SEQ ID NOS: 12, 13, 14, 15, 16, 37, 86, and 89.

In another embodiment, the antibody or antigen-binding fragment of the present invention includes a heavy variable region including a polypeptide (CDR-H1) having an amino acid sequence selected from the group consisting of SEQ ID NOS: 1, 22, 23, and 24, a polypeptide (CDR-H2) having an amino acid sequence selected from the group consisting of SEQ ID NOS: 2, 25, and 26, and a polypeptide (CDR-H3) having an amino acid sequence selected from the group consisting of SEQ ID NOS: 3, 27, 28, and 85; and a light variable region including a polypeptide (CDR-L1) having an amino acid sequence selected from the group consisting of SEQ ID NOS: 10, 29, 30, 31, 32, 33 and 108, a polypeptide (CDR-L2) having an amino acid sequence selected from the group consisting of SEQ ID NOS: 11, 34, 35, and 36, and a polypeptide (CDR-L3) having an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies are developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDR of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti-c-Met antibodies may be mouse-derived antibodies, mouse-human chimeric antibodies, humanized antibodies, or human antibodies. The antibodies or antigen-binding fragments thereof may be isolated from a living body.

The antibody may be a monoclonal antibody. The monoclonal antibody may be produced from a hybridoma of Accession No. KCLRF-BP-00220 deposited on Oct. 6, 2009, at the Korean Cell Line Research Foundation located at the Cancer Research Institute, Seoul National University College of Medicine, 28 Yongon-gong, Chongno-Gu, Seoul, 110-744, Korea.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region VH that includes amino acid sequences sufficient to provide specificity to antigens, and three constant regions, CH1, CH2, and CH3, and a hinge. The term "light chain" refers to a full-length light chain and fragments thereof, including a variable region VL that includes amino acid sequences sufficient to provide specificity to antigens, and a constant region CL.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" or "specifically recognized" is well known to one of ordinary skill in the art, and indicates that an antibody and an antigen specifically interact with each other to lead to an immunological activity.

In one embodiment, the antibody may be an antigen-binding fragment selected from the group consisting of scFv, (scFv)2, Fab, Fab', and F(ab')2.

The term "antigen-binding fragment" used herein refers to fragments of an intact immunoglobulin including portions of a polypeptide including antigen-binding regions having the ability to specifically bind to the antigen. For example, the antigen-binding fragment may be scFv, (scFv)2, Fab, Fab', or F(ab')2, but is not limited thereto. Among the antigen-binding fragments, Fab that includes light chain and heavy chain variable regions, a light chain constant region, and a first heavy chain constant region CH1, has one antigen-binding site.

The Fab' fragment is different from the Fab fragment, in that Fab' includes a hinge region with at least one cysteine residue at the C-terminal of CH1.

The F(ab')2 antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The antigen-binding fragments may be attainable using protease (for example, the Fab fragment may be obtained by restricted cleavage of a whole antibody with papain, and the F(ab')2 fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the specific anti-c-Met antibody or an antigen-binding fragment thereof may be modified by the deletion, addition, or substitution of at least one amino acid residue on the amino acid sequence of the hinge region so that it exhibit enhanced antigen-binding efficiency. For example, the antibody may include a hinge region having the amino acid sequence of SEQ ID NO: 100, 101, 102, 103, 104, or 105. Preferably, the hinge region has the amino acid sequence of SEQ ID NO: 100 or 101.

In one embodiment of the specific anti-c-Met antibody or antigen-binding fragment, the variable domain of the heavy chain includes the amino acid sequence of SEQ ID NO: 17, 74, 87, 90, 91, 92, 93, or 94 and the variable domain of the light chain includes the amino acid sequence of SEQ ID NO: 18, 19, 20, 21, 75, 88, 95, 96, 97, 98, 99 or 109.

In one embodiment, the specific anti-c-Met antibody is a monoclonal antibody, produced by the hybridoma cell line deposited with Accession No. KCLRF-BP-00220, binding specifically to the extracellular region of c-Met protein (refer to Korean Patent Publication No. 2011-0017698, the disclosure of which is incorporated in its entirety herein by reference).

The specific anti-c-Met antibody may include any of the antibodies defined in Korean Patent Publication No. 2011-0017698, which is incorporated herein by reference.

By way of further example, the anti-c-Met antibody or antibody fragment may include a heavy chain including the amino acid sequence of SEQ ID NO: 62 (wherein the amino acid sequence from 1st to 17th is a signal peptide) or the amino acid sequence from 18th to 462nd of SEQ ID NO: 62 and a light chain including the amino acid sequence of SEQ ID NO: 68 (wherein the amino acid sequence from 1st to 20th is a signal peptide) or the amino acid sequence from 21st to 240th of SEQ ID NO: 68; or a heavy chain including the amino acid sequence of SEQ ID NO: 64 (wherein the amino acid sequence from 1st to 17th is a signal peptide) or the amino acid sequence from 18th to 461st of SEQ ID NO: 64 and a light chain including the amino acid sequence of SEQ ID NO: 68 or the amino acid sequence from 21st to 240th of SEQ ID NO: 68; or a heavy chain including the amino acid sequence of SEQ ID NO: 66 (wherein the amino acid sequence from 1st to 17th is a signal peptide) or the amino acid sequence from 18th to 460th of SEQ ID NO: 66 and a light chain including the amino acid sequence of SEQ ID NO: 68 or the amino acid sequence from 21st to 240th of SEQ ID NO: 68.

Additional examples of anti-c-Met antibodies include those in which the anti-c-Met antibody includes a heavy chain including the amino acid sequence of SEQ ID NO: 62 or the amino acid sequence from 18th to 462nd of SEQ ID NO: 62 and a light chain including the amino acid sequence of SEQ ID NO: 70 (wherein the amino acid sequence from 1st to 20th is a signal peptide) or the amino acid sequence from 21st to 240th of SEQ ID NO: 70; a heavy chain including the amino acid sequence of SEQ ID NO: 64 or the amino acid sequence from 18th to 461st of SEQ ID NO: 64 and a light chain including the amino acid sequence of SEQ ID NO: 70 or the amino acid sequence from 21st to 240th of SEQ ID NO: 70; or a heavy chain including the amino acid sequence of SEQ ID NO: 66 or the amino acid sequence from 18th to 460th of SEQ ID NO: 66 and a light chain including the amino acid sequence of SEQ ID NO: 70 or the amino acid sequence from 21st to 240th of SEQ ID NO: 70.

In still other examples, the anti-c-Met antibody may include a heavy chain including the amino acid sequence of SEQ ID NO: 62 or the amino acid sequence from 18th to 462nd of SEQ ID NO: 62 and a light chain including the amino acid sequence of SEQ ID NO: 110; a heavy chain including the amino acid sequence of SEQ ID NO: 64 or the amino acid sequence from 18th to 461st of SEQ ID NO: 64 and a light chain including the amino acid sequence of SEQ ID NO: 110; or a heavy chain including the amino acid sequence of SEQ ID NO: 66 or the amino acid sequence from 18th to 460th of SEQ ID NO: 66 and a light chain including the amino acid sequence of SEQ ID NO: 110.

In an embodiment, the anti-c-Met antibody may include a heavy chain including the amino acid sequence from 18th to 460th of SEQ ID NO: 66 and a light chain including the amino acid sequence from 21st to 240th of SEQ ID NO: 68; or a heavy chain including the amino acid sequence from 18th to 460th of SEQ ID NO: 66 and a light chain including the amino acid sequence of SEQ ID NO: 110.

The specific anti-c-Met or the antigen-binding fragment thereof according to the present invention may be used in a pharmaceutical composition. Accordingly, a pharmaceutical composition including a pharmaceutically effective amount of the specific anti-c-Met or the antigen-binding fragment thereof, optionally together with a pharmaceutically acceptable vehicle, a diluent, and/or an excipient, form yet another aspect of the present invention.

So long as it is usually used in drug formulations, any pharmaceutically acceptable vehicle may be contained in the pharmaceutical composition including the anti-c-Met antibody according to the present invention. Examples of the pharmaceutically acceptable vehicle available for the pharmaceutical composition of the present invention include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propylhydroxybenzoate, talc, magnesium stearate, and mineral oil, but are not limited thereto. The pharmaceutical composition may further include an additive selected from the group consisting of a diluent, an excipient, a lubricant, a wetting agent, a sweetener, a flavorant, an emulsifier, a suspending agent, a preservative, and a combination thereof.

The specific anti-c-Met or the pharmaceutical composition including a pharmaceutically effective amount thereof may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because the peptides are digested by pepsin. In addition, the administration may be performed with the aid of an instrument adapted for delivering the pharmaceutical composition to target cells.

The effective amount may vary depending on various factors including the type of formulation, the patient's age, weight, and sex, the severity of the disorder being treated, diet, the time of administration, the route of administration, the rate of excretion, and sensitivity. For example, the composition of the present invention may be administered at a single dose raging from about 0.001 mg to about 100 mg for adults, for example, from about 0.001 mg to about 0.1 mg, from about 0.1 mg to about 1 mg, from about 1 mg to about 10 mg, or from about 10 mg to about 100 mg.

According to a method that is well known to those skilled in the art, the anti-c-Met antibody or the pharmaceutical composition of the present invention may be formulated, together with pharmaceutically acceptable carriers and/or excipients, into unit dose forms, or may be included within a multiple dose package. In this context, the pharmaceutical composition may be formulated into solutions in oil or aqueous media, suspensions, syrup, emulsions, elixirs, powders, granules, tablets, or capsules, and may further include a dispersant or a stabilizer.

The anti-c-Met antibody or the pharmaceutical composition of the present invention may be administered alone or in combination with other therapeutics. In this case, they are administered sequentially or simultaneously together with conventional therapeutics.

The composition including an antibody or an antigen-binding fragment can be formulated into immunoliposomes. Liposomes including an antibody may be prepared using methods that are well-known in the art. The immunoliposomes may be produced from a lipid composition including phosphatidylcholine, cholesterol, and PEGylated phosphatidylethanolamine by reverse-phase evaporation. To quote an example, Fab' may be conjugated to liposomes by disulfide reformation. The liposome may further contain an anticancer agent such as doxorubicin.

In one embodiment, the antibody may act as an antagonist of c-Met protein.

As used herein, the term "antagonist" is intended to encompass all molecules that at least partially block, suppress, or neutralize at least one of the biological activities of a target (e.g., c-Met). By way of example, an "antagonist" antibody means an antibody that represents suppression or inhibition against the biological activity of the antigen to which the antibody binds (e.g., c-Met). An antagonist may function to reduce ligand-induced receptor phosphorylation or to incapacitate or kill cells which have been activated by ligands. Also, an antagonist may completely interfere with receptor-ligand interaction or substantially reduce the interaction by changing the three-dimensional structure of the receptor or by down regulation.

According to the present invention, the specific anti-c-Met antibody exerts Cbl-independent c-Met degradation and/or a therapeutic effect on c-Met-related antibodies in the cells (cancer cells) or cancer patients having a level of LRIG1 in which conventional anti-c-Met antibodies cannot trigger c-Met degradation due to the absence or presence at a low level of Cbl or a mutation on Cbl or c-Met. Hence, the present invention enables a tailored treatment pertinent to patients of c-Met-related diseases which cannot be treated with conventional anti-c-Met antibodies, expanding the choice of application of the specific anti-c-Met antibody.

The Cbl enzyme (E3 ligase) is a negative regulator which functions to translocate c-Met from the cell membrane into the cytoplasm and degrade c-Met. Representative among Cbl enzymes are E3A and mdm2 anaphase-promoting complex (APC). Cbl is known to be involved in the down regulation of the receptor tyrosine kinase (RTK) family including EGFR and ErbB3 as well as c-Met. Whereas conventional anti-c-Met antibodies show Cbl-mediated anticancer effects, the specific anti-c-Met antibody of the present invention triggers the down regulation of c-Met through the Cbl-independent, LRIG1-mediated pathway.

The down regulation of c-Met through the LRIG1 pathway operates independently of Cbl. In addition, because the LRIG1-mediated down-regulation of c-Met does not involve the proteasome pathway, it allows c-Met to be degraded through the lysosomal pathway even though factors involved in proteasome formation, including Cbl, are damaged. Accordingly, the specific anti-c-Met antibody of the present invention can trigger c-Met degradation and thus can provide a therapy for c-Met-related diseases even when factors involved in proteasome formation, such as Cbl, are dysfunctional because the antibody-triggered down-regulation of c-Met takes an LRIG1-mediated pathway. In contrast, because the mechanism of LRIG1-mediated c-Met degradation is independent of the activation of c-Met, the specific anti-c-Met antibody, which takes advantage of the LRIG1-mediated pathway, eliminates the problems associated with conventional anti-c-Met antibodies, which are Cbl-mediated.

The specific anti-c-Met antibody of the present invention is able to induce the association of LRIG1 with c-Met independently of Cbl in cancer patients in which a high level of LRIG1 is expressed. In this context, when the intracellular level of LRIG1 is determined, the efficacy of the specific anti-c-Met antibody can be evaluated in advance, which allows for tailored treatment according to personal characteristics of patients.

In addition, the present invention can identify a subject suitable for application of the specific anti-c-Met antibody by use of a very small amount of proteins or RNA, thus enjoying advantages in terms of the cost, time, and efficacy of anticancer therapy.

Also provided is a method of treating cancer in a subject, the method comprising administering an antibody or antigen-binding fragment thereof that specifically binds to an epitope within a SEMA domain of a c-Met protein to the subject, wherein the cancer is characterized by (a) the presence of LRIG1 and (b) low or absent Cbl expression levels or a mutation in Cbl or c-Met that inhibits interaction between Cbl and c-Met cancer; or wherein the cancer is resistant to treatment with EGFR-targeted therapy. The method may further comprise the steps of (i) detecting or otherwise confirming the presence of LRIG1 in a cell or sample of the cancer from the subject, and/or (ii) determining that expression of Cbl in a cell or sample or the cancer from the subject is low, or detecting a mutation in Cbl or c-Met that inhibits interaction between Cbl and c-Met. All other aspects of this method are as described with respect to other methods provided herein.

LRIG1 is known as a negative regulator of c-Met, but mechanism of LRIG1 association with c-Met has remained unknown. In the present invention, experiments demonstrated that the specific anti-c-Met antibody induces the association of LRIG1 with c-Met in cells (especially cancer cells) and thus effective c-Met degradation, thereby bringing about a therapeutic effect on c-Met-related diseases, e.g., an anticancer effect.

Further, the anticancer effect of the specific anti-c-Met antibody of the present invention was not detected in siRNA-mediated LRIG1 knockdown models, indicating that the expression of LRIG1 is an important factor that is predictive of the workability of the specific anti-c-Met antibody. Even in the case of the up-regulation of c-Met or drug resistance due to abnormal Cbl, the application of the specific anti-c-Met antibody can be determined according to the absence or presence of LRIG1.

As stated previously, Cbl, although serving as a main E3 ligase to induce the quantitative reduction of c-Met, interacts with only activated c-Met and is thus highly apt to cause an adverse effect (agonism). The specific anti-c-Met antibody of the present invention cannot induce interaction between c-Met and Cbl in NCI-H441 lung cancer cells while the conventional antibody 5D5 increased the interaction under the same conditions (refer to FIG. 2A). This result elucidates the high adverse effect (agonism) of 5D5.

Figure 4A:
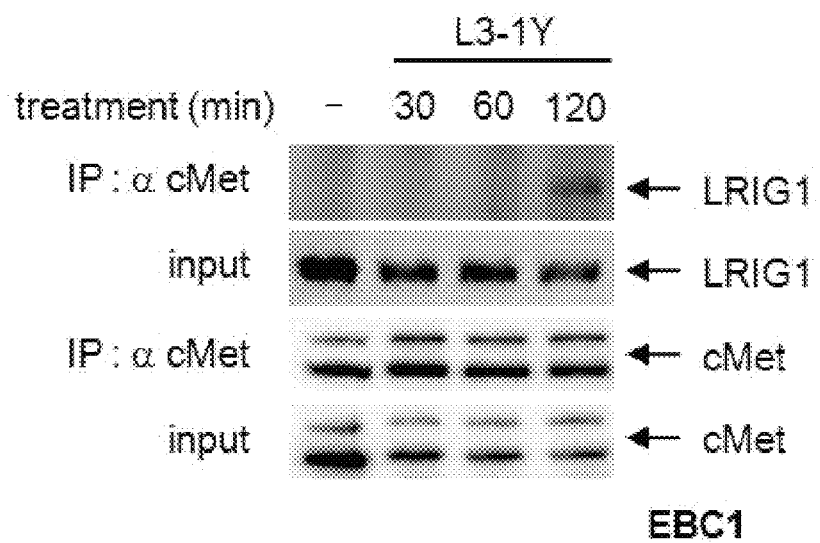

Further, LRIG1 can associate with c-Met irrespective of the presence or absence of HGF that is involved in the activation of c-Met. In the lung cancer cell line EBC-1, the specific anti-c-Met antibody induced the association of LRIG1 with c-Met, whereas the conventional antibody 5D5 cannot. This result was also observed in HEK293 cells (refer to FIGS. 4A and 4B). Thus, the specific anti-c-Met antibody allows effective c-Met degradation and brings about an effective therapy for c-Met-related diseases without the adverse effect attributed to the activation of c-Met.

The lung cancer cell line EBC-1 can be suitable for use in observing anticancer efficacy upon the siRNA-mediated knockdown of LRIG1 because it expresses LRIG1 at a high level and in observing a Cbl-independent anticancer efficacy because it expresses Cbl at a very low level. Cell proliferation assays and apoptosis assays have shown that the specific anti-c-Met antibody of the present invention have excellent anticancer effects on EBC-1 lung cancer cells which expresses Cbl at a low level and LRIG1 at a high level, compared to conventional antibodies. In addition, siRNA-mediated LRIG1 knockdown EBC-1 lung cancer cells were found to be insensitive to the specific anti-c-Met antibody (refer to FIG. 4E).

An examination was made to see the c-Met degradation pathway induced by the specific anti-c-Met antibody. Since the proteasome pathway is accompanied by poly-ubiquitination, an ubiquitination assay was conducted to examine whether the anti-c-Met antibody-induced c-Met degradation undergoes the proteasome pathway. When poly-ubiquitination takes place in a protein, the protein can be detected by, for example, immunoblotting. While being treated with the anti-c-Met antibody 5D5 or the specific anti-c-Met antibody, EBC-1 or NCI-H441 cancer cells were monitored as to the poly-ubiquitination of c-Met. The conventional anti-c-Met antibody 5D5 was observed to induce poly-ubiquitination whereas the specific anti-c-Met antibody could not (refer to FIGS. 3A and 3B).

The data thus obtained demonstrate that the specific anti-c-Met antibody triggers c-Met degradation through a pathway other than the proteasome pathway. When concanamycin, known to block the lysosomal pathway, was used, the c-Met degradation triggered by the specific anti-c-Met antibody was decreased, indicating that the specific anti-c-Met antibody induces the association of LRIG1 with c-Met and utilizes the lysosomal pathway in c-Met degradation (refer to FIG. 4F).

One or more embodiments of the present invention will now be described in further detail with reference to the following Examples. However, these examples are for the illustrative purposes only and are not intended to limit the scope of the invention.

REFERENCE EXAMPLE 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tail and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in water at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Like this, hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at 28 Yongon-gong, Chongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody were produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a CO2 incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mice antibody AbF46 produced in Example 1 by replacing the constant region, but not the variable region responsible for antibody specificity, with an amino sequence of human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the vectors thus constructed was amplified with the aid of a Qiagen Maxiprep kit (Cat no. 12662). The vectors which respectively carried the heavy chain and the light chain were co-transfected at a ratio of 4:1 (80 µg:20 µg) into 293T cells (2.5×107). The transfection into 293T cells (2.5×107) was performed in the presence of 360 µL of 2M CaCl2.

Afterwards, the cells were incubated in DMEM supplemented with 10% (v/v) FBS for 5 hours at 37° C. under a 5%

CO2 condition and then in FBS-free DMEM for 48 hours at 37° C. under a 5% CO2 condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest homology with the VH gene of the mouse antibody AbF46 purified in Reference Example 1.2 were analyzed. An Ig BLAST result revealed that VH3-71 has a homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a search for BLAST. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest homology with the VH gene of the mouse antibody AbF46 were analyzed. An Ig BLAST search result revealed that VK4-1 has a homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest homology with the VL gene of the mouse antibody AbF46 were analyzed by a search for BLAST. As a result, VK2-40 was selected as well. VL and VK2-40 of the mouse antibody AbF46 were found to have a homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy; SEQ ID NO: 47, H3-heavy; SEQ ID NO: 48, H4-heavy; SEQ ID NO: 49) and DNA fragments having the light chain nucleotide sequences (H1-light; SEQ ID NO: 50, H2-light; SEQ ID NO: 51, H3-light; SEQ ID NO: 52, H4-light; SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the recombinant vectors was amplified using Qiagen Maxiprep kit (Cat no. 12662). The vectors which respectively carried the heavy chain and the light chain were co-transfected at a ratio of 4:1 (80 µg:20 µg) into 293T cells (2.5×107). The transfection into 293T cells (2.5×107) was performed in the presence of 360 µL of 2M CaCl2. Afterwards, the cells were incubated in DMEM supplemented with 10% (v/v) FBS for 5 hours at 37° C. under a 5% CO2 condition, and then in FBS-free DMEM for 48 hours at 37° C. under a 5% CO2 condition.

After centrifugation, the supernatant were applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) coding for the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDR and Synthesis of Primer The affinity maturation of huAbF46 was achieved. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |

TABLE 1-continued

| CDR | Amino Acid Sequence |
|---|---|
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of Library of huAbF46 Antibodies and Affinity for c-Met

The construction of antibody gene libraries through the introduction of random sequences was carried out using the primers synthesized in the same manner as in Reference Example 1.5.1. Two PCR products were obtained, as shown in FIGS. 2A-2E, using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides coding for heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences ((DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61)) were digested with EcoRI (NEB, R0101S) and XhoI (NEB, R0146S) before cloning into a pOptiVEC™-TOPO TA Cloning Kit enclosed in an Opti-CHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the recombinant vectors was amplified using a Qiagen Maxiprep kit (Cat no. 12662). The vectors which respectively carried the heavy chain and the light chain were co-transfected at a ratio of 4:1 (80 µg:20 µg) into 293T cells (2.5×107). The transfection into 293T cells (2.5×107) was performed in the presence of 360 µL of 2M CaCl2. Afterwards, the cells were incubated in DMEM supplemented with 10% (v/v) FBS for 5 hours at 37° C. under a 5% CO2 condition and then in FBS-free DMEM for 48 hours at 37° C. under a 5% CO2 condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed into tyrosine in all of the three antibodies to increase antibody production.

For use in constructing the three antibodies, a polynucleotide (SEQ ID NO: 63) coding for a polypeptide (SEQ ID NO: 62) composed of the heavy chain variable region of huAbF46-H4-A1, a U6-HC7 hinge region, and a human IgG1 constant region, a polynucleotide (SEQ ID NO: 65) coding for a polypeptide (SEQ ID NO: 64) composed of the heavy chain variable region of huAbF46-H4-A1, a human IgG2 hinge region, and a human IgG1 region, a polynucleotide (SEQ ID NO: 67) coding for a polypeptide (SEQ ID NO: 66) composed of the heavy chain variable region of huAbF46-H4-A1, a human IgG2 region, and a human IgG2 constant region, and a polynucleotide (SEQ ID NO: 69) coding for a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the vectors thus constructed was amplified with the aid of a Qiagen Maxiprep kit (Cat no. 12662). The vectors which respectively carried the heavy chain and the light chain were co-transfected at a ratio of 4:1 (80 μg:20 μg) into 293T cells (2.5×10$^7$). The transfection into 293T cells (2.5×10$^7$) was performed in the presence of 360 μL of 2M CaCl2. Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Of them, huAbF46-H4-A1 (U6-HC7) was selected as a representative anti-c-Met antibody and used in the following examples. For convenience, it was named anti-c-Met antibody L3-1Y.

REFERENCE EXAMPLE 2

Preparation of Cell Line and Cell Culture

The human stomach cancer cell line MKN45 (JCRB0254) and the lung cancer cell line EBC-1 (JCRB0820) were purchased from the Health Science Research Resource Bank (Shinjuku, Japan), and the kidney cancer cell line Caki-1 (HTB-46), the stomach cancer cell line HS746T (HTB-135), and the human lung adenocarcinoma cell line NCI-H441 (HTB-174) were purchased from the American Type Culture Collection (ATCC, Manassas, Va.).

MKN45, EBC-1, and NCI-H441 cells were maintained in RPMI1640 (GIBCO) while HS746T and Caki-1 cells were cultured in DMEM supplemented with 10% (v/v) fetal bovine serum (FBS, GIBCO) and 1% (v/v) penicillin/streptomycin (GIBCO). Cell culturing was executed at 37° C. in a humidified atmosphere with 5% $CO_2$. Cells were subcultured before reaching confluence and counted using a CEDEX Analyzer (Roche Diagnostics).

EXAMPLE 1

Effect of Anti-c-Met Antibodies on c-Met 1.1. c-Met Degradation in NCI-H441 Cells IgG (negative control, eBioscience), the anti-c-Met antibody L3-1Y constructed in Reference Example 1, and the anti-c-Met antibody 5D5 known as an agonist (separated and purified form ATCC Cat. # HB-11895 hybridoma cells purchased from the American Type Culture Collection (ATCC, Manassas, Va.) (positive control) were tested for c-Met degradation. This test was to examine the efficacy of an antibody by comparing relative changes in total c-Met level, on the basis of the fact that when the antibody binds thereto, c-Met on the cell membrane is internalized and degraded.

NCI-H441 cells were seeded at a density of 2×10$^5$ cells/ml, together with 5 μg/ml of each antibody, into 96-well plates and incubated for 24 hours before cell lysis with the lysis buffer Complete lysis-M (Roche, 04719956001). Total c-Met levels in the cell lysates thus obtained were measured using Human Total HGF R/c-MET ELISA KIT (R&D systems, DYC358) according to the instructions of the manufacturer.

Experiments were performed in triplicate, and mean values of three measurements are presented in FIG. 1A (mean±SD). FIG. 1A shows the ability of antibodies to induce c-Met degradation as expressed as percentages relative to the c-Met level of the IgG treatment group.

As seen in FIG. 1A, NCI-H441 cells were observed to undergo more severe c-Met degradation when treated with the anti-c-Met antibodies L3-1Y and 5D5 than with IgG. In NCIH441 cells rich in Cbl, 5D5 reduced the c-Met level to an extent similar to that of L3-1Y after treatment for 24 hours, but this did not lead to a decrease in cell growth.

1.2. Phosphorylation of c-Met and Downstream Molecule

5D5, a conventional therapeutic anti-c-Met antibody, induces the activation of c-Met (phosphorylation of C-terminal Y1234 or Y1235), which may subsequently cause an adverse effect (agonism), that is, the phosphorylation of downstream molecules Akt and Erk responsible for oncogenesis. Phospho-Akt and phosphor-Erk are known as markers for determining agonism.

To examine adverse effects attributed to the agonism, phosphorylation of kinases downstream of c-Met was measured in NCI-H441 and Caki-1 cells treated with the same antibodies as in Example 1.1.

NCI-H441 and Caki-1 cells were seeded at a density of 2×105 cells/ml into respective 96-well plates and left for 24 hours before treatment with 5 µg/mL of each of the antibodies for 30 min in the absence of serum. The phosphorylation of the downstream kinases was measured using Western blotting.

Figure 1B:
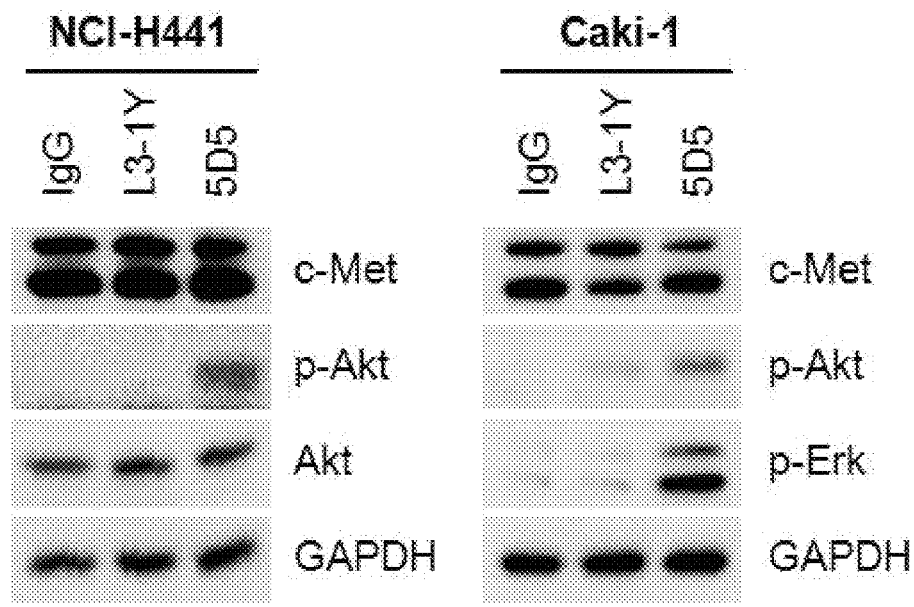

The results are shown in FIG. 1B. As may be seen in FIG. 1B, L3-1Y significantly inhibited the phosphorylation of the downstream molecules in both NCI-H441 and Caki-1 cells, compared to the other antibodies, indicating that the antibody L3-1Y effectively blocks the c-Met signaling pathway. Accordingly, little or no adverse effects are detected in the lung cancer cell line NCI-H441 and the kidney cancer cell line Caki-1 treated with L3-1Y, whereas 5D5 causes significant adverse effects. The data shows that an anti-c-Met antibody which targets c-Met in a Cbl-independent manner promises an anticancer effect without side effects.

1.3. c-Met Degradation in MKN45 Cell

Figure 1C:
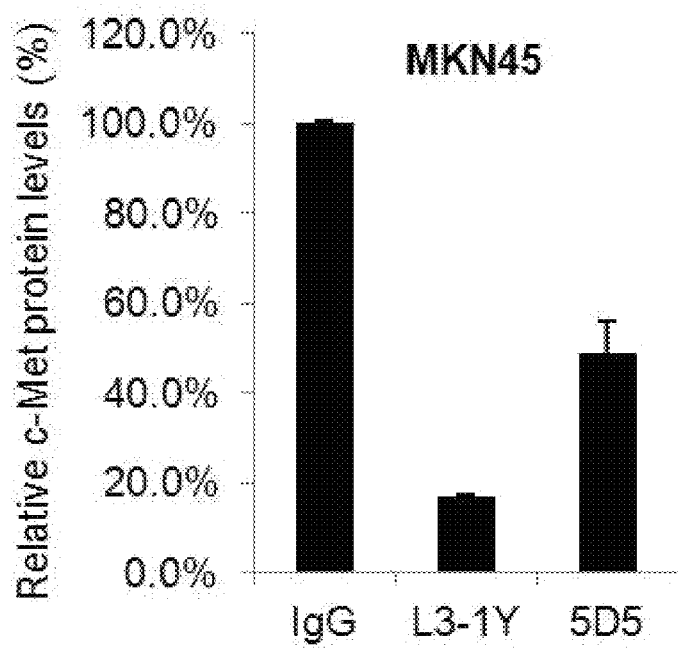

Total c-Met levels in MKN45 cells treated with the antibodies were measured using ELISA in the same manner as in Example 1.1, and the results are depicted in FIG. 1C. As is apparent from the data of FIG. 1C, the antibody L3-1Y significantly reduced the intracellular level of c-Met, compared to the positive control 5D5 as well as the negative control IgG. That is, the antibody L3-1Y has potent ability to trigger c-Met degradation.

1.4. Cell Viability—MKN45 Cell

After tumor cells (MKN45) were treated with the antibodies, their viability was measured using a cell proliferation assay. In this context, the cell proliferation assay was performed using CCK-8 (Dojindo Laboratories, Gaithersburg, Md., USA) according to the instructions of the manufacturer.

MKN45 cells were seeded at a density of 1×104 cells/ml/ well into 96-well plates and treated at 37° C. for 72 hours with or without various concentrations (0.0032, 0.016, 0.008, 0.4, 2, and 10 µg/ml) of IgG or L3-1Y. Subsequently, CCK-8 was aliquoted at a concentration of 10 µl/well to the plates, followed by incubation at 37° C. for an additional one hour. Absorbance at 450 nm of each well was measured on an automatic ELISA reader (Molecular Devices). Cell viability was expressed as percentages of the absorbance value of the non-treated group.

Figure 1D:
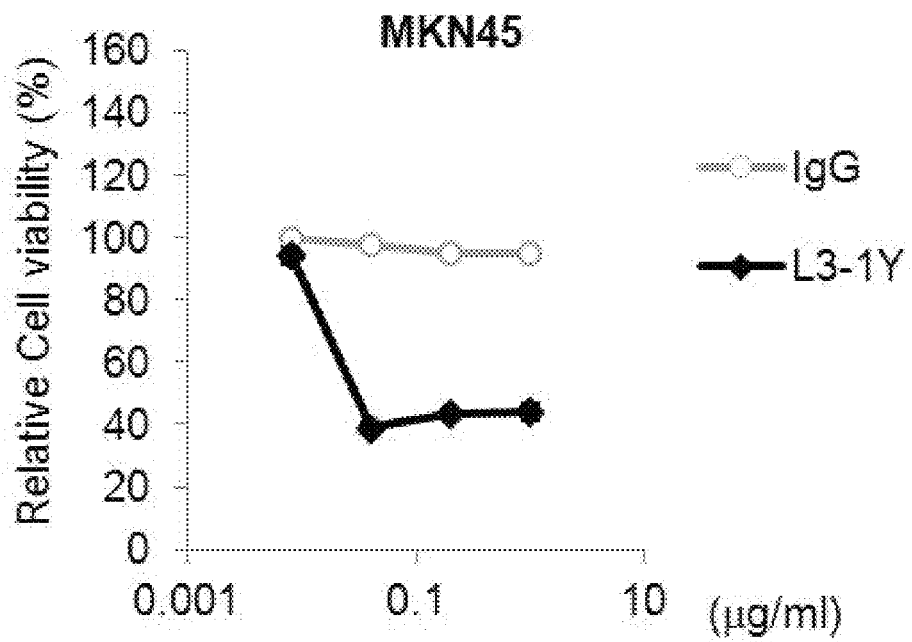

The results are shown in FIG. 1D. As seen in the graph of FIG. 1D, the viability of the tumor cells was significantly reduced upon treatment with the antibody L3-1Y (♦), compared to IgG (○).

EXAMPLE 2

Cbl-Dependent c-Met Degradation 1

2.1. Induction of Interaction Between Cbl and c-Met

NCI-H441 cells were seeded at a density of 2×105 cells/ ml/well into 100 mm plates, and then treated with 5 µg/ml of the anti-c-Met antibody L3-1Y or 5D5 at 37° C. for 30 min in a serum-free medium. The cells were lyzed using a protease mix tablet (Roche) in the lysis buffer Complete lysis-M (Roche, 04719956001) and incubated at 4° C. with immunoprecipitating antibody-conjugated A/G agarose beads (Pierce). These beads were washed four times with a lysis buffer. The proteins bound to the beads were eluted with a sampling buffer (Invitrogen), followed by immunoblot analysis.

Figure 2A:
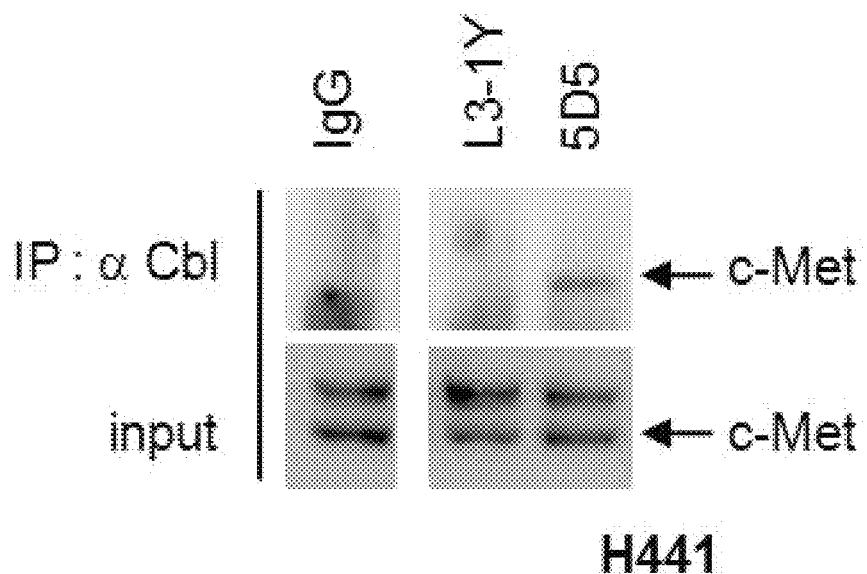

The results are given in FIG. 2A. As may be seen in the blots of FIG. 2A, the interaction between Cbl and c-Met was induced by the antibody 5D5, but not by the antibody L3-1Y. Cbl, although serving as a main E3 ligase to induce the quantitative reduction of c-Met, interacts with only activated c-Met and is thus highly apt to cause the adverse effect (agonism). Compared to the antibody 5D5, which induces the interaction of Cbl with c-Met, the antibody L3-1Y is deemed little causative of the adverse effect side effects because it does not induce the interaction.

2.2. c-Met Degradation in EBC-1 and NCI-H441 Cells

EBC-1 or NCI-H441 cells were seeded at a density of 2×105 cells/ml, together with 5 µg/ml of the anti-c-Met antibody L3-1Y or 5D5, into 96-well plates and incubated for 4 hours. Then, c-Met degradation was measured using ELISA in the same manner as in Example 1.1.

Figure 2B:
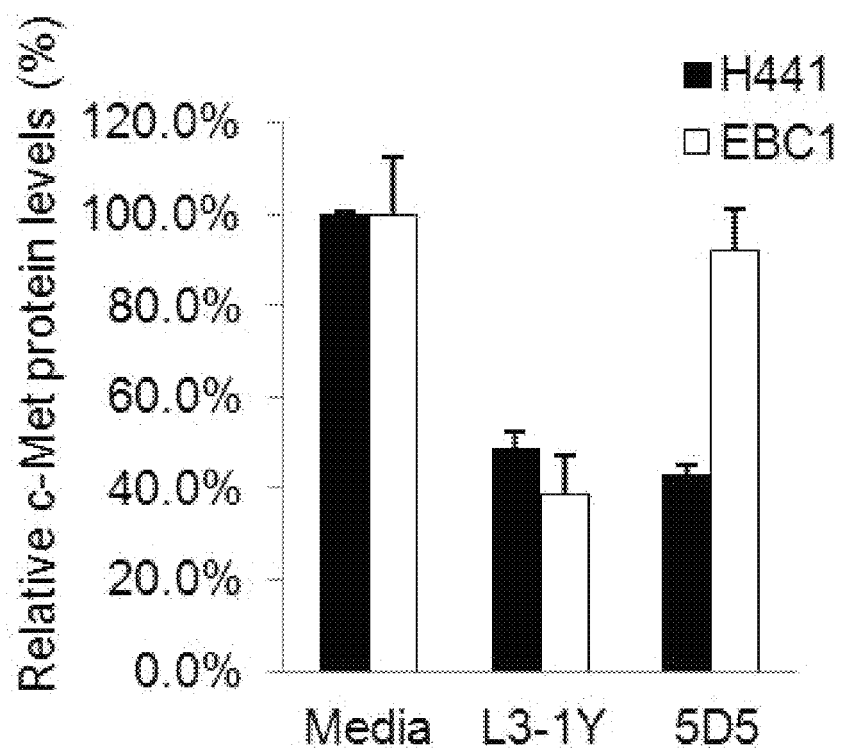

The results are given in FIG. 2B. As shown in FIG. 2B, the antibody L3-1Y decreased the total c-Met level by 50% or higher in both cells while the antibody 5D5 induced c-Met degradation in NCI-H441 cells to a degree similar to what is induced by L3-1Y, but almost did not in EBC-1 cells.

To examine the cause of the result, Cbl protein levels in EBC-1 and NCI-H441 cells were measured by Western blot analysis using an Cbl antibody (cell signaling). The result is given in the upper panel of FIG. 2C. In addition, as seen in FIG. 2C, Cbl protein was at a relatively high level in NCI-H441 cells, but did not exist in EBC-1 cells. Therefore, the reason why the antibody 5D5 cannot induce c-Met degradation in EBC-1 cells is the absence of Cbl protein in EBC-1 cells. Therefore, the antibody L3-1Y is concluded to trigger Cbl-independent c-Met degradation. In other words, the antibody L3-1Y may exert excellent therapeutic effects on tumors which are not sufficiently sensitive to preexisting anti-c-Met antibodies (e.g., 5D5), such as EBC-1-related tumors, exhibiting the significance that it expands the range of cancers that may be therapeutically treated with anti-c-Met antibodies.

In addition, lung cancer tissues from lung cancer patients (n=14, non-small cell lung cancer (NSCLC) from Oncotest) were analyze for Cbl protein level by Western blot using the Cbl antibody (cell signaling) in the same manner as above. The results are given in the lower panel of FIG. 2C. As may be seen in FIG. 2C, Cbl levels differ from one patient to another, which indicates that patients, although suffering from the same cancer, are less apt to be therapeutically treated with preexisting anti-c-Met antibodies (e.g., 5D5) if their Cbl protein levels are low. Therefore, if their Cbl protein levels are known or measured, patients may be treated with pertinent antibodies in consideration of personal biological properties, so that more effective personalized therapy may be achieved.

2.3. Effect of c-Met Inhibitor on c-Met Degradation: MKN45 Cell

MKN45 cells were seeded at a density of 2×105 cells/ml, together with predetermined concentrations of the anti-c-Met antibody L3-1Y or 5D5, into 96-well plates and incubated for four hours. To each well, 1 µl of PHA-665752 (Selleck Chemical) was added. For controls, 1 µl of DMSO was used, instead of the inhibitor. c-Met degradation was analyzed using ELISA in the same manner as in Example 1.1. The results are given in FIG. 2E, and show that L3-1Y may trigger c-Met degradation irrespective of whether a c-Met is activated or not.

2.4. Cell Viability—EBC-1 Cell

EBC-1 was seeded at a density of cells/ml/well into 96-well plates and incubated for 72 hours with various concentrations of the antibody 5D5 or L3-1Y (0.0032, 0.016, 0.008, 0.4, 2, and 10 μg/ml). Cell viability was measured in the same manner as in Example 1.4.

Figure 2E:
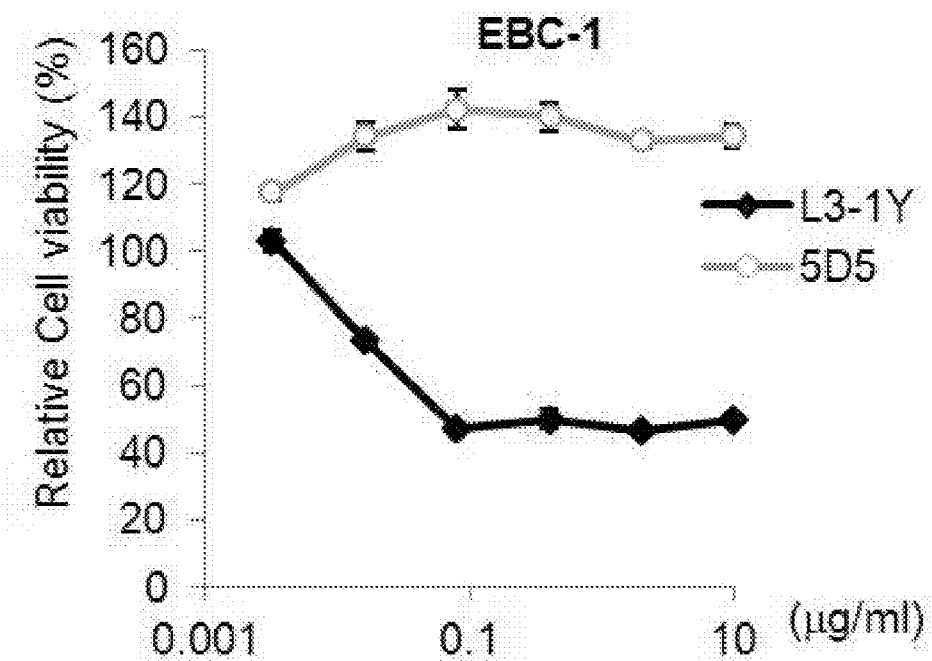

The results are given in FIG. 2E. As shown in FIG. 2E, the cell viability was significantly decreased with the antibody L3-1Y (♦), compared to the antibody 5D5 (○).

EXAMPLE 3

Cbl-Dependent c-Met Degradation 2 (Degradation Pathway)

3.1. c-Met Degradation Mechanism of Anti-c-Met Antibody 1: Ubiquitination Assay

An experiment was made to see whether Anti-c-Met antibody-triggered c-Met degradation takes place through the lysosomal pathway or the proteasome pathway mediated by E3 ligase including Cbl. In this context, poly-ubiquitination was examined by an ubiquitination assay.

Twenty-four hours after EBC-1 or NCI-H441 cells were seeded at a density of 2×105 cell/ml into 100 mm plates, they were incubated with 5 μg/ml of the antibody L3-1Y or 5D5 at 37° C. for 30, 60, or 120 min. The cells were separated and treated with a lysis buffer Complete lysis-M (Roche, 04719956001) to afford a protein extract. Ahead of the cell separation, MG132 ($C_{26}H_{41}N_3O_5$, Merck) or concanamycin (Merck) was added to inhibit the proteasome pathway or the lysosome pathway, respectively, so as to increase protein levels. Together with anti-c-Met antibody-conjugated A/G agarose beads (Pierce), 500 μg of the protein extract was pulled down. The endogenous ubiquitination of c-Met was examined by immunoblotting using an anti-Ub antibody (Santa Cruz).

Figure 3A:
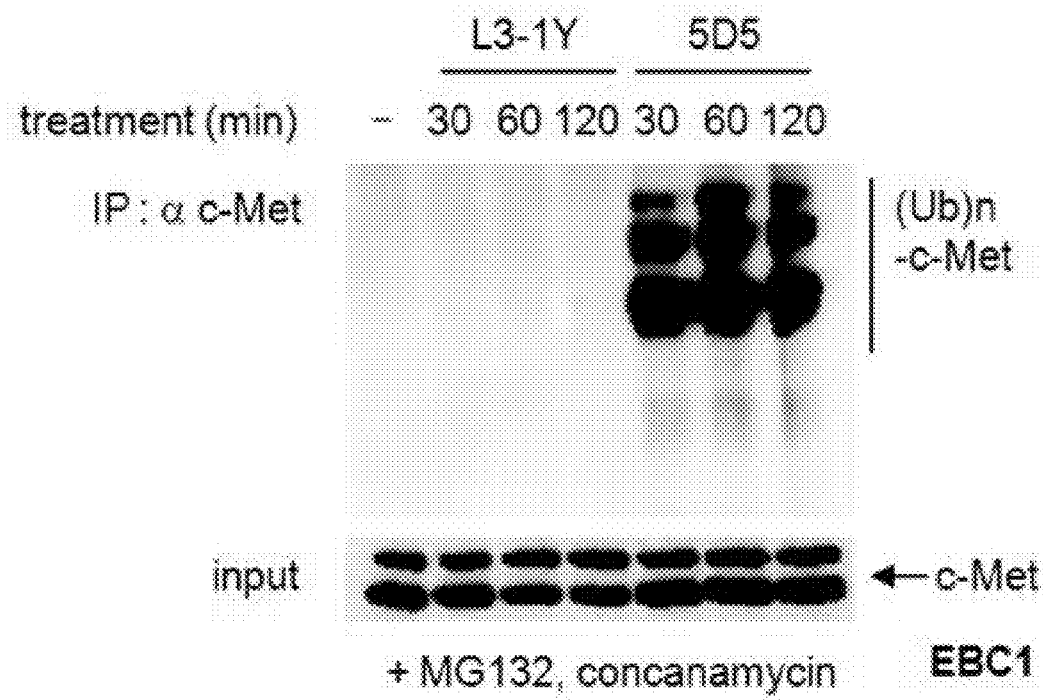
Figure 3B:
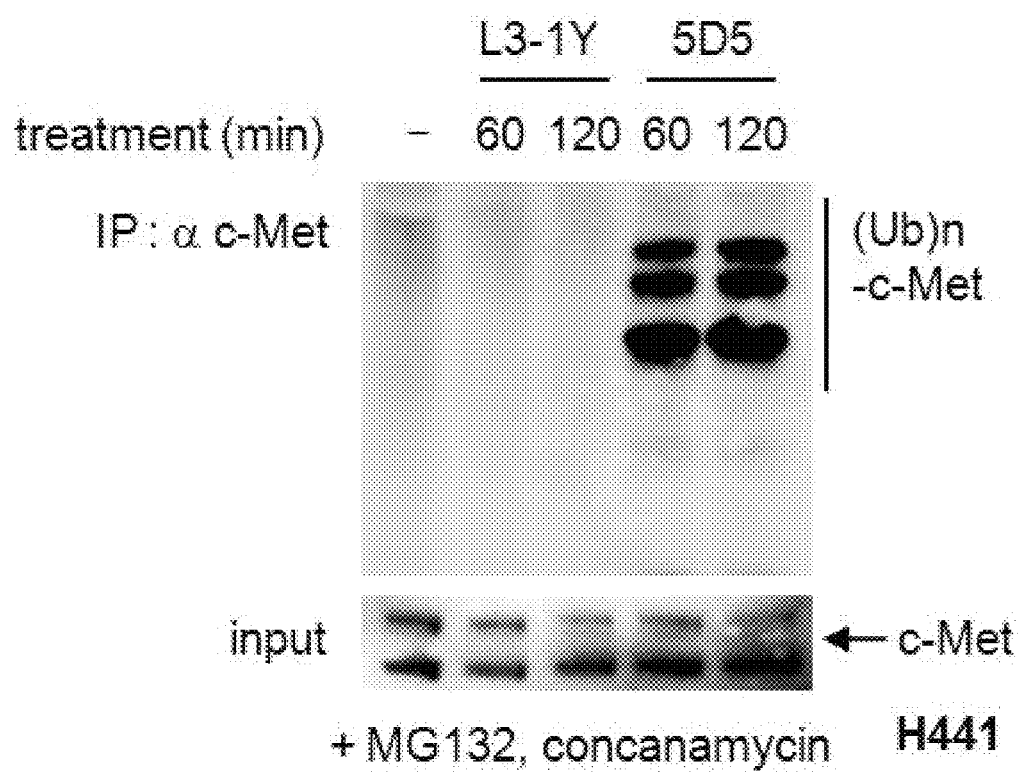

Photographs of immunoblots are given in FIGS. 3A and 3B (3A: immunoblots of EBC-1 cells, 3B: immunoblots of NCI-H441 cells). As may be seen in FIGS. 3A and 3B, the poly-ubiquitination of c-Met was observed in both the cell lines after treatment with the antibody 5D5, but neither of the cell lines after treatment with the antibody L3-1Y. Thus, the antibody 5D5 may induce the poly-ubiquitination of c-Met. but the antibody L3-1Y cannot, which indicates that the antibody L3-1Y is involved in c-Met degradation through a non-proteasome pathway, that is, a lysosome pathway.

3.2. c-Met Degradation in Cells Transformed with Cbl siRNAs: Cbl Knockdown

Dependency of the anti-c-Met antibody-triggered c-Met degradation on Cbl was examined. For this, Cbl knockdown was achieved by transforming Cbl siRNAs into EBC-1 cells which were then treated with antibodies before measuring c-Met degradation.

Cbl siRNAs (Dharmacon)-transformed EBC-1 cells which were seeded at a density of 2×105 cells/ml into plates were incubated at 37° C. for 24 hours with 5 μg/ml of the anti-c-Met antibody L3-1Y. c-Met degradation was measured using ELISA in the same manner as in Example 1.1. For control, 5 μg/ml of IgG was used.

Figure 3C:
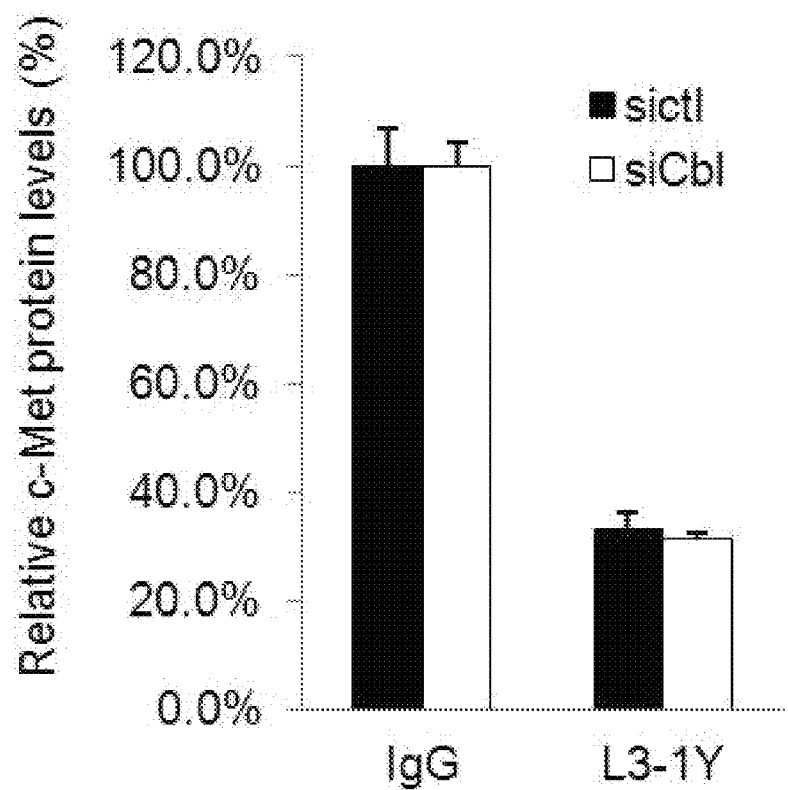

The results are given in FIG. 3C. sictl represents a control treated with a control siRNA commercially available from Dharmacon, in comparison with siCbl. As may be seen in FIG. 3C, the total c-Met level in the Cbl siRNA-transformed EBC-1 cells treated with the antibody L3-1Y was reduced to about 30% of that in the transformed EBC-1 cells treated with the control IgG, indicating a c-Met degradation efficiency of as high as about 70%.

3.3. c-Met Mechanism of Anti-c-Met Antibody 2—Treatment with MG132

Apart from Example 3.1, the c-Met degradation mechanism of anti-c-Met antibody was examined. In this regard, c-Met degradation was measured when the proteasome pathway was blocked by the proteasome inhibitor MG132 ($C_{26}H_{41}N_3O_5$, Merck).

EBC-1 cells which were seeded at a density of 2×105 cells/ml into 96-well plates were incubated at 37° C. for 4 hours with the anti-c-Met antibody L3-1Y 5 μg/ml+DMSO 1 μL, or with the antibody L3-1Y 5 μg/ml+MG132 1 μL (10 μm). c-Met degradation was measured using ELISA in the same manner as in Example 1.1. For control, IgG 5 μg/ml+DMSO 1 μL, or IgG 5 μg/ml+MG132 1 μL was used.

Figure 3D:
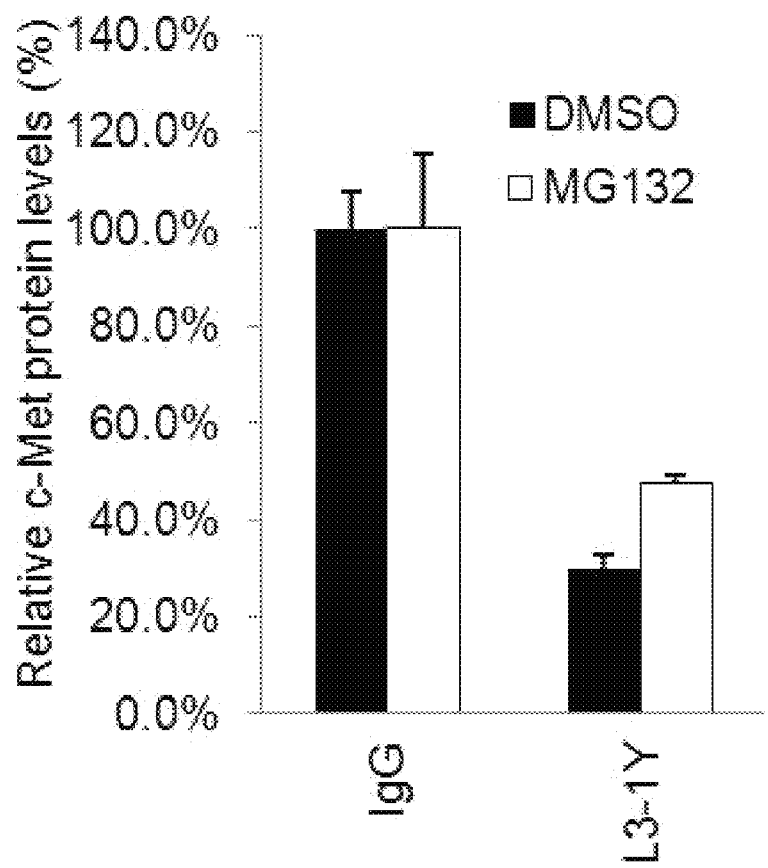

The results are given in FIG. 3D. As may be seen in FIG. 3D, the antibody L3-1Y reduced the c-Met level by about 70% in the cells treated without the proteasome inhibitor MG132 and by about 50% in the cells treated with MG132, indicating that L3-1Y-triggered-c-Met degradation is not significantly affected by MG132 treatment. The data demonstrates again that c-Met degradation of the antibody L3-1Y does not take the Cbl-mediated proteasome pathway, but is independent of Cbl.

3.4. Cell Viability—HS746T Cell

HS746T cells were seeded at a density of 5×104 cells/ml/well into 96-well plates and incubated with various concentrations (0.0032, 0.016, 0.008, 0.4, 2, and 10 μg/ml) of the antibody 5D5 or L3-1Y at 37° C. for 72 hours. Cells were measured on the basis of the method used in the example.

HS746T is a stomach cancer cell line in which the site of c-Met for interaction with Cbl is truncated by natural mutation in all c-Met molecules.

Figure 3E:
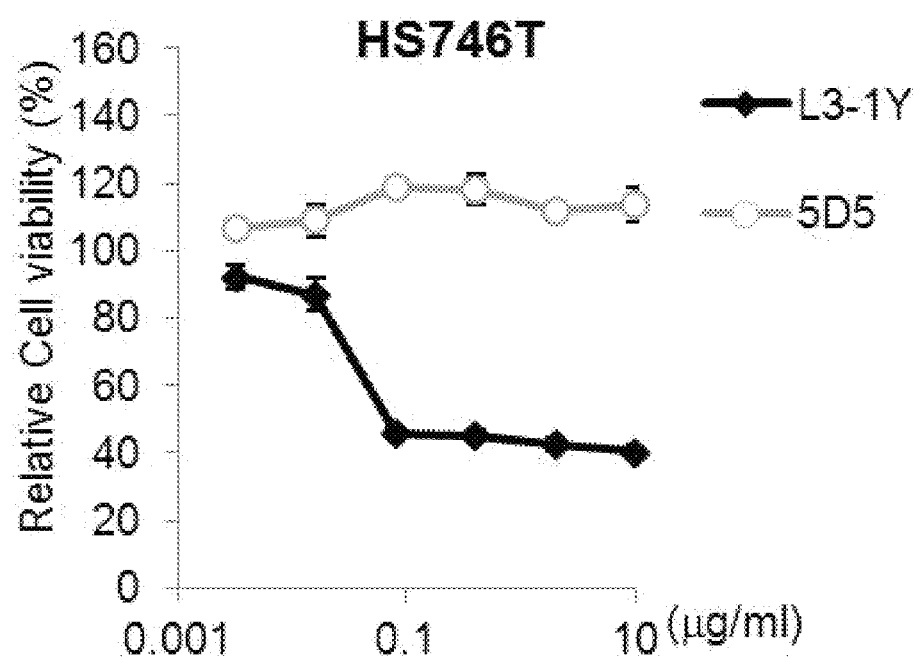

The results are given in FIG. 3E. As may be seen in FIG. 3E, tumor cell viability was greatly reduced upon treatment with the antibody L3-1Y (♦), compared to the antibody 5D5 (○).

3.5. Apoptosis Induction

Anti-c-Met antibodies were assayed for ability to induce apoptosis.

Apoptotic effects of IgG (control), L3-1Y, and 5D5 on cells were measured in vitro using a Caspase 3/7 Glo® assay system on HS746T cells present at a density of 5×104 cells/ml/well in 96-well plates.

In brief, EBC-1 cells in an FBS 10% (v/v) RPMI 1640 medium and HS746T cells in an FBS 10% (v/v) DMSO medium were plated at a density of 5×10³ cells/well into respective black 96-well plates (Corning Incorporated), and incubated at 37° C. for 72 hours with various dilutions (0.0032, 0.016, 0.008, 0.4, and 2 μg/ml) of IgG, L3-1Y or 5D5 in a medium supplemented with 10% (v/v) FBS and then at room temperature for 30 min with 100 μL/wells of Caspase 3/7 Glo® (Promega). Luminescence signals were recorded with an Envision 2104 Multi-label Reader (Perkin Elmer). Apoptosis rates after being normalized to CCK-8 assay values are shown in FIG. 3F.

Figure 3F:
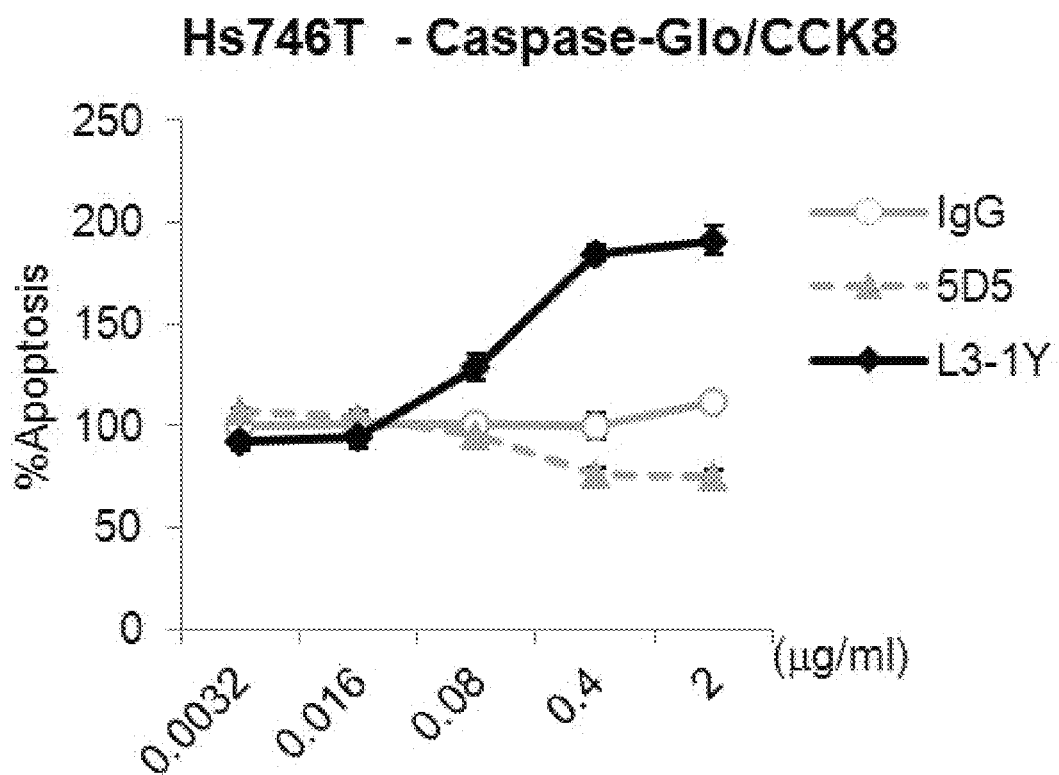

As may be seen in FIG. 3F, the antibody L3-1Y (♦) was found to induce potent apoptosis, whereas the apoptosis induced by 5D5 (▲) was weaker than the control IgG (○).

The apoptotic effects of the antibodies L3-1Y and 5D5 on the lung cancer cell line EBC-1 were measured in the same manner and the results are given in FIG. 3G. As may be seen in FIG. 3G, the antibody L3-1Y induced higher apoptosis in a dose-dependent manner even in the lung cancer cell line EBC-1, which expresses a low level of Cbl, compared to the preexisting anti-c-Met antibody 5D5.

EXAMPLE 4

LRIG1-Mediated c-Met Degradation 4.1. Induction of Interaction Between LRIG1 and c-Met by Anti-c-Met Antibody: EBC-1 Cell An examination was made of the ability of anti-c-Met antibodies to induce c-Met to associate with LRIG1 in EBC-1 cells. An LRIG1-c-Met associated protein was separated and purified by co-immunoprecipitation and quantitatively analyzed by immunoblotting. In this regard, cells were treated with an anti-c-Met antibody for periods of time shown in FIG. 4A and harvested. The cells were lysed in a lysis buffer Complete lysis-M (Roche, 04719956001) to afford a protein extract. Together with anti-c-Met antibody-conjugated A/G agarose beads (Pierce), 500 μg of the extract was pulled down, followed by immunoblotting with an anti-LRIG1 antibody (Abcam) to detect the association of c-Met with LRIG1. The data obtained above shows that the association of c-Met with LRIG1 is induced two hours after treatment with L3-1Y.

4.2. Induction of Interaction Between LRIG1 and c-Met by Anti-c-Met Antibody: HEK293 Cell An examination was made of the ability of anti-c-Met antibodies to induce c-Met to associate with LRIG1 in HEK293 cells. An LRIG1-c-Met associated protein was separated and purified by co-immunoprecipitation and quantitatively analyzed by immunoblotting. In this regard, cells were treated with an anti-c-Met antibody for 2 hours and harvested. The cells were lysed in a lysis buffer Complete lysis-M (Roche, 04719956001) to afford a protein extract. Together with anti-c-Met antibody-conjugated A/G agarose beads (Pierce), 500 μg of the extract was pulled down, followed by immunoblotting with an anti-LRIG1 antibody (Abcam) to detect the association of c-Met with LRIG1.

Figure 4B:
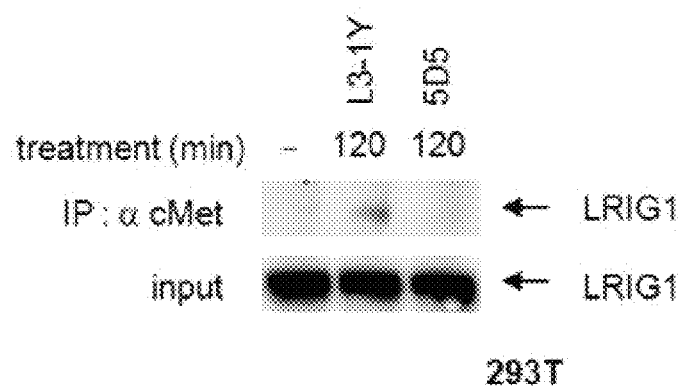

The immunoblotting results are shown in FIG. 4B. As is apparent from the data of FIG. 4B, the antibody L3-1Y may induce the association of LRIG1 with c-Met whereas the antibody 5D5 cannot.

4.3. Apoptosis Induction by Anti-c-Met Antibody 1

Figure 4C:
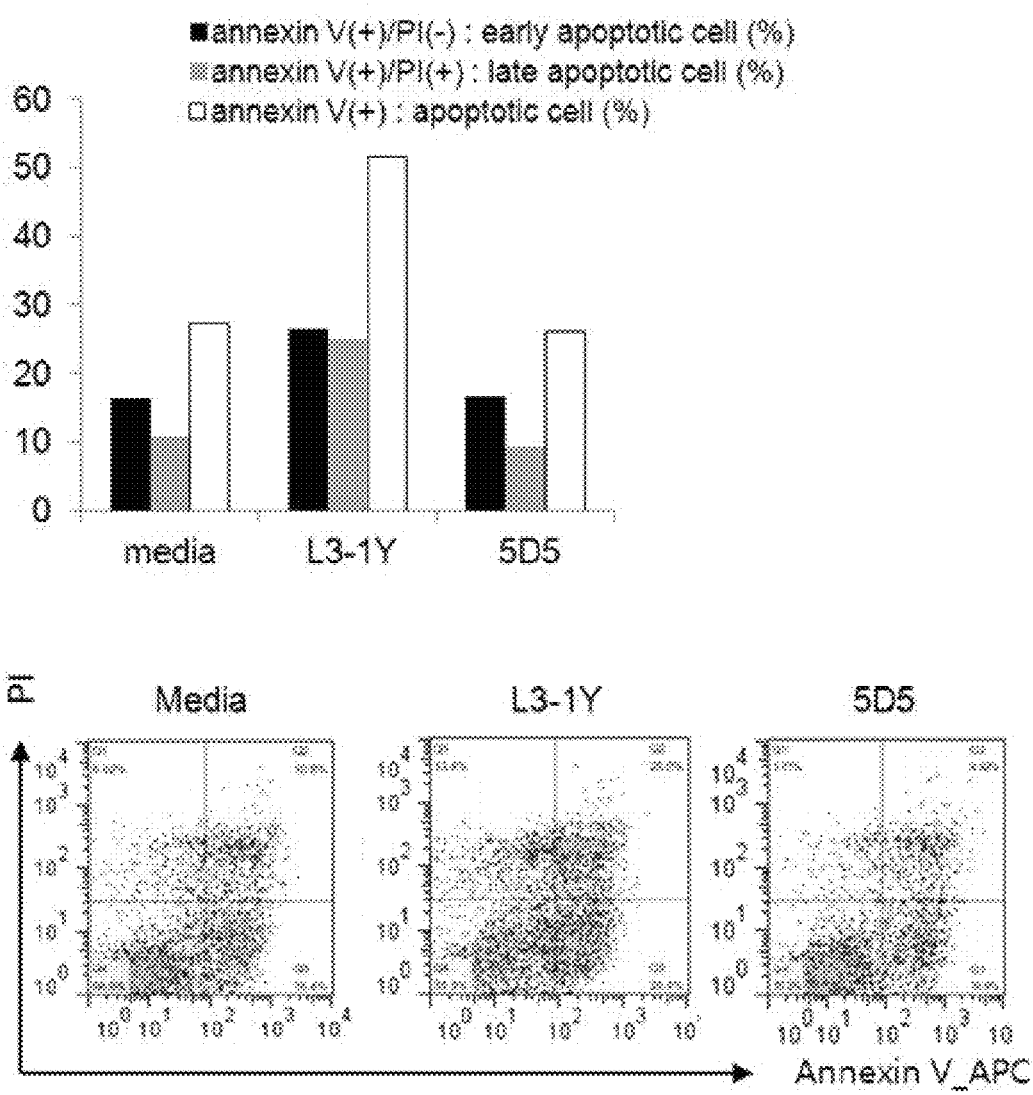

EBC-1 cells were treated for 72 hours with 1 μg/ml of L3-1Y or 5D5 and transferred to tubes which were spun at 120 rpm at 4° C. for 3 min. The cells were stained for 15 min with 5 μl of AnnexinV (BD Pharmingen) and 2 μl of PI (Propidium Iodide, 50 g/μl) under a dark condition, followed by FACS analysis (FACS CAntoll flow cytometer, Becton, Dickinson and Company). The results are shown in FIG. 4C. The annexin V(+)/PI(−) cell group represents the progress of early apoptosis while the Annexin V(+)/PI(+) cell group underwent later apoptosis. L3-1Y was found to increase both early and late cell apoptosis, compared to 5D5.

4.4. Apoptosis Induction by Anti-c-Met Antibody 2

After L3-1Y or 5D5EBC-1 was applied at various concentrations (0.0032, 0.016, 0.008, 0.4, 2, and 10 μg/ml) to cells which were seeded at a density of 5×104 cells/ml/well into 96-well plates, apoptosis rates were measured in vitro using a Caspase 3/7 Glo® assay system in the same manner as in Example 3.5.

Figure 4D:
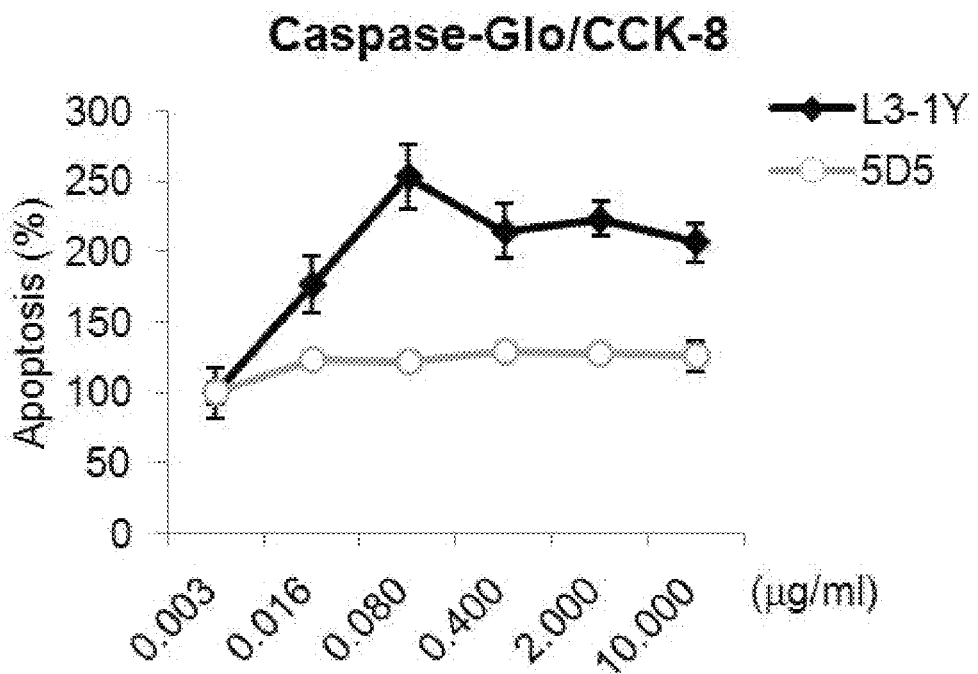

The results are shown in FIG. 4D. As may be seen in FIG. 4D, far higher apoptotic effects on EBC-1 cells were obtained with the antibody L3-1Y (♦) than 5D5 (○).

4.5. Apoptosis Induction by Anti-c-Met Antibody 3

To examine the relation of LRIG1 to the apoptotic effect, shown in Example 4.4, of the antibody L3-1Y on EBC-1, EBC-1 cells which were subjected to reverse-transfection with LRIG1 siRNAs (Dharmacon) for 24 hours were induced to undergo apoptosis in the same manner as in Example 4.4.

Figure 4E:
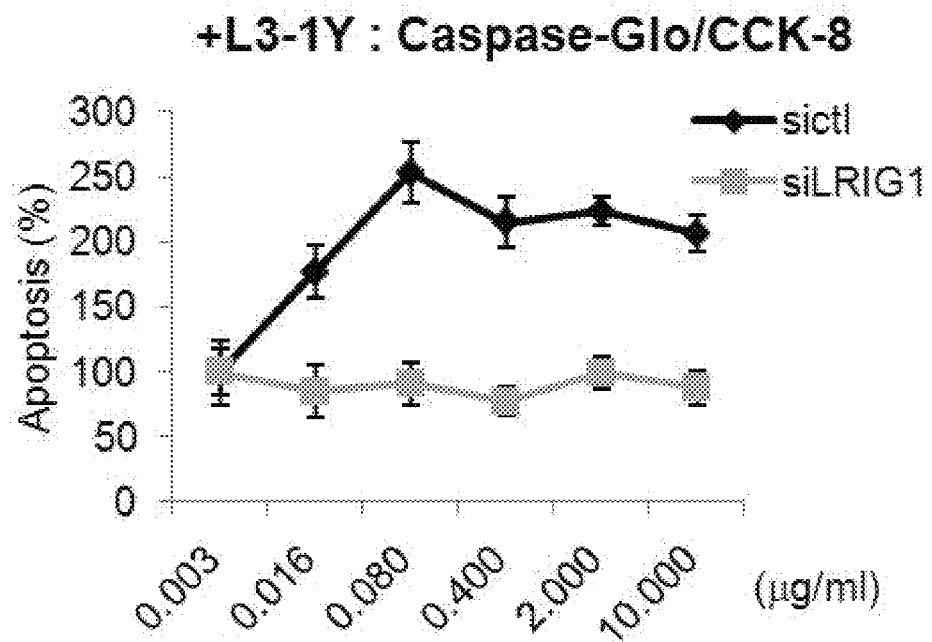

Apoptosis rates are depicted in FIG. 4E. In the graph, sictl represents a control treated with a control siRNA commercially available from Dharmacon. As may be seen in FIG. 4E, the apoptotic effect of L3-1Y (♦) was significantly reduced in LGIG1-knockdown EBC-1 cells compared to the control, indicating that the ability of L3-1Y to induce the apoptosis of EBC-1 cells is attributed to the formation of the LRIG1-c-Met associated protein.

4.6. c-Met Degradation Mechanism of Anti-c-Met Antibody

In order to examine the c-Met degradation mechanism of anti-c-Met antibodies, c-Met degradation was measured in EBC-1 cells whose lysosome pathway was blocked by treatment with the lysosomal pathway inhibitor concanamycin (Merck).

EBC-1 cells which were seeded at a density of 2×105 cells/ml into 96-well plates were incubated at 37° C. for 4 hours with the anti-c-Met antibody L3-1Y 5 μg/ml+DMSO 1 μL, the antibody L3-1Y 5 μg/ml+concanamycin 1 μL, the antibody 5D5 5 μg/ml+DMSO 1 μL, or the antibody 5D5 5 μg/ml+concanamycin 1 μL, and c-Met degradation was measured using ELISA in the same manner as in Example 1.1. For control, IgG 5 μg/ml+DMSO 1 μL, or IgG 5 μg/ml+MG132 1 μL, was used.

Figure 4F:
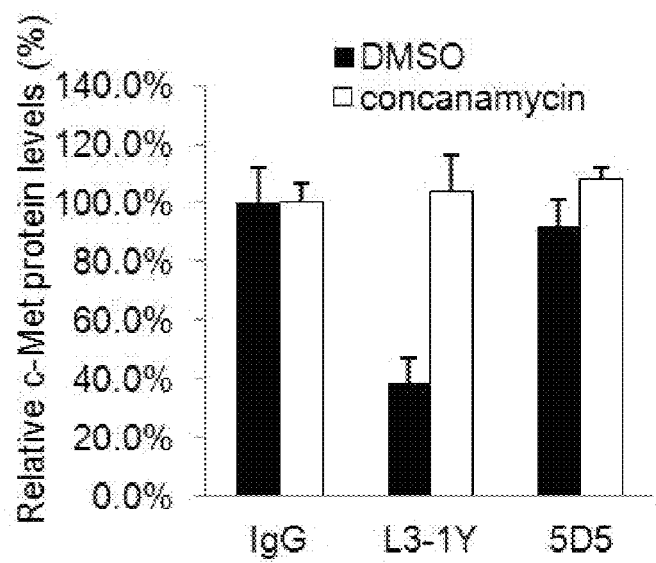

The results are given in FIG. 4F. As may be seen in FIG. 4F, c-Met degradation in the 5D5-treated cells was almost equivalent to that in the control cells, and was somewhat increased upon the use of DMSO compared to concanamycin, but without significance because of a difference of only 10% or less. In contrast, the antibody L3-1Y did not trigger c-Met degradation in the presence of concanamycin, but increased c-Met degradation by 60% or greater upon DMSO treatment, demonstrating that the c-Met degradation of the antibody L3-1Y takes the lysosomal pathway.

4.7. Immunocytochemistry

Figure 4G:
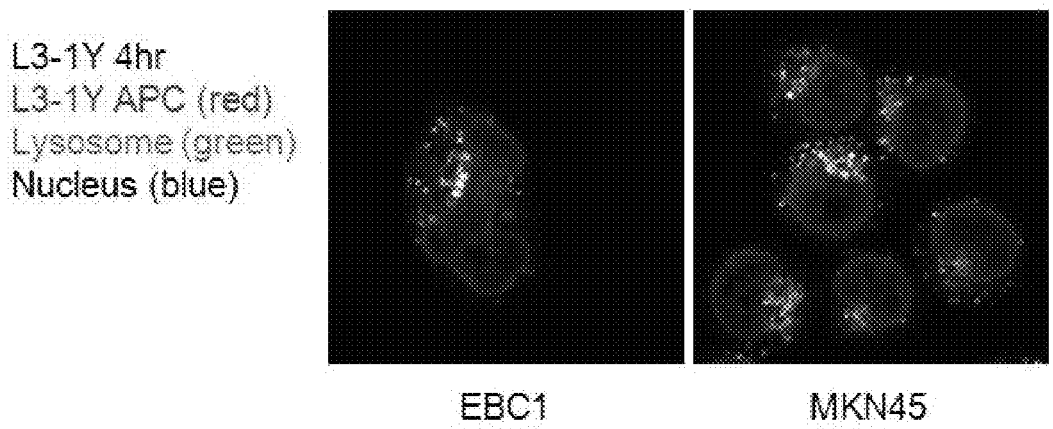

Antibody-mediated co-localization of c-Met and lysosome was analyzed by immunocytochemistry. MKN45 or EBC-1 cells at a density of 2×105 cells/ml were incubated for 4 hours with 1 μg/ml of the anti-c-Met antibody L3-1Y. The cells were fixed with 2% (w/v) paraformaldehyde and blocked for 30 min with 5% (v/v) goat serum (Jackson ImmunoResearch) in PBS-T (0.1% (v/v) Triton X-100 in PBS) before incubation with Alexa 488-conjugated anti-mouse IgG (Invitrogen) at room temperature for 1 hour. Then the cells were washed many times with PBC (Gibco), counterstained with DAPI (4',6'-diamidine-2'-phenylindole dihydrochloride; Vector Labs) and placed in a fluorescent mounting medium. Immunofluorescence images were obtained with a fluorescence microscope (Carl Zeiss) and are given in FIG. 4G. L3-1Y-APC is an antibody labeled with a detectable tag. As seen in FIG. 4G, the antibody L3-1Y was observed in lysosomes, demonstrating that lysosomes are involved in L3-1Y-triggered c-Met degradation.

EXAMPLE 5

Therapeutic Effect of Anti-c-Met Antibody on Tumor (In Vivo)

5.1. Anti-Tumor Effect in Tumor-Xenografted Model

For use in examining in vivo effects of anti-c-Met antibody on tumor growth, male BALB/c nude mice, 5~6 weeks old, were xenografted with a tumor (all experiments were carried out in Pharmalegacy, China). For at least one week before the transplantation, the mice were acclimated.

Then, the mice were anesthetized with 1-2% isofuran and xenografted subcutaneously in the right flank with 5×106 cells of EBC-1 or HS746T. Seven days after the grafting, the tumors measured 50 mm3 or greater on average. The mice were divided into the following three groups: 5D5 (5 mg/kg I.V. once/week) treated, L3-1Y (5 mg/kg I.V. once/week) treated, and vehicle (PBS 0.2 ml I.V. once/week) treated (control). Each group was composed of 15 mice.

Over a total of five weeks, volumes and weights of the tumors were measured 203 times a week. Tumor volume (V) was calculated according to the following formula:

$$V(mm3)=\{\text{Long Axis Length(mm)}\times(\text{Small Axis Length(mm)})2\}/2.$$

Figure 5A:
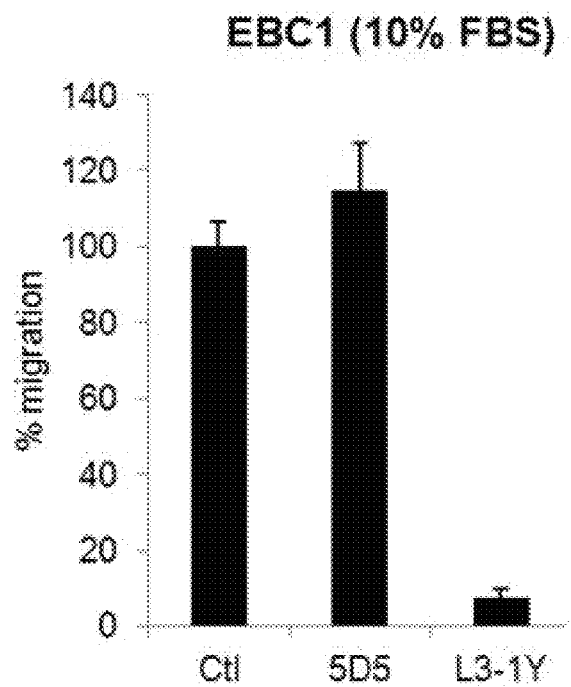
Figure 5B:
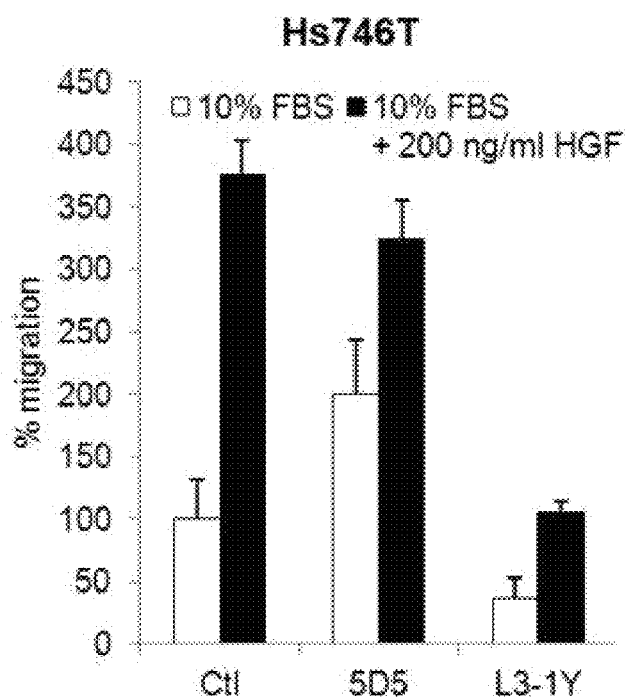
Figure 5C:
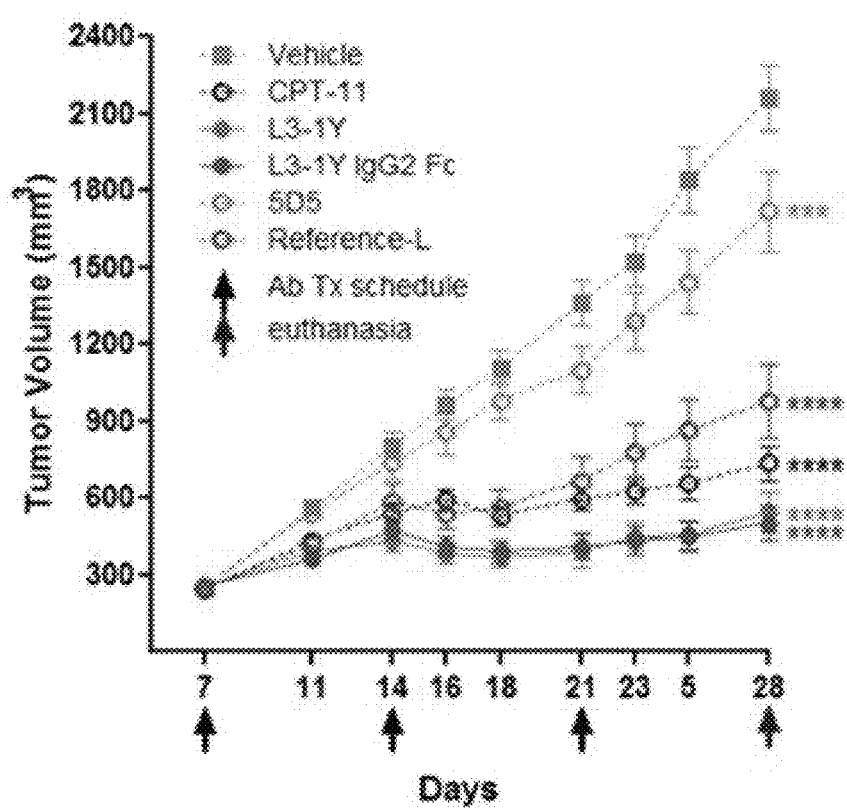
Figure 5D:
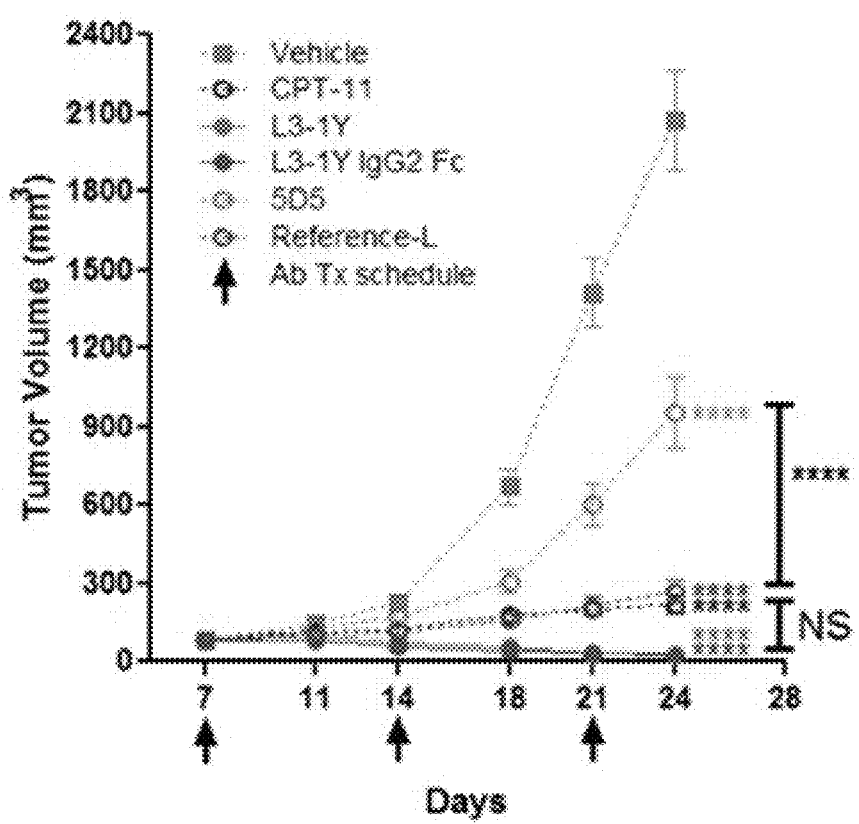

The results are given in FIG. 5C and Table 3 for EBC-1 and in FIG. 5D and Table 4 for HS746T.

TABLE 3

| EBC1 | At d28:TV |
|---|---|
| Vehicle | 0.0 |
| L3-1Y (1) | 84.6 |
| L3-1Y (2) | 87.0 |
| 5D5 | 23.3 |

TABLE 4

| HS746T | At d28:TV |
|---|---|
| Vehicle | 0.0 |
| L3-1Y (1) | Regression |
| L3-1Y (2) | Regression |
| 5D5 | 56.4 |

L3-1Y (1) is an antibody based on hIgG1 with the Th7 hinge (usually referred to just as L3-1Y) while L3-1Y (2) contains the same epitope but has the hIgG2 backbone. FIGS. 5C and 5D are graphs showing tumor growth in mice xenografted with EBC-1 cells (5c) and HS746T cells (5d) over time (n=15) (for comparison, the c-Met small molecule inhibitor CPT-11 and a reference antibody (Reference L) were used). Tumor suppression of each of the antibodies was expressed as percentages of volume reduction compared to the tumor volume on the 28th day of the vehicle-treated group (0%) in Table 3 for EBC-1 and Table 4 for HS746T.

As may be seen in FIGS. 5C and 5D and Tables 3 and 4, the antibody L3-1Y was found to have great anti-tumor activity in vivo, compared to the other antibodies.

5.2. Cell Migration Assay

Cell migration was observed in CIM-Plates of the xCEL-Ligence DP system (Roche). A suspension of 5×104 cells in 100 μl of a serum-free medium was placed in the upper chamber. The lower part of CIM-plate 16 was filled with a 10% serum medium (migration to chemo-attractant). In the case that HGF was used, it was added at a concentration of 200 ng/ml to the 10% serum medium. Cell migration capability was evaluated by measuring impedance signals only from the cells that passed through an 8 μm pore membrane. The migration of EBC1 (FIG. 5A) was increased by about 10% upon treatment with 5D5, but decreased by 90% or higher upon treatment with L3-1Y. Only L3-1Y reduced the migration of HS746T, as well, whether treated with HGF or not (FIG. 5B).

EXAMPLE 6

Anti-Tumor Effect of Anti-c-Met Antibody on Tumor Resistant to EGFR-Targeted Therapy 6.1. Preparation of EGFR-Targeted Therapy-Resistant Tumor The human lung cancer cell line HCC827 was treated in vitro for a predetermined period of time with Erlotinib, an EGFR antagonist, to establish HCC827 ER (HCC827 Erlotinib-resistant) cell lines. In detail, HCC827 (ATCC) which was seeded at a density of 2×105 cells/ml was treated in vitro with a gradual gradient concentration of the EGFR antagonist Erlotinib (Selleck Chemical) from 5 nm to 10 μm over 5 months to establish Erlotinib-resistant (ER) cell lines HCC827 ER10 and HCC827 ER15.

Figure 6A:
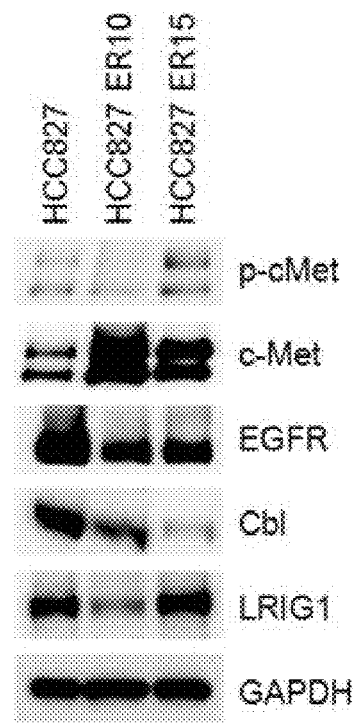
Figure 6B:
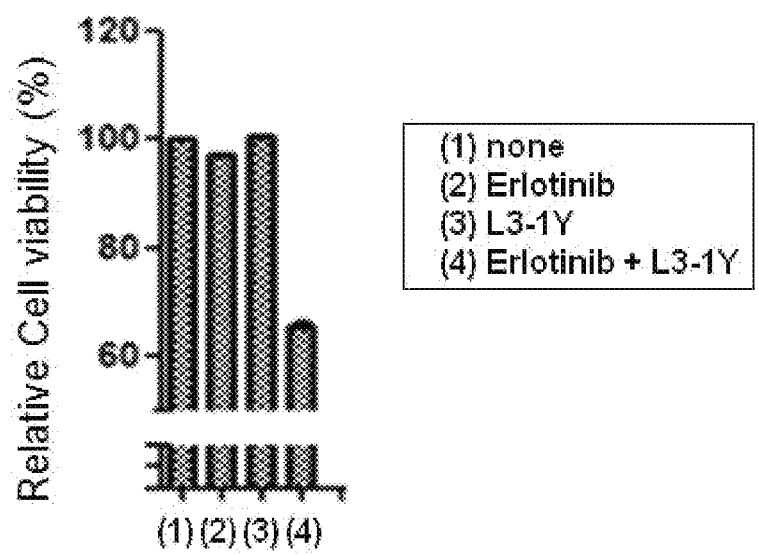
Figure 6C:
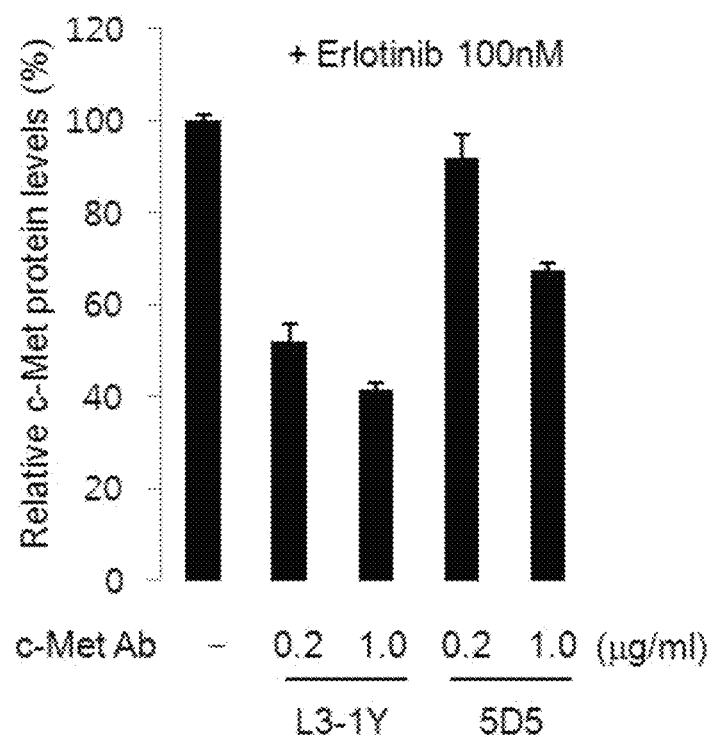
Figure 6D:
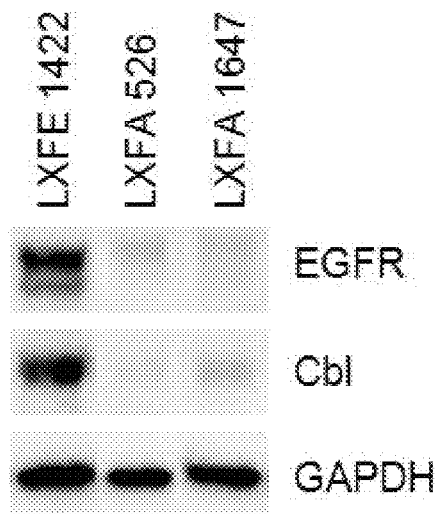
Figure 6E:
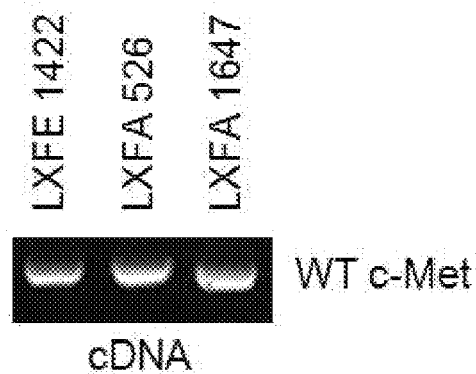
Figures 6F, 7:
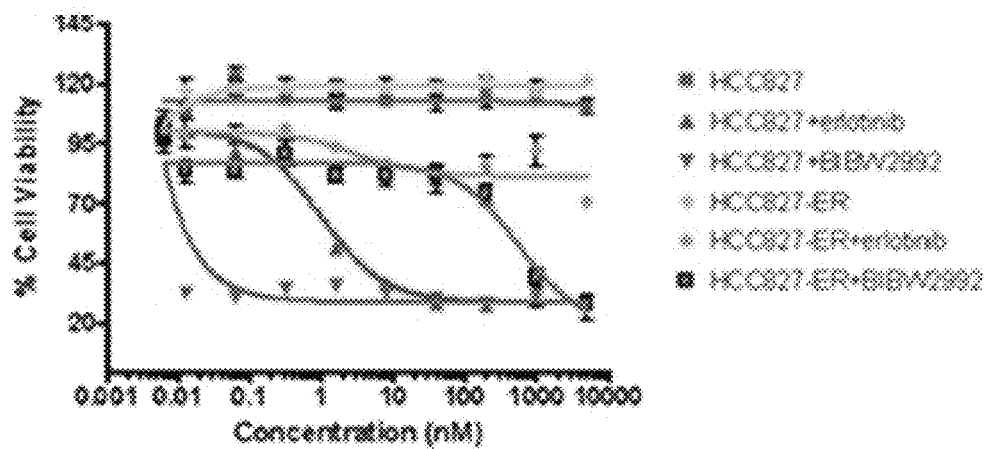
Figure 8:
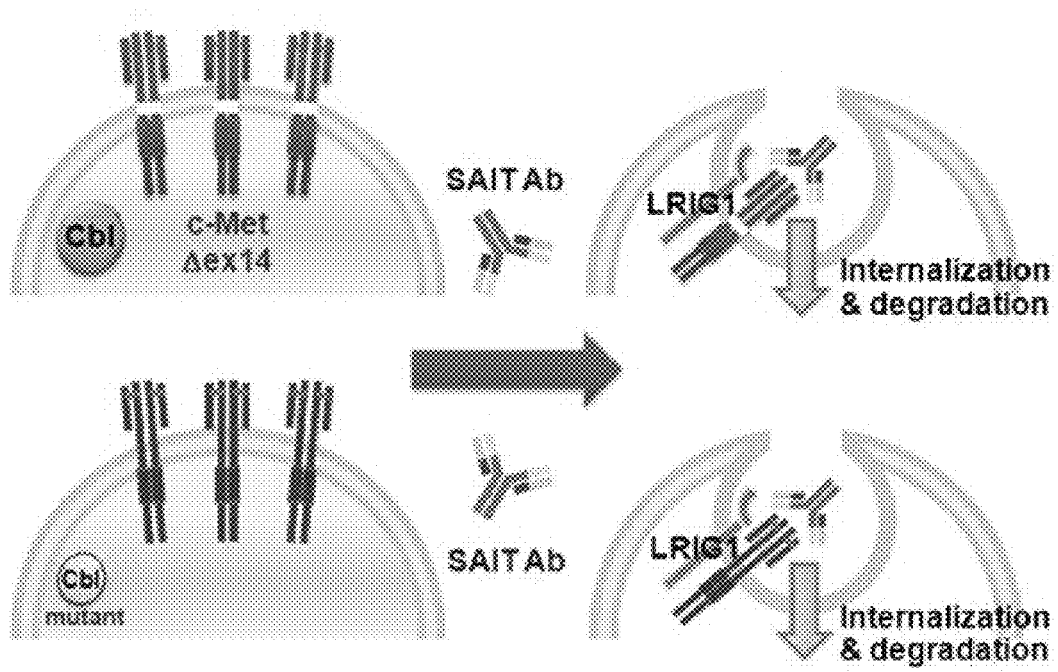
FIG. 8 is a schematic diagram showing the hypothesis of L3-1Y-triggered, Cbl-independent c-Met-degradation.

Erlotinib resistance was confirmed by a cell viability assay, and the results are shown in FIG. 7. The parent cell line HCC827 died with the treatment of Erlotinib or BIBW2992 (Selleck Chemical), whereas the viability of HCC287-ER (Erlotinib resistant) was not reduced at all by Erlotinib. Apart from a high dose of BIBW2992, the ER cells were not induced to undergo cell death by the EGFR antagonist BIBW2992. As may be seen in FIG. 7, the ER cell lines became resistant to the EGFR antagonist BIBW2992 as well as Erlotinib, indicating that there was a likelihood of resistance to other EGFR antagonists.

HCC827, HCC827 ER10, and HCC827 ER15 cells were analyzed for the expression of p-c-Met, c-Met, EGFR, Cbl, LRIG1, and GAPDH therein by immunoblotting using respective antibodies. In this context, antibodies to p-c-Met, c-Met, Cbl, EGFR, and GAPDH (14C10) were purchased from Cell Signaling and an antibody to LRIG1 was purchased from Abcam.

The immunoblots thus obtained are shown in FIG. 6A. As may be seen in FIG. 6A, the level of c-Met gene was about three-fold increased in both the ER cells, compared to non-resistant HCC82, indicating that constant exposure to an EGFR inhibitor increases c-Met levels and thus elicits resistance.

6.2. Apoptotic Effect of a Combination Dosage of Anti-c-Met Antibody and EGFR Antagonist on Tumor Cell HCC827 ER15, which expresses c-Met at a high level but Cbl at a relatively low level was used in assay for the apoptotic effect of a combination dosage of an anti-c-Met antibody and an EGFR antagonist.

HCC827 ER15 cells were seeded at a density of 5×104 cells/ml/well into 96-well plates and incubated with L3-1Y 0.14 μg/ml, Erlotinib 10 nm, or L3-1Y 0.14 μg/ml+Erlotinib 10 nm at 37° C. for 72 hours. Then, cell viability was measured in the same manner as in Example 1.4.

The results are expressed as percentages of the cell viability (100%) of the control which was neither treated with an anti-c-Met antibody nor an EGFR antagonist in FIG. 6B. As may be seen in FIG. 6B, almost no apoptotic effects were found in the EGFR resistant cells to which the anti-c-Met antibody L3-1Y or the EGFR antagonist Erlotinib were separately administered, but the cell viability was reduced to about 65% when L3-1Y and Erlotinib were administered in combination. That is, a combination dosage of the agents increased the apoptosis of the resistant cells by about 35%.

6.3. Effect of a Combination Dosage of Anti-c-Met Antibody and EGFR Antagonist on c-Met Degradation An examination was made of the effect of a combination dosage of an anti-c-Met antibody and an EGFR antagonist on c-Met degradation in HCC827 ER15 cells. After HCC827 ER15 cells were treated with a combination of Erlotinib and the antibody L3-1Y or 5D5, levels of c-Met protein in the cells were measured to examine the effect of c-Met antibodies on c-Met degradation.

HCC827 ER15 which was seeded at a density of 2×105 cells/ml/well into 96-well plates was incubated with L3-1Y 0.2 μg/ml+Erlotinib 100 nm, L3-1Y 1.0 μg/ml+Erlotinib 100 nm, 5D5 0.2 μg/ml+Erlotinib 100 nm or 5D5 0.1 μg/ml+Erlotinib 100 nm at 37° C. for 24 hours, and subjected to cell viability assay in the same manner as in Example 1.1, with Erlotinib 100 nm serving as a control.

Cell viability results are expressed as percentages of the c-Met level in the control (treated with Erlotinib alone, 100%) in FIG. 6C, as measured by ELISA. As may be seen in FIG. 6C, a combination of Erlotinib and L3-1Y was found to trigger c-Met degradation in a dose-dependent manner in the Erlotinib-resistant cell line HCC827 ER15, and elicited significant c-Met degradation, compared to a combination of Erlotinib and 5D5.

6.4. Cbl-Independent Inhibitory Activity Against Growth of EGFR-Targeted Therapy-Resistant Sample For an anticancer effect assay, an experiment was made in which colonies grown from lung cancer patients (LXFE1422, LXFA526, LXFA1647; samples susceptible to c-Met small molecule inhibitors, from Oncotest)-derived cell lines (using a 3D culture medium (RPMI (Gibco)) for non-small cell lung cancer (NSCLC), at 37° C.)) were treated with anti-c-Met antibodies.

Of the lung cancer patients, LXFE1422 was not resistant to Cetuximab, an EGFR-targeting anticancer therapeutic, while both LXFA526 and LXFA1647 patients cannot be treated with Cetuximab due to their resistance.

Lung tissues from the patients were lyzed in a lysis buffer Complete lysis-M (Roche, 04719956001) to separate proteins, followed by Western blot analysis. The results are given in FIG. 6D. As may be seen in FIG. 6D, EGFR and Cbl were present at low levels in LXFA526 and LXFA1647 patients, both resistant to Cetuximab.

From the patient samples, the exon 14 coding for the juxtamembrane domain of c-Met was amplified using a one-step RT-PCR kit with the following primers:

```
                                          (SEQ ID NO: 106)
  Primer F: 5'-TGAAATTGAACAGCGAGCTAAAT-3';
  and
                                          (SEQ ID NO: 107)
  Primer R: 5'-TTGAAATGCACAATCAGGCTAC-3'.
```

RT-PCR conditions were as follows:
1 cycle of 50° C. 30 min, 95° C. 15 min,
45 cycles of 94° C. 40 s, 62° C. 40 s, and 72° C. 1 min, and
1 cycle of 72° C. 10 min.

The RT-PCR products including the exon 14 of the c-Met gene were run on agarose gel by electrophoresis, and the agarose gel electrophoresis photograph is given in FIG. 6E. As may be seen, the splice mutation of c-Met itself was found in none of the three patients.

The anticancer activity of the anti-c-Met antibody L3-1Y was proven in the patient samples in which both EGFR and Cbl were expressed at low levels. Cancer cells from the patients were 3D cultured in Oncotest to evaluate colony forming ability. After treatment with L3-1Y 100 µg/ml, the colony forming ability of the cells were evaluated and are expressed as percentages of the number of colonies formed by the control (100 µg/ml treated, 100%) in FIG. 6F. As is apparent from the data of FIG. 6F, the antibody had no efficacy on the LXFE1422 patient, but inhibited cancer growth by 44% (colony formation 56%) for LXFA526, and by 33% (colony formation 67%) for LXFA1647.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of identifying a subject suitable for treatment with an anti-c-Met antibody or antigen-binding fragment thereof that specifically binds to an epitope within a SEMA domain of a c-Met protein, comprising:
   (1) determining the presence of LRIG1 in a cell sample from the subject so as to allow LRIG1-mediated c-Met degradation;
   (2) determining that the subject is suitable for treatment with the anti-c-Met antibody or antigen-binding fragment thereof when LRIG1 is present in the cell sample; and
   (3) administering the anti-c-Met antibody or antigen-binding fragment thereof to the subject determined to be suitable for treatment, wherein the anti-c-Met antibody or antigen-binding fragment thereof comprises SEQ ID NOs: 1-3, 10, 11, and 13, specifically binds to an epitope having 5 to 19 consecutive amino acids of SEQ ID NO: 71 that includes the amino sequence of SEQ ID NO: 73 (EEPSQ) and promotes LRIG1-mediated c-Met degradation.

2. The method of claim 1, wherein the presence of LRIG1 in the cell sample is determined by a method selected from the group of immunochromatography, enzyme linked immunosorbent assay (ELISA), radioimmunoassay (RIA), enzyme immunoassay (EIA), florescence immunoassay (FIA), luminescence immunoassay (LIA), western blotting, or immunohistochemical staining using an anti-LRIG1 antibody.

3. The method of claim 1, further comprising determining a Cbl concentration, a Cbl mutation, or a mutation of a site of c-Met for interaction with Cbl in the cell sample.

4. The method of claim 3, further comprising determining the subject to be suitable for treatment with the anti-c-Met antibody or antigen-binding fragment thereof when Cbl is present at a low level or absent in the cell sample or a mutation is present on either or both Cbl and the site of c-Met for interaction with Cbl.

5. The method of claim 4, further comprising determining the subject to be suitable for treatment with the anti-c-Met antibody or antigen-binding fragment thereof when Cbl is absent or present at a low level in the cell sample or a mutation is present on either or both Cbl and the site of c-Met for interaction with Cbl, and LRIG1 is present in the cell sample.

6. The method of claim 5, wherein Cbl concentration is determined by immunohistochemical staining using an anti-Cbl antibody, which indicates that Cbl is absent or present at a low level in the cell sample.

7. The method of claim 3, wherein the Cbl mutation is a deletion or substitution of 51 or more consecutive nucleotides within nucleotides from $1169^{th}$ to $-1414^{th}$ positions of the nucleotide sequence of GenBank Accession Number NM 005188 (SEQ ID NO: 112), or a deletion or substitution of 17 or more consecutive amino acids within nucleotides from $343^{rd}$ to $424^{th}$ positions of the amino acid sequence of GenBank Accession Number NP 005179 (SEQ ID NO: 113).

8. The method of claim 3, wherein the mutation of a site of c-Met (SEQ ID NO: 114) for interaction with Cbl is a deletion or a substitution of tyrosine at position 1003 (Y1003) with an amino acid other than tyrosine, or a deletion or a substitution of 141 or more consecutive nucleotides within exon 14 of the c-Met gene with other nucleotides, or a deletion or a substitution of 46 or more consecutive amino acids within a polypeptide encoded by exon 14 of the c-Met gene with other amino acids.

9. The method of claim 1, wherein the anti-c-Met antibody or antigen-binding fragment thereof heavy chain variable region comprises SEQ ID NO: 17 and the light chain variable region comprises SEQ ID NO: 111.

10. The method of claim 1, wherein the anti-c-Met antibody or antigen-binding fragment thereof comprises
   a heavy chain comprising the amino acid residues from the $18^{th}$ to $460^{th}$ positions of SEQ ID NO: 66 and a light chain comprising the amino acid residues from the $21^{st}$ to $240^{th}$ positions of SEQ ID NO: 68.

11. The method of claim 1, wherein the anti-c-Met antibody or antigen-binding fragment thereof is an antibody of mouse origin, a mouse-human chimeric antibody, a humanized antibody, or a human antibody.

12. The method of claim 1, wherein the anti-c-Met antibody or antigen-binding fragment thereof is an antigen-binding fragment selected from the group consisting of scFv, (scFv)$_2$, Fab, Fab', and F(ab')$_2$ of the anti-c-Met antibody.

13. The method of claim 1, wherein the cell sample is a sample of cancer cells.

* * * * *